US012007375B2

United States Patent
Rigby et al.

(10) Patent No.: US 12,007,375 B2
(45) Date of Patent: Jun. 11, 2024

(54) FRESHNESS SENSOR DEVICES AND RELATED METHODS

(71) Applicant: THE KROGER CO., Cincinnati, OH (US)

(72) Inventors: Adam Rigby, Fort Mitchell, KY (US); Chris Daniels, Southgate, KY (US); Addison Carter, Cincinnati, OH (US); Seth Blovits, Cincinnati, OH (US); Connor Rahm, Goshen, OH (US); Noe Alvarez, Cincinnati, OH (US); Olivia North, Cincinnati, OH (US); Brendan Payne, Cincinnati, OH (US); Michael Jordan, Park Hills, KY (US); Fernando Eli Garcia, Cincinnati, OH (US)

(73) Assignee: THE KROGER CO., Cincinnati, OH (US)

( * ) Notice: Subject to any disclaimer, the term of this patent is extended or adjusted under 35 U.S.C. 154(b) by 0 days.

(21) Appl. No.: 18/129,134

(22) Filed: Mar. 31, 2023

(65) Prior Publication Data
US 2023/0314392 A1 Oct. 5, 2023

Related U.S. Application Data

(63) Continuation of application No. PCT/US2021/057083, filed on Oct. 28, 2021.
(Continued)

(51) Int. Cl.
*G01N 33/02* (2006.01)
*B01L 3/00* (2006.01)
(Continued)

(52) U.S. Cl.
CPC ........ *G01N 33/02* (2013.01); *B01L 3/502715* (2013.01); *G06K 7/10297* (2013.01);
(Continued)

(58) Field of Classification Search
CPC ............... G01N 33/02; B01L 3/502715; B01L 2300/022; B01L 2300/0645;
(Continued)

(56) References Cited

U.S. PATENT DOCUMENTS 6,285,282 B1  9/2001  Dorenbosch et al.
6,751,935 B2  6/2004  Brenkus
(Continued)

FOREIGN PATENT DOCUMENTS

DE  10104968 A1  8/2002
DE  10164222 A1  7/2003
(Continued)

OTHER PUBLICATIONS

United States Patent and Trademark Office, International Search Report and Written Opinion issued in corresponding Application No. PCT/US2021/057083, dated Feb. 7, 2022.
(Continued)

*Primary Examiner* — Brian J. Sines
(74) *Attorney, Agent, or Firm* — Stites & Harbison, PLLC; Terry L. Wright

(57) ABSTRACT

A device for detecting freshness of a perishable item is provided. The device includes at least one sensor for detecting an analyte of interest in the perishable item. The device further includes an integrated circuit for converting information detected by the sensor into a signal. The device also includes an antenna portion for receiving and transmitting the signal from the integrated circuit. The at least one sensor, integrated circuit and antenna portion are printed on a single sheet such that the device is unitary.

7 Claims, 55 Drawing Sheets

Related U.S. Application Data

(60) Provisional application No. 63/106,707, filed on Oct. 28, 2020.

(51) Int. Cl.
*G06K 7/10* (2006.01)
*G06K 19/06* (2006.01)
*G06K 19/077* (2006.01)

(52) U.S. Cl.
CPC ... *G06K 7/10366* (2013.01); *G06K 19/06121* (2013.01); *G06K 19/07718* (2013.01); *G06K 19/0772* (2013.01); *B01L 2300/022* (2013.01); *B01L 2300/0645* (2013.01); *B01L 2300/0816* (2013.01); *B01L 2300/16* (2013.01)

(58) Field of Classification Search
CPC ..... B01L 2300/0816; B01L 2300/0627; B01L 2300/0636; G06K 7/10297; G06K 7/10366
See application file for complete search history.

(56) References Cited

U.S. PATENT DOCUMENTS

| | | | |
|---|---|---|---|
| 6,765,490 | B2 | 7/2004 | Lopez et al. |
| 6,982,640 | B2 | 1/2006 | Lindsay et al. |
| 8,258,943 | B2 | 9/2012 | Park et al. |
| 8,552,730 | B2 | 10/2013 | Chiao et al. |
| 9,712,893 | B2 | 7/2017 | Warkentin et al. |
| 9,884,715 | B2 | 2/2018 | Hoofman et al. |
| 9,886,658 | B1 | 2/2018 | Stanford et al. |
| 9,946,904 | B2 * | 4/2018 | Burchell ............ G01K 1/024 |
| 10,242,550 | B2 | 3/2019 | Glasgow et al. |
| 10,271,738 | B2 | 4/2019 | Peeters |
| 10,386,347 | B2 | 8/2019 | Olsson |
| 2005/0248455 | A1 | 11/2005 | Pope et al. |
| 2006/0132290 | A1 | 6/2006 | Yuan et al. |
| 2007/0008112 | A1 | 1/2007 | Covannon et al. |
| 2007/0029384 | A1 | 2/2007 | Atherton |
| 2007/0176773 | A1 | 8/2007 | Smolander et al. |
| 2011/0140703 | A1 | 6/2011 | Chiao et al. |
| 2013/0069120 | A1 | 3/2013 | Merz et al. |
| 2014/0144992 | A1 | 5/2014 | Diorio et al. |
| 2017/0038325 | A1 | 2/2017 | Takashima et al. |
| 2017/0364785 | A1 | 12/2017 | Swager et al. |
| 2020/0008299 | A1 | 1/2020 | Tran et al. |

FOREIGN PATENT DOCUMENTS

| | | |
|---|---|---|
| DE | 10065545 B4 | 12/2006 |
| JP | 2003083925 A | 3/2003 |
| KR | 20110026607 A | 3/2011 |
| WO | 2014082563 A1 | 6/2014 |
| WO | 2017063318 A1 | 4/2017 |
| WO | 2021224630 A1 | 11/2021 |

OTHER PUBLICATIONS

Mjayalakshmi, J., et al. A Ultra High Frequency (UHF) RFID Antenna Design for Food Quality and Safety. International Journal of Recent Technology and Engineering (IJRTE), ISSN: 2277-3878, vol. 8, Issue 6, Mar. 2020.

Kuswandi, B. "Freshness sensors for food packaging." Reference Module in Food Science (2017).

Wang, L., et al. "Technologies and Fabrication of Intelligent Packaging for Perishable Products." Applied Sciences 9.22 (2019): 4858.

Potyrailo, R.A., et al. "Battery-free radio frequency identification (RFID) sensors for food quality and safety." Journal of agricultural and food chemistry 60.35 (2012): 8535-8543.

Lopez-Gomez, A., et al. "Radiofrequency identification and surface acoustic wave technologies for developing the food intelligent packaging concept." Food engineering reviews 7.1 (2015): 11-32.

Yuan, M., et al. "Self-powered wireless biosensing based on integration of paper-based microfluidics with self-assembling RFID antennas." 2015 IEEE Biomedical Circuits and Systems Conference (BioCAS). IEEE, 2015.

Ma, Z., et al. "Highly sensitive, printable nanostructured conductive polymer wireless sensor for food spoilage detection." Nano letters 18.7 (2018): 4570-4575.

Nguyen, S.D., et al. "Approach for quality detection of food by RFID-based wireless sensor tag." Electronics Letters 49.25 (2013): 1588-1589.

Smits, E., et al. "4.5. 2 Development of printed RFID sensor tags for smart food packaging." Tagungsband (2012): 403-406.

Lee, C.W., et al. "The Design of Smart RFID Tag System for Food Poisoning Index Monitoring." (2013).

Eom, K-H, et al. "The meat freshness monitoring system using the smart RFID tag." International Journal of Distributed Sensor Networks 10.7 (2014): 591812.

Fuertes, G., et al. "Intelligent packaging systems: sensors and nanosensors to monitor food quality and safety." Journal of Sensors 2016 (2016).

* cited by examiner

FRESHNESS SENSOR DEVICES AND RELATED METHODS

RELATED APPLICATIONS

This application is a continuation of International Patent Application No. PCT/US21/57083 filed on Oct. 28, 2021, which claims priority from U.S. Provisional Application Ser. No. 63/106,707, filed Oct. 28, 2020, the entire disclosure of which is incorporated herein by this reference.

TECHNICAL FIELD

The present invention relates to freshness sensor devices and related methods of making and using the devices. More particularly, the present invention relates to a printable sensor device that can be incorporated into multi-functional and other substrates for detecting the putrefaction and decay of individual perishable items as well as the multiplication and growth of harmful bacteria on those perishable items over a period of time and for real-time communication of that information to retail stores and consumers. Detection results are stored for use in a software application and are capable of use in product recall and other aftersale activities.

BACKGROUND

Retail stores, such as grocery stores and supermarkets, lose a considerable amount of revenue each year as the result of unsold fruits, vegetables, meats, and/or other perishable items that are no longer fresh and, thus, are lost to waste. Revenue is also frequently lost in such situations as a result of improper inventory tracking whereby if a recall of a particular type of perishable is issued from one supplier, inventory from that supplier as well as from a second supplier providing the same or similar type of perishable may both be disposed of as it may be impossible to identify from which supplier the recalled item originated.

In order to monitor environmental factors affecting the freshness of perishable items, it is known to rely on qualitative measures, such as observing the color or smell of the perishable item, which are notoriously unreliable and imprecise. Alternatively, freshness of perishable items may be determined quantitatively by colony forming units on the surface of the product that typically happens in the suppliers or product quality laboratories. Typically, these direct methods require lab technicians to perform the tests.

While some sensing devices have been developed to replace the qualitative and quantitative methods discussed above, they still suffer from certain limitations. For example, the sensing devices do not rely on determination of amines, Total Volatile Basic-Nitrogen (TVB-N) and gaseous reaction byproduct concentration by microbes and bacteria in order to determine freshness and are, thus, not particularly reliable or accurate. Furthermore, these sensing devices are quite bulky as they include a number of discrete components that are not incorporated into a single device. As a result, these devices cannot be used on a specific perishable item. Instead, these devices are typically used to monitor perishable items in bulk, such as during transport of the perishable items to the retail store or at the retail store wherein the perishable items are displayed for purchase.

Because known sensing devices are not used on a per item basis, retail stores are typically forced to treat all of the items of a particular product the same, even though their freshness is not identical, which is wasteful and expensive. Furthermore, because known sensing devices are not used on a per item basis, a particular item cannot be monitored in real-time throughout its retail journey. Rather, monitoring typically ends when the product is purchased and, thus, the consumer is not provided any additional freshness data after purchase, which can also lead to waste and/or safety issues regarding consumption of the perishable item.

Accordingly, improved freshness sensor devices for detecting the putrefaction and decay of perishables and the multiplication and/or growth of harmful bacteria and microbes on those perishables over a period of time and for communicating that information to retail stores and consumers would be both highly desirable and beneficial. The improved freshness sensor device would integrate all the components into a single device on a multi-functional or other substrate for real-time monitoring of individual perishable items and would be capable of providing real-time monitoring data of the individual perishable item's freshness at the retail store and consumer's home.

SUMMARY

The present invention includes freshness sensor devices and related methods of using the devices. More particularly, the present invention includes a printable sensor device that can be incorporated into multi-functional and other substrates for detecting the putrefaction and decay of individual perishable items as well as the multiplication and growth of harmful bacteria on those perishable items over a period of time and for real-time communication of that information to retail stores and consumers.

In accordance with one aspect of the disclosure, a device for detecting freshness of a perishable item is provided. The device includes at least one sensor for detecting an analyte of interest in the perishable item. The device further includes an integrated circuit for converting information detected by the sensor into a signal. The device also includes an antenna portion for receiving and transmitting the signal from the integrated circuit. The at least one sensor, integrated circuit and antenna portion are printed on a single sheet such that the device is unitary.

In one embodiment, the antenna portion is responsive to a signal from an aerial device. The aerial device may be one of near field communication (NFC), radio frequency identification (RFID), Zigbee, 802.15.4, Thread or Bluetooth. A circuit may be formed between the antenna portion and the aerial device. Once an amount of the analyte of interest detected by the at least one sensor exceeds a predefined limit, the circuit between the antenna portion and the aerial device is broken. In some embodiments, the circuit between the antenna portion and integrated circuit and the aerial device is not broken regardless of the particular state of the sensor.

In another embodiment, the device may include an analog/digital (A/D) converter in communication with the at least one sensor and the aerial device. The at least one sensor varies an output based on an amount of the analyte of interest detected. In yet another embodiment, the at least one sensor may be a binary sensor. The IC portion may detect a resistance change based on the binary sensor and transmit the resistance change data to an external receiver. The antenna portion may determine a continuity data based on the binary sensor and transmit the continuity data to an external receiver.

In still yet another embodiment, the at least one sensor is a plurality of sensors. Each of the plurality of sensors may be tuned to a corresponding concentration of the analyte of interest. Each of the corresponding concentration of the analyte of interest increases with respect to each successive one of the plurality of sensors. Each of the plurality of sensors may be configured to detect a different analyte of interest. The different analyte of interest is a different chemical for each of the plurality of sensors.

In accordance with another aspect of the disclosure, a system for detecting freshness of a perishable item is provided. The system includes a substrate, a sensor printed on the substrate, an integrated circuit for converting data from the sensor into a signal, and a radio device for receiving and transmitting the signal from the integrated circuit. The system further includes a first receiving device for receiving the signal from the radio device via a software application running on the first receiving device and converting the signal into a freshness value for the perishable item.

In one embodiment, the sensor is a chemical sensor for detecting an analyte of interest in the perishable item. The analyte of interest may be a change in amines and TVB-N's being released by a decay process of the perishable item or a change introduced by a bacterial and microbial reaction of the perishable item.

In another embodiment, the freshness value is unique to a particular perishable item. The freshness value of the perishable item may be displayed on the first receiving device via the software application. The freshness value, item identifier, and freshness timing of the perishable item may be accessible by an additional device or devices, or processes.

In accordance with yet another aspect of the disclosure, a sensor tag for detecting freshness in an environment is provided. The sensor tag includes a chemical sensor for detecting a change in the environment. The sensor tag further includes an integrated circuit for converting a signal relating to the change into deliverable information. The sensor tag also includes an antenna for receiving and transmitting the deliverable information. The at least one sensor, the integrated circuit, and the antenna portion are printed on a paper substrate.

In one embodiment, the antenna may be responsive to a NFC signal, a RFID signal or both. In another embodiment, the antenna includes a first antenna responsive to a NFC signal and a second antenna responsive to a RFID signal. In yet another embodiment, the chemical sensor is a binary sensor. In still yet another embodiment, the chemical sensor is at least two sensors, the at least two sensors configured to detect multiple changes in the environment. A semi-permeable membrane may coat the chemical sensor. The sensor tag is about ninety-five percent (95%) biodegradable.

In accordance with still yet another aspect of this disclosure, a multi-functional substrate is provided. The substrate has a first side and an opposed, second side. The second side supports an integrated circuit and an antenna. The first side is configured to detect an analyte of interest, while the integrated circuit is configured to convert data relating to the analyte of interest into a signal and the antenna transmits the signal to an external receiver.

In one embodiment, the multi-functional substrate is made of paper. In another embodiment, the second side includes a waterproof coating. In yet another embodiment, the second side includes a dielectric coating. In some embodiments, the single coating may act as both a dielectric and a waterproof coating. In still yet another embodiment, the first side is uncoated. In an additional embodiment, the first side includes a sensor printed material.

In accordance with still yet another aspect of this disclosure, a method for detecting freshness of a perishable item is provided. The method includes the following steps: (1) placing a sensor device for detecting freshness in proximity with the perishable item and allowing exchange of gases with the perishable item; (2) detecting an analyte of interest from the perishable item; (3) converting data from the analyte of interest into a signal; (4) transmitting the signal from the sensor device to a receiving device; (5) analyzing the signal, via a software application running on the receiving device; and (6) determining a freshness value of the perishable item.

In one embodiment, the placing step includes placing the sensor device within a sealed packaging of the perishable item. In another embodiment, the placing step includes placing the sensor device on a label associated with the perishable item. In another embodiment, the sensor device is included in an absorbent pad used commonly in perishable items.

In another embodiment, the analyzing step includes decoding the signal and converting the decoded signal into useable information containing a unique identifier for the perishable item. The analyzing step may also include linking the unique identifier to a database associated with the software application. The determining step may include utilizing the database to create a freshness data point and storing the freshness data point in the software application. The method may further include time-stamping the freshness data point in the software application and allowing the software application to match the freshness data point with a predicted trend for the perishable item. The method may also include updating the predicted trend based upon the freshness data point.

In other embodiments, the method may include estimating a number of days remaining until spoilage based upon the freshness value and displaying the freshness data value of the perishable item on the receiving device.

In accordance with yet another aspect of the disclosure, a method for making a sensor tag is provided. The method includes: (i) providing a single sheet substrate; (ii) printing a dielectric layer on a first portion of the substrate; (iii) printing a sensor on a second portion of substrate; (iv) printing a desired circuit pattern over the dielectric layer with a conductive ink; (v) cutting vias in the substrate; (vi) picking and placing an integrated circuit chip on the substrate; (vii) connecting the vias and integrated circuit chip; and (viii) otherwise encapsulating the electronic sensor device with the exception of the sensing element.

In one embodiment, the printing step includes utilizing a rotary screen printing process. In another embodiment, the method includes providing a non-conductive immobilization coating over the integrated circuit chip and die-cutting the sensor device.

In accordance with one aspect of the disclosure, a switching mechanism for a sensing device is provided. The switching mechanism includes a sensor for detecting an analyte of interest in a perishable item to generate a charge, an alternating to direct current converter circuit in electrical connection with the sensor and a transistor in electrical connection with the alternating to direct current converter circuit. The sensor draws a current from the potential difference to create a switching mechanism with the alternating to direct current converter circuit and the transistor.

In one embodiment, the analyte of interest is a change in amines and TVB-N's or other gases being released by a decay process of the perishable item. In another embodiment, the analyte of interest is a change introduced by a bacterial and microbial reaction of the perishable item. The sensor may include a plurality of electrodes and the plurality of electrodes may draw an external voltage when polarized.

In yet another embodiment, the sensor may be a binary chemical sensor. The transistor may be one of a JUGFET, MOSFET or JFET transistor. The alternating to direct current converter circuit may include four diodes. In certain embodiments the current may be direct or indirect. The switching mechanism may also include an operational amplifier.

In accordance with another aspect of the disclosure, a method of using a switching mechanism is provided. The method includes providing a freshness sensor, wherein the sensor is a chemical sensor having a plurality of electrodes, an alternating to direct current converter circuit having a plurality of diodes and a transistor. The method further includes generating a charge within the sensor from an external source and building the charge to polarize the plurality of electrodes. The method also includes drawing an external current to activate the alternating to direct current converter circuit and switching the transistor to indicate detection of the analyte of interest.

Further features and advantages of the present invention will become evident to those of ordinary skill in the art after a study of the description, figures, and non-limiting examples in this document.

DESCRIPTION OF EXEMPLARY EMBODIMENTS

The present invention includes a freshness sensor system or device and related methods of using the device for detecting the putrefaction and decay of perishable items and the multiplication/growth of harmful bacteria and microbes on those perishable items over time. The freshness sensor device is able to communicate that information and additional product information to the consumers and/or the retail store as well as other parts of a distribution chain. The freshness sensor device allows for real-time tracking of the perishable item from its initial location of "activation" to its final destination, i.e., the retail store and/or consumer's home. "Activation" generally refers to when the device is originally coded and implanted into the perishable item's package or environment it is designed to monitor.

Figure 1A:
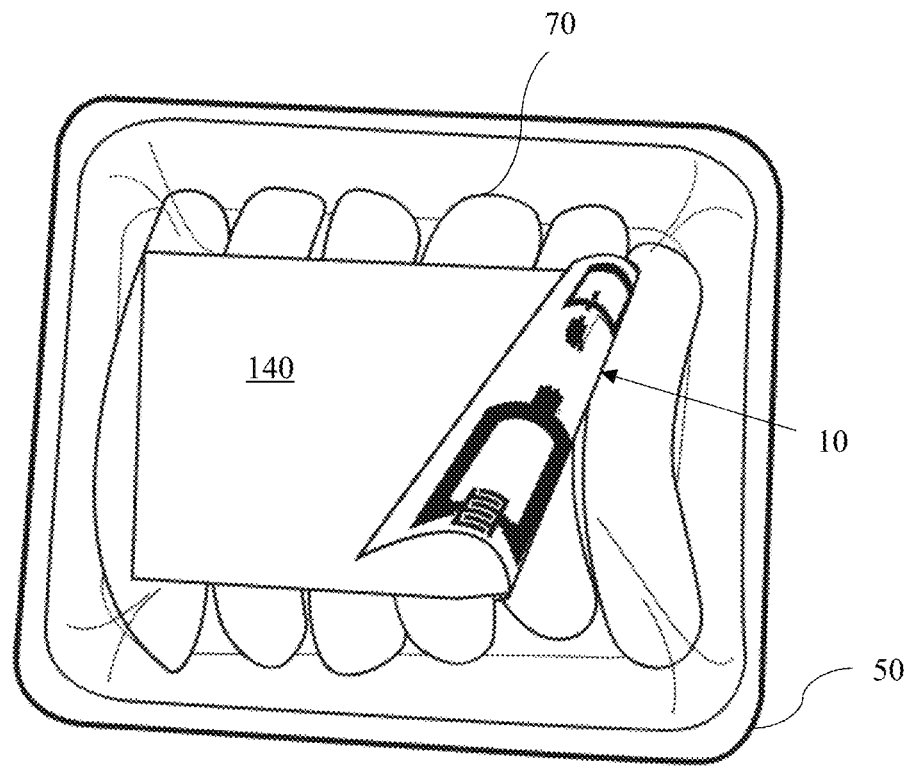
FIGS. 1A-1C are perspective views of the freshness sensor device forming one aspect of this disclosure.
Figure 1B:
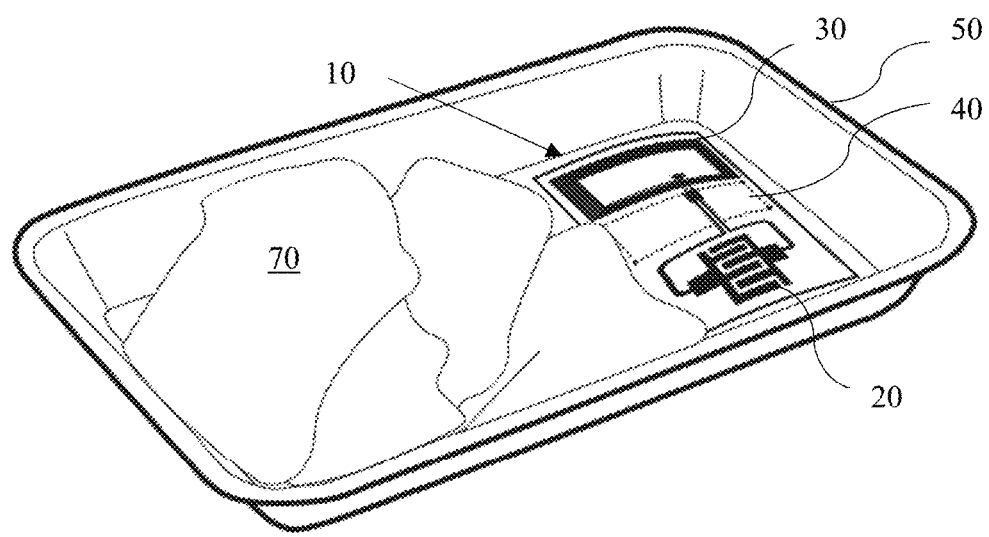
Figure 1C:
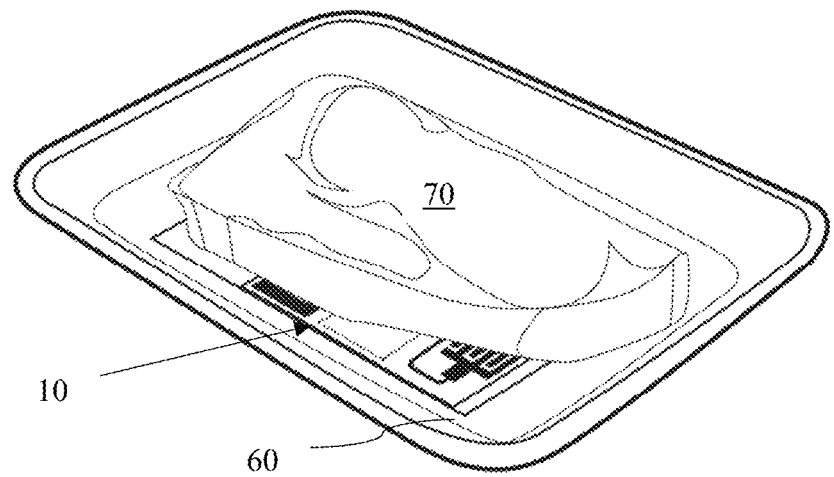
Figure 77:
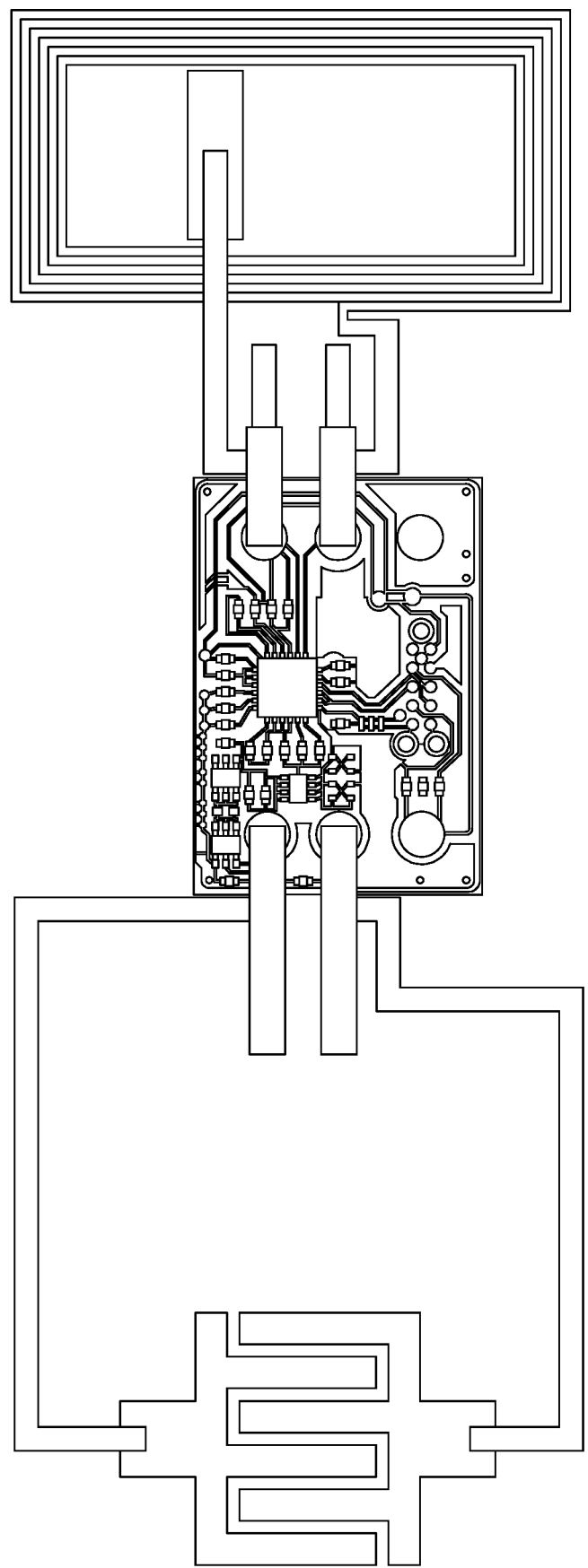
FIG. 77 is an image showing an exemplary device for detecting freshness in accordance with one aspect of this disclosure.

Reference is now made to FIGS. 1-77, which illustrate a freshness sensor device 10 for perishable items, such as fruit, vegetables and meat as well as related methods of making and using such devices and its components. The freshness sensor device 10 includes multiple components integrated into a single, compact unit, such as a printed label, tag or bar code. In the embodiment illustrated in FIGS. 1A-1C, the freshness sensor device 10 includes: (i) one or more sensor(s) 20 for detecting an analyte or analytes of interest or change in the perishable item(s), such as ammonia ($NH_3$) levels in a package of meat; (ii) a radio device or antenna portion 30 (with some other components, resistors, inductors, coils, etc.) for receiving and transmitting the deliverable information to a receiver, external to the device 10; and (iii) an integrated circuit (IC) 40 (including a variety of discrete electronic components), which may be integrated with the antenna portion 30. In some embodiments, the receiver may be a Radio Frequency Identification (RFID) reader or a mobile phone for reading a Near Field Communication (NFC) signal. Of course, other reading devices, mobile devices or computing devices are also capable of being used in accordance with the present invention.

The IC 40 is in electrical communication with the sensor(s) 20 and the antenna portion 30. The IC 40 is configured to process/convert a signal from the sensor 20 corresponding to the detected analyte of interest into a form of deliverable information sent by the antenna portion 30 to the receiver. The deliverable information may be a signal of any of the following types: NFC, RFID, Zigbee, 802.15.4, Thread/Bluetooth Low Energy (or passive Bluetooth) or other aerial signal from an aerial device or chip. The signal sent to the receiver is indicative of the analyte of interest sensed, such a specific chemical compound released by the perishable item or temperature of the perishable item. In one particular embodiment, the antenna or aerial chip utilized herein may be a Texas Instruments Model No. RF430FRL152H. Of course, it should be appreciated that other chips may be utilized with the freshness sensor device 10 disclosed herein.

The device 10 may be on the backside of a printed label 140 (see FIG. 1A), free floating in a package 50 (see FIG. 1B) or integrated with a meat purge pad/pack 60 (see FIG. 1C). It should be appreciated that the device 10 may also be associated and/or attached to the food packaging or directly to the perishable item in other suitable ways or at other locations within the environment. It should be appreciated that the specific location of the device may require additional calibrations and adjustments to the sensors responses based on the variations and influences generated by the changed proximity and orientation of the sensor to the meat or other perishable item, as well as the environment variations the sensor is inhabiting.

The device 10 can be fabricated to contain either a single sensor or multiple sensors that are able to detect changes in the perishable and/or the package's internal or sealed environment. The device 10 has the potential to be applied for a variety of gas analytes: volatile organic carbons (VOC), volatile biogenic-amines (TVB), environmental green house gases, gaseous HCl, $NH_3$, $N_2H_4$, $CHCL_3$, $CO_2$ and others. The material used as the recognition element for device 10 can vary including, activated carbon, carbon black, carbon nanotubes, graphene, conducting polymers such as poly aniline (PANT), and conductive metals such silver, gold, nickel or copper. The type and use of transducer for device 10 can vary from near field communication (NFC), RFID, among other IC components. This list of sensors/tags and analytes of interest is merely representative and other sensors/tags/analytes may be utilized with the device.

Research shows that there are printable materials that are able to detect changes in amines and TVB-N's being released by the decay process, and other printable or sprayable materials that are able to detect the changes introduced by bacterial and microbial metabolic reactions. The printable materials are electrically conductive and able to interact with Near Field Communication (NFC)/Radio Frequency Identification (RFID)/Zigbee/802.15.4/Thread/Bluetooth Low Energy (or passive Bluetooth) aerial devices. In certain embodiments, multiple aerial devices may be fabricated into the device such the device covers the range needed to reach from NFC to Zigbee and 5G.

The sensors may act as either a binary (fresh or unfresh) sensor or a discreetly graded sensor that is able to detect multiple degrees of freshness. Advantageously, the discreetly graded sensors are able to estimate a more specific time duration for the remainder of the food's freshness life-span.

Unlike other freshness sensor devices, the device is designed to be printed onto a paper substrate. Typically, sensors and aerial components are printable or sprayable onto either a single or other sheeted or rolled materials. However, to reduce overall size of the device, multiple sheets can be used. In some embodiments, the device 10 is designed with materials that are approximately ninety-five percent (95%) biodegradable and completely safe for the environment, with an expected degradable life span of the paper backbone used to absorb the liquid electrode applied to its surface. The sensor fabrication process may utilize a screen or print press process, which is not commonly used for paper-based sensor manufacturing.

There are multiple ways that the results of the change to sensor properties can be used to signal the state of the attached food. For example, such changes in sensor properties may be achieved in the following ways: (1) using the sensor as a break point in the circuit from antenna to NFC/RFID/Bluetooth; (2) using the NFC/RFID/Bluetooth attached to an analog/digital (A/D) converter; (3) direct wiring of the sensor to the NFC/RFID/Bluetooth to provide a binary signal; (4) extending the approach of (3) with a sensor ladder: (5) a multi-sensor design that is able to give binary responses to multiple compound detections; and (6) a multisensory system including a single multi-sensor configured to sense multiple compound detections, wherein all work on external signal is by mobile telephone or other RF source. It should also be appreciated that this list is not exhaustive and changes in sensor properties may be achieved in other ways.

The freshness sensor devices 10 described in the circuit designs below work based on a similar principal. Namely, the appearance or introduction of an external stimulus generates a charge (directly or indirectly) within the device. For example, an aerial signal may be transmitted by an external source (not shown) and being of the proper frequency and incident of the antenna portion 30 such that the signal interacts with the antenna portion to supply power to the sensor 20. Electromagnetic energy (such as electrons)

are then supplied to the integrated circuit (IC) 40 and stored in the aerial chip to complete and close the circuit. While it is noted above that an external stimulus is described for generating a charge within the device, it should be appreciated that the sensor 20 and IC 40 may have their own internal power supply, i.e., a battery.

At this point, the sensor 20 begins detecting for an analyte of interest from the perishable item. In one embodiment, the sensor may be a chemical sensor detecting an emission of a chemical (i.e., TVB-N) from the perishable item. Typically, a chemical sensor has electrical properties that can be measured in terms of electrical parameters, such as resistance, capacitance or inductance. For example, when an analyte of interest is detected, the chemical sensor will have a measurable response characteristic.

In certain embodiments, upon detection of the analyte of interest, a small chemical reaction upon the surface of the sensor 20 occurs. This chemical reaction may be mediated by either a chemical coating that is positioned on a substrate 330 (i.e., a printed sensor material on the substrate) or a chemical deposition that naturally occurs (directly on the substrate), i.e., the buildup of a moisture layer caused by the hydrophilic nature of the substrate being used, more specifically Whatman Cellulose Paper (discussed in more detail below).

The dissolution of gaseous species from positively and negatively charged ions in the water layer that, over a short period of time, collect at the reciprocal charge electrodes in the sensor 20 (positive charges are attracted to the anode and negative charges to the cathode). As the charge builds up, the electrodes become polarized such that the polarized electrodes draw an external current through the attraction of a non-Faradaic process (wherein charge is stored). Other chemical sensors may draw an external current through the application of a Faradaic process, which draws charges directly from the interacting chemicals, i.e., a charge transfer.

For TVB-N detection, a non-Faradaic process is used to generate a measurable resistance change similar to how thermal resistors work. As such, in certain embodiments, a thermal resistor may replace the chemical sensor described herein. It should be appreciated that the sensors described below are analogous and interchangeable and not limited to chemical, chemiresistive, thermal or piezoelectric sensors.

Figure 3:
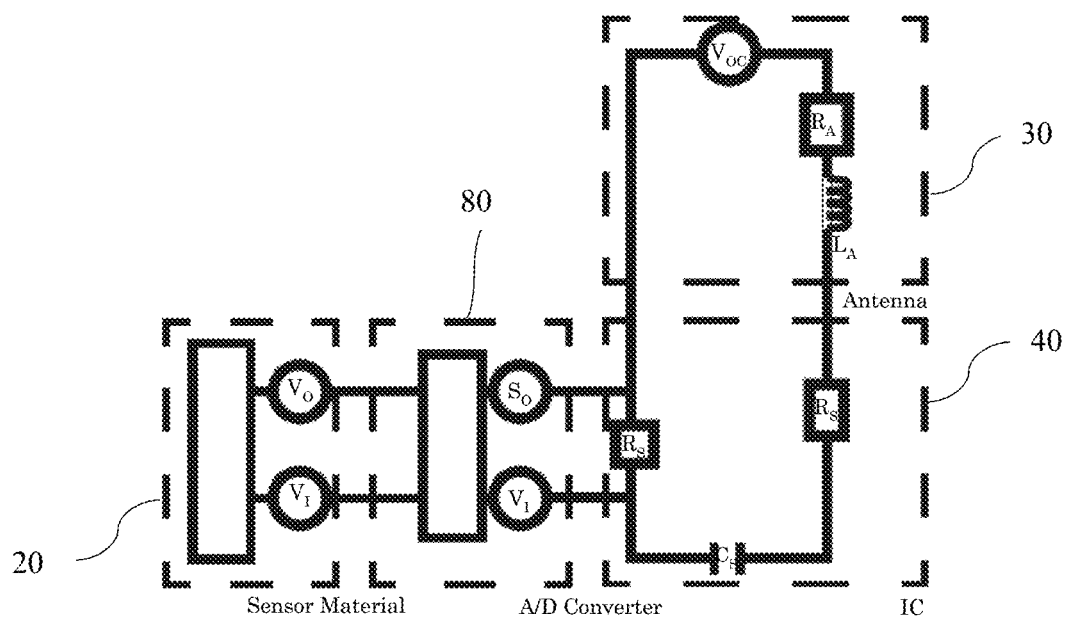
FIG. 3 is a circuit diagram for a freshness sensor device designated a variable concentration signal sensor forming one aspect of this disclosure.

Depending on the purpose for which the sensor tag or device 10 is being developed (thermal sensor for temperature changes, humidity sensor for humidity changes, chemical sensor for chemical changes), the devices 10 may use the sensor 20 in identical ways. The application of an Analog to Digital (A/D) converter 80 in FIG. 3 allows for more accurate and greater coverage of the sensors detection ranges being utilized. Without the application of the A/D converter 80 and corresponding circuit, the sensor 20 may act as a binary switch (on/off) in conjunction with a short circuit resistance circuit or a stepladder switching circuit (capable of detecting multiple concentrations of a single chemical or multiple chemicals).

Figure 2:
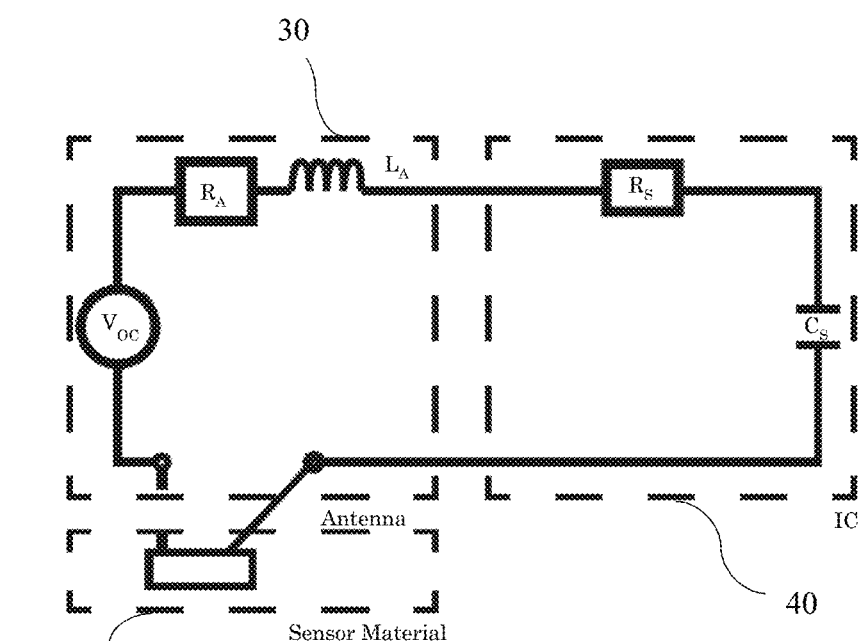
FIG. 2 is a circuit diagram for a freshness sensor device designated a break sensor forming one aspect of this disclosure.

The former function can be described using the TVB-N sensor 20 and illustrated in FIG. 2. Until the point of detection of a desired analyte of interest from the perishable item by the sensor 20, the baseline resistance is relatively high, i.e., 50 kΩ (kOhms) or more. Until detection of the desired analyte of interest, the current is forced around a first path in the circuit. However, upon detection of the desired analyte of interest, the resistance of the sensor 20 drops dramatically, which opens/closes a switch to create an alternate second path in the circuit. When the second path is utilized, no signal is sent by antenna to the receiver and, therefore, the lack of signal to an external receiver indicates that the perishable item is no longer fresh to consume. In other words, the chemical sensor acts as a chemical switch to open the second path.

Turning to FIGS. 63-73, the sensor device 10 may utilize a binary chemical switching mechanism that is able to activate or deactivate in the presence of an external influence. The switching mechanism may be utilized in determining the freshness of perishable items as well as in numerous other applications. The sensor device incorporating the binary chemical switching mechanism may be printed on or positioned on any suitable substrate, such as the ones described herein. In one particular embodiment, the sensor device may be printed on a paper substrate.

In use, the switching mechanism acts under the presence of external, but specific stimulus, including, but not limited to, a chemical indicator of food decay. For example, the sensor device may be configured to effectively monitor environmental factors affecting the freshness of perishable items, including, but not limited to amines, TVB-N and gaseous reaction byproduct concentration by microbes and bacteria.

Figure 63:
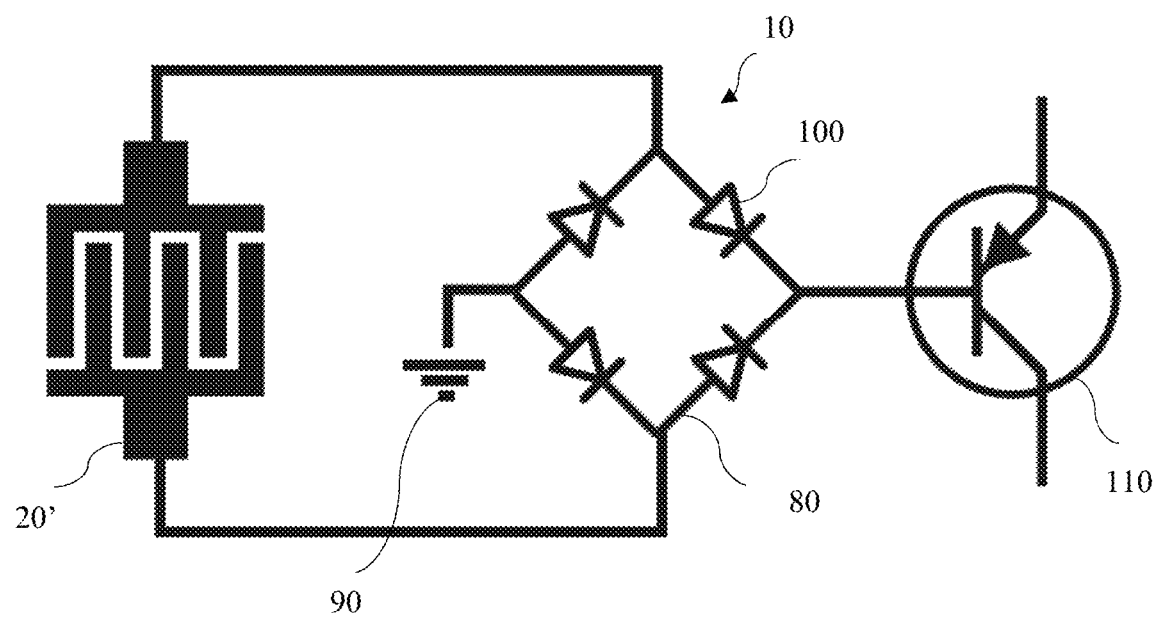
FIG. 63 is a schematic diagram of a switch circuit including a sensor forming one aspect of this disclosure.

With reference to FIG. 63, a diagram of a switch circuit illustrated. The switch circuit for the sensor device 10 includes a sensor 20', which may be a printed binary chemical sensor. Furthermore, an alternating to direct current converter circuit 80 is electrically connected to the sensor 20' and ground 90. In the illustrated embodiment, the alternating to direct current converter circuit has four (4) diodes 100. A transistor 110 is also connected to the alternating to direct current converter circuit. The transistor may be a junction field-effect transistor (JUGFET), a metal-oxide-semiconductor field-effect transistor (MOSFET), junction-gate field-effect transistor (JFET) or other simple transistor.

As shown in FIG. 63, the sensing device disclosed herein is known as a three-component switching device, i.e., the sensor 20', the alternating to direct current converter circuit 80 and the transistor 110. It is emphasized that traditional switching devices make use of a single component to connect or break the circuit or activate a separate device function, while the present disclosure does not rely on traditional circuit breaking.

In use, the appearance or introduction of an external stimulus generates a charge (directly or indirectly) within the device 10. The charge builds up, which polarizes electrodes within the sensor. The polarized electrodes are then able to draw an (extremely small) external voltage over time to act as a circuit switching mechanism by switching the transistor 110, which grounds out the circuit (indicating that the food is no longer fresh to eat).

It is the charge building up whereby an external current is drawn in conjunction with the transistor 110 and the alternating to direct convert circuit 80 that creates a consistent switching device in the presence of the external influence. Although switch mechanisms are known (although not in the field of food freshness detection), known switch mechanisms use the sensor resistance change to affect the switching. This phenomenon does not occur with the present disclosure because no charge flows through the sensor device whilst activated and connected in series to the circuit.

In certain embodiments, it is desirable to amplify the generated charge to reduce the amount of electrical potential needed to activate the switch or to amplify the voltage and current interacting with the transistor. For example, amplification may be necessary or desirable depending on the sensitivity of the sensor and/or the power required to switch the transistor and activate the diodes. Amplification may be performed by an operational amplifier (also known as "opamp" or "op amp") device (not shown), which is an integrated circuit design to amplify weak electric signals. In this case, the opamp is isolated and unable to activate and, therefore, the switch is allowed to activate under more sensitive conditions.

For example, in one embodiment directed to an ammonia switch, a voltage of 5 mV is created when a small amount of ammonia, i.e., 15-25 PPM is detected by the sensor. However, in this embodiment, the diodes for the alternating to direct convert circuit require 0.7 V in order to activate. Accordingly, to effectively act as a switching mechanism, the opamp must amplify the voltage by a factor of 140. In other embodiments, multiple opamps, i.e., one at each detector electrode, may be desirable to address randomly polarization.

Figure 66:
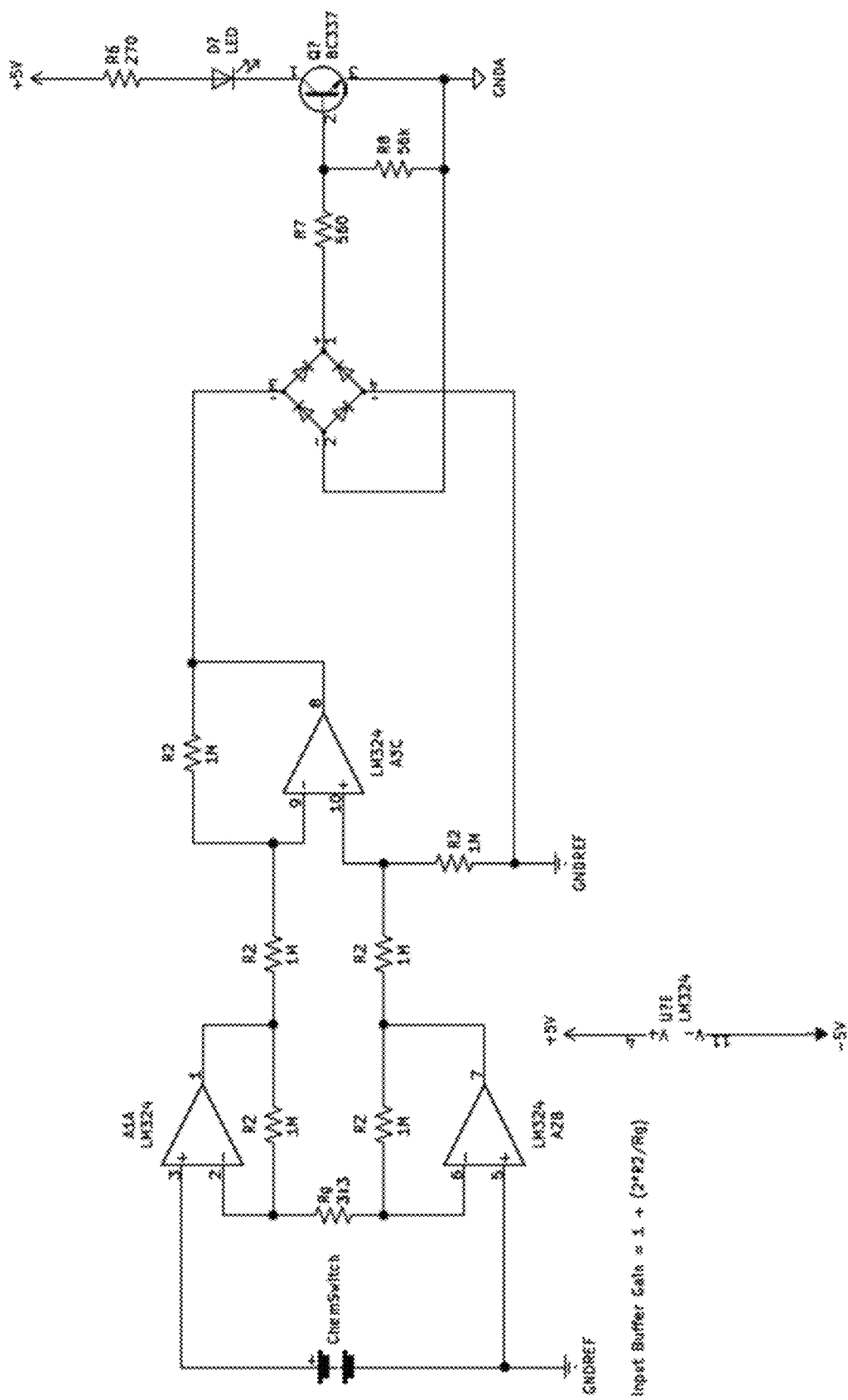
FIG. 66 is a circuit diagram for the sensor switch forming one aspect of this disclosure.
Figure 67:
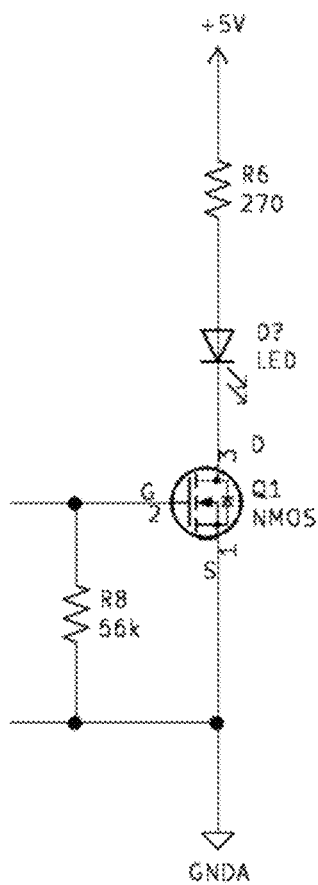
FIG. 67 is an expanded view of the circuit diagram in FIG. 66 illustrating a MOSFET device to replace a transistor forming one aspect of this disclosure.

With reference to FIG. 66, an adapted version of the chemical switch built to detect significantly more sensitive chemical reactions and the smaller associated potential build up from them is illustrated. In this embodiment, the circuit's sensitivity may be altered by changing the value of the resistor labeled Rg. It is also possible to vary the gain experienced by the transistor by changing the values of R2. This design is currently set for a gain of approximately 600. Turning to FIG. 67, FIG. 67 illustrates the same chemical switch shown in FIG. 66, but a MOSFET device replaces the transistor to allow binary switching effect, i.e., on/off for extremely small and sensitive voltages. Thus, the type of switch may depend on the transistor type used.

FIG. 66 shows the more sensitive circuit design for smaller voltage build ups, which acts as an open circuit for the sensor 20' due to the nature of opamps not using a current at the positive and negative inputs. This allows for the small charge build up to be maintained, which, in turn, activates the switch. If a simple NPN transistor is used (as shown in FIG. 66), until the point of saturation, the switch will gradually increase in current flow (analogous to a dimmer switch). Again, changing the value of Rg increases the sensitivity of the chemical sensor, which results in an increased gain. As discussed above, a MOSFET device may be substituted such that the switch acts a binary operating switch (analogous to a regular on off switch).

Figure 64:
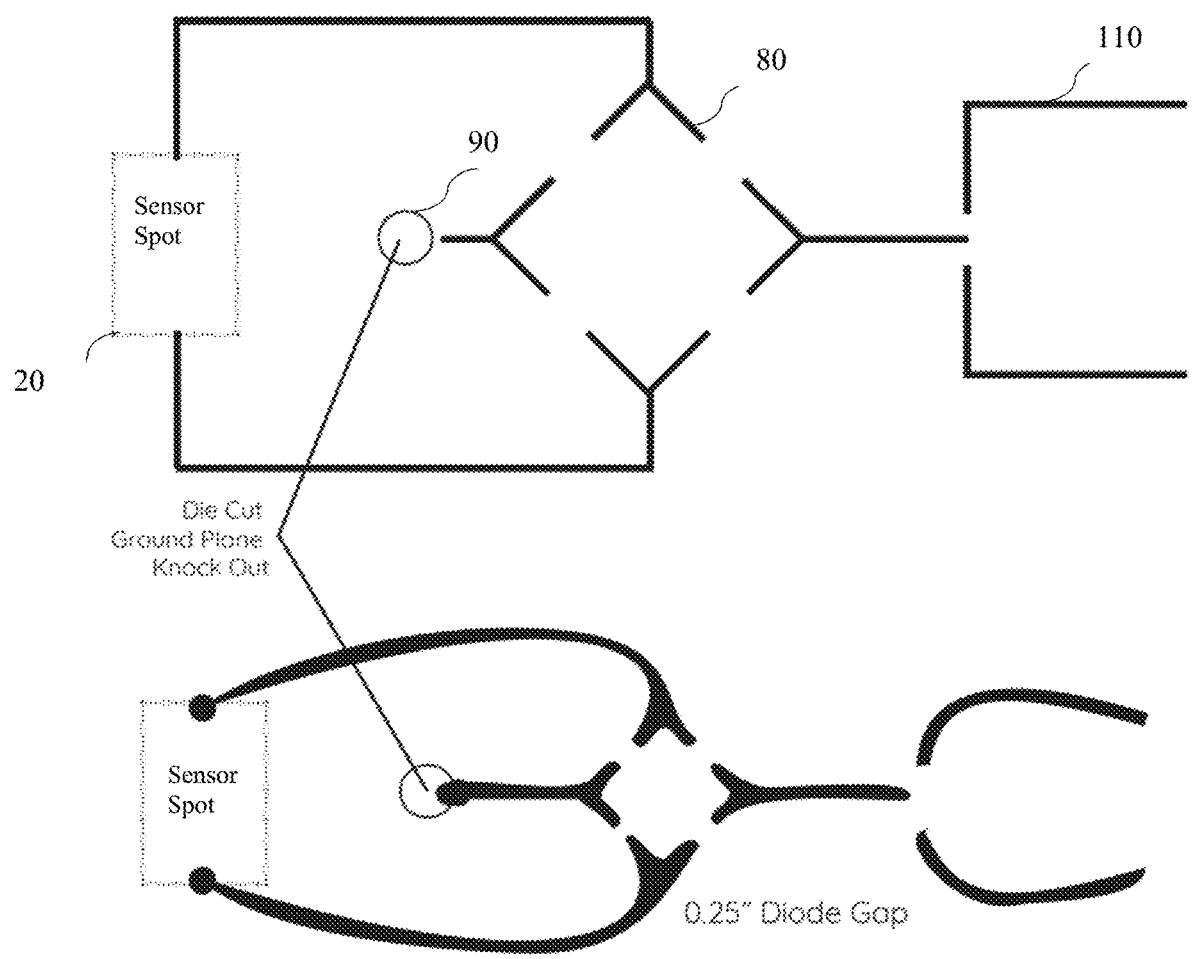
FIG. 64 is a paper printed circuit setup of the sensor switch forming one aspect of this disclosure.

Turning to FIG. 64, a print-out design for a paper printed circuit set up is illustrated. It should be appreciated that the range of designs is not limited to the structure shown in FIG. 64 and potential influential components may be added. Additionally, these components may be wired directly and not include a printed circuit. In the illustrated embodiment, a 0.25" diode gap is provided for the diodes, but other dimensions are contemplated for use with A/D converter.

In use, the freshness sensor device 10 needs to undergo a form of chemical activation. On interacting with some specific or general external influence, the sensor 20' is able to gain charge. A charge build up is able to induce a current through the alternating to direct current circuit 80 which, in turn, generates a buildup of electrons (or holes, depending on the arrangement of the alternating to direct current) then builds up at the base allowing for a current to flow from the collector to the emitter pins. This would be the on state of the switch. If no charge is built up in the sensor, then this cannot occur and the switch is off.

Again, the sensor is activated with the introduction of the external stimulus such that the sensor(s) generates a charge (directly or indirectly) within the device upon activation. For a chemical sensor (for detection of TVB-Ns as a specific but non-limiting example), the emission of the chemical being detected requires a small chemical reaction upon the surface of the sensor, which is mediated by either a chemical coating or a naturally occurring chemical deposition (such as the buildup of a moisture layer caused by the hydrophilic nature of the substrate being used, more specifically Whatman Cellulose Paper) as discussed above.

As detailed above, the chemical reaction generates positive and negative charge carriers that, over a short period of time, collect at the reciprocal charge electrodes in the sensor 20 (positive charges are attracted to the anode and negative charges to the cathode). As the charge builds up, the electrodes become polarized such that the polarized electrodes draw an external current through the attraction of a non-Faradaic process. Again, other chemical sensors may draw an external current through the application of a Faradaic process.

For TVB-N detection, a non-Faradaic process is used to generate a measurable resistance change similar to how piezoelectric materials work under an external pressure. As such, a piezoelectric material may replace the chemical sensor principally being described here, although these designs are not limited to either type of sensor. It should be noted that all the sensors described within this next section are analogous and interchangeable and not limited to chemical, thermal or piezoelectric sensors.

Figure 68:
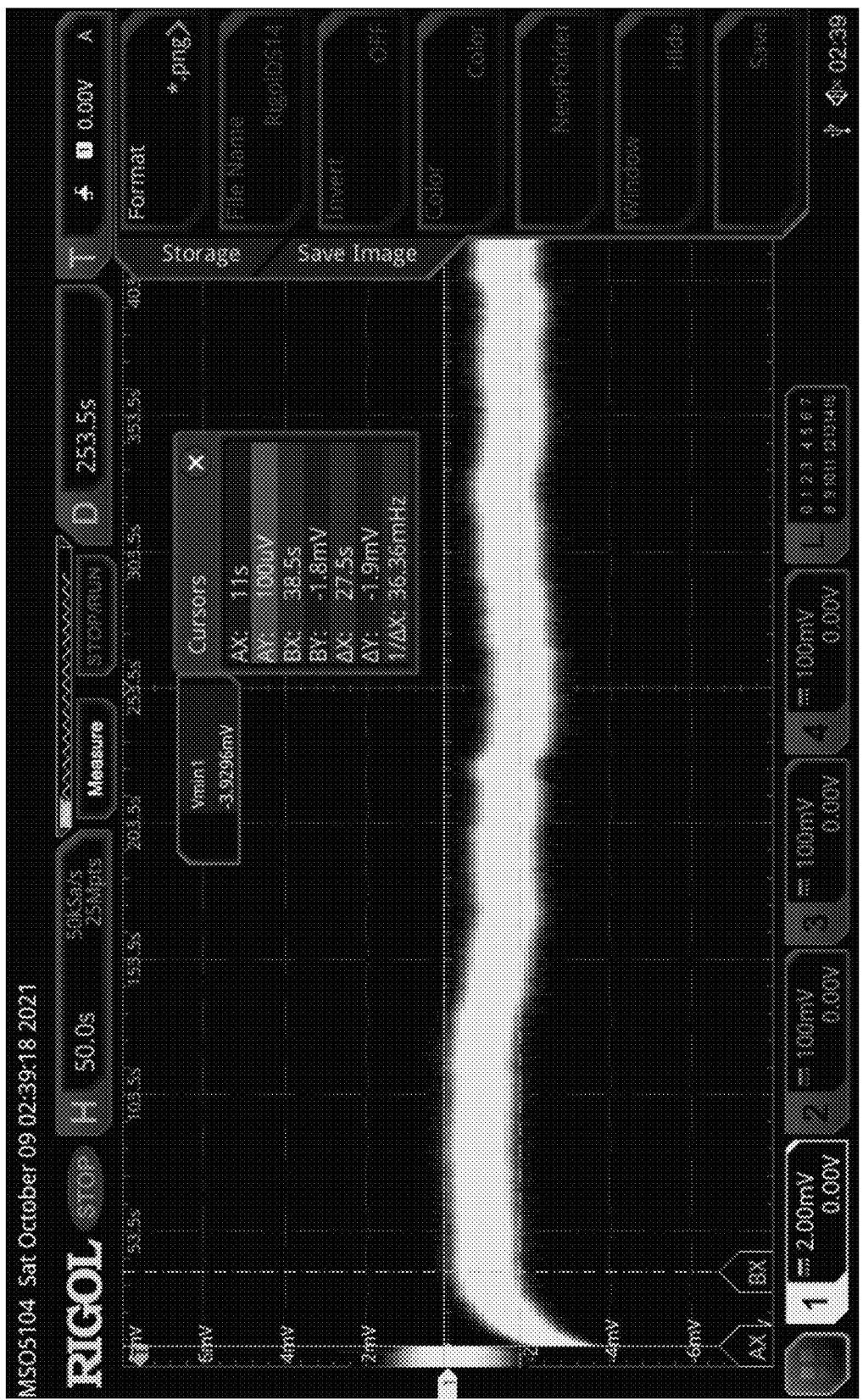
FIG. 68 is an example of 1 PPM being detected on a chemical switch sensor forming one aspect of this disclosure.
Figure 69:
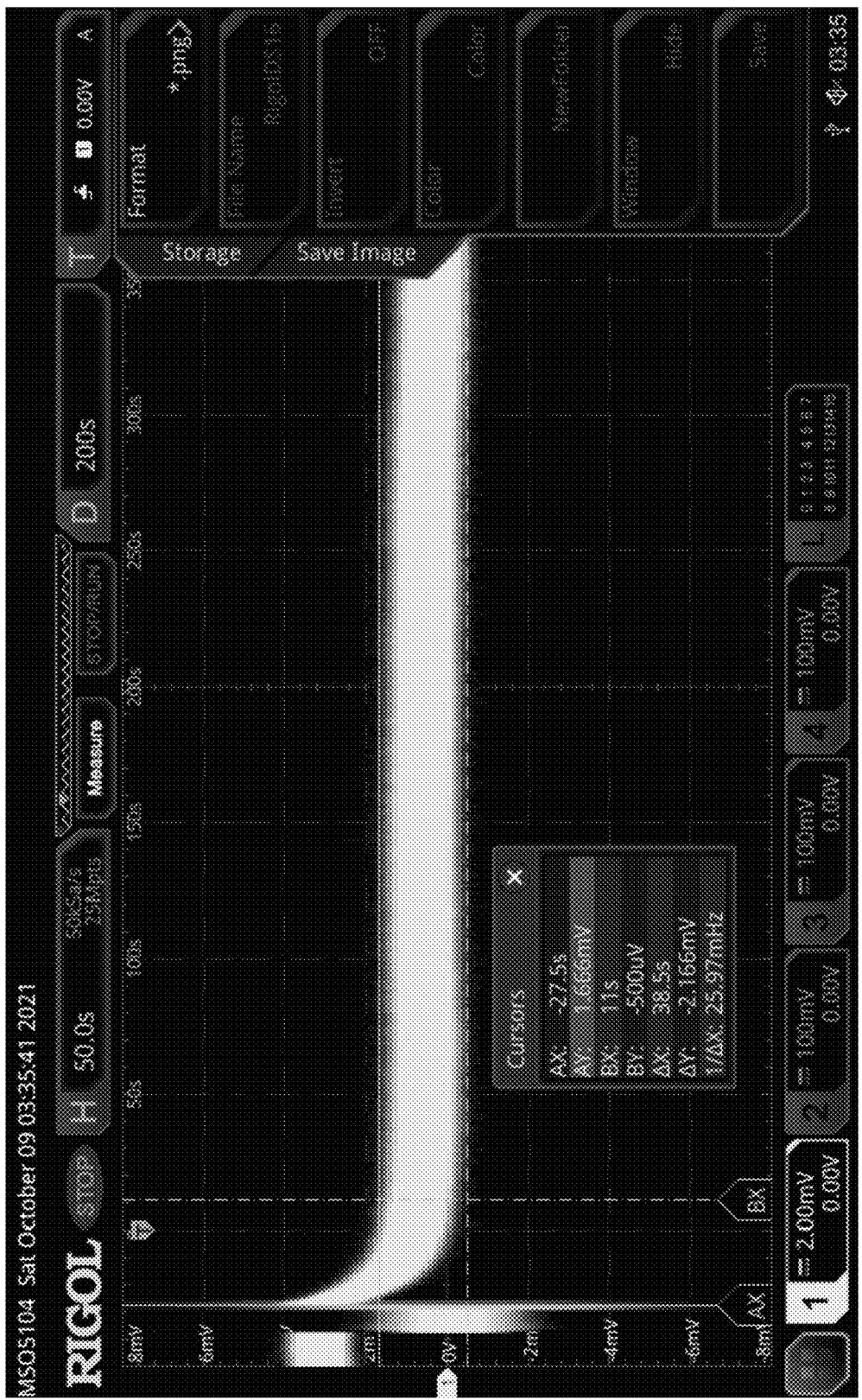
FIG. 69 is an example of 5 PPM being detected on a chemical switch sensor forming one aspect of this disclosure.
Figure 70:
FIG. 70 is an example of 25 PPM being detected on a chemical switch sensor forming one aspect of this disclosure.

Turning to FIGS. 68-70, these figures illustrate the sensors sustaining a small voltage (depending on the chemical concentration, results have been from 1-5 mV ranging from 1-25 ppm of ammonia). Specifically, FIGS. 68 and 70 illustrates examples of 1 PPM and 5 PPM, respectively, being detected on the sensor, while the baseline levels out at approximately 1 mV and maintained for the duration of the test and the concentration being left for twenty-four hours to accumulate a charge. In FIG. 70, the voltage experienced across the sensor 20' from a 25 PPM ammonia concentration that is left for twenty-four hours to accumulate and the voltage being maintained at ±7 mV for as long as the sensor is activated.

The sustained voltage is attributed to the constant chemical reaction and electrical potential build up at the electrodes. This is also informed by the sudden potential discharge that is experienced by the device upon activation of the oscilloscope in these figures. Simplified, if the sensor is in an open circuit, the charges build up at the electrodes. Then when the circuit is connected/completed, a rapid discharge occurs until the system reaches equilibration. This can also be observed in FIGS. 68 and 70 as evidenced by the series of wiggles or bumps in the voltage across the sensor electrodes.

Figure 71:
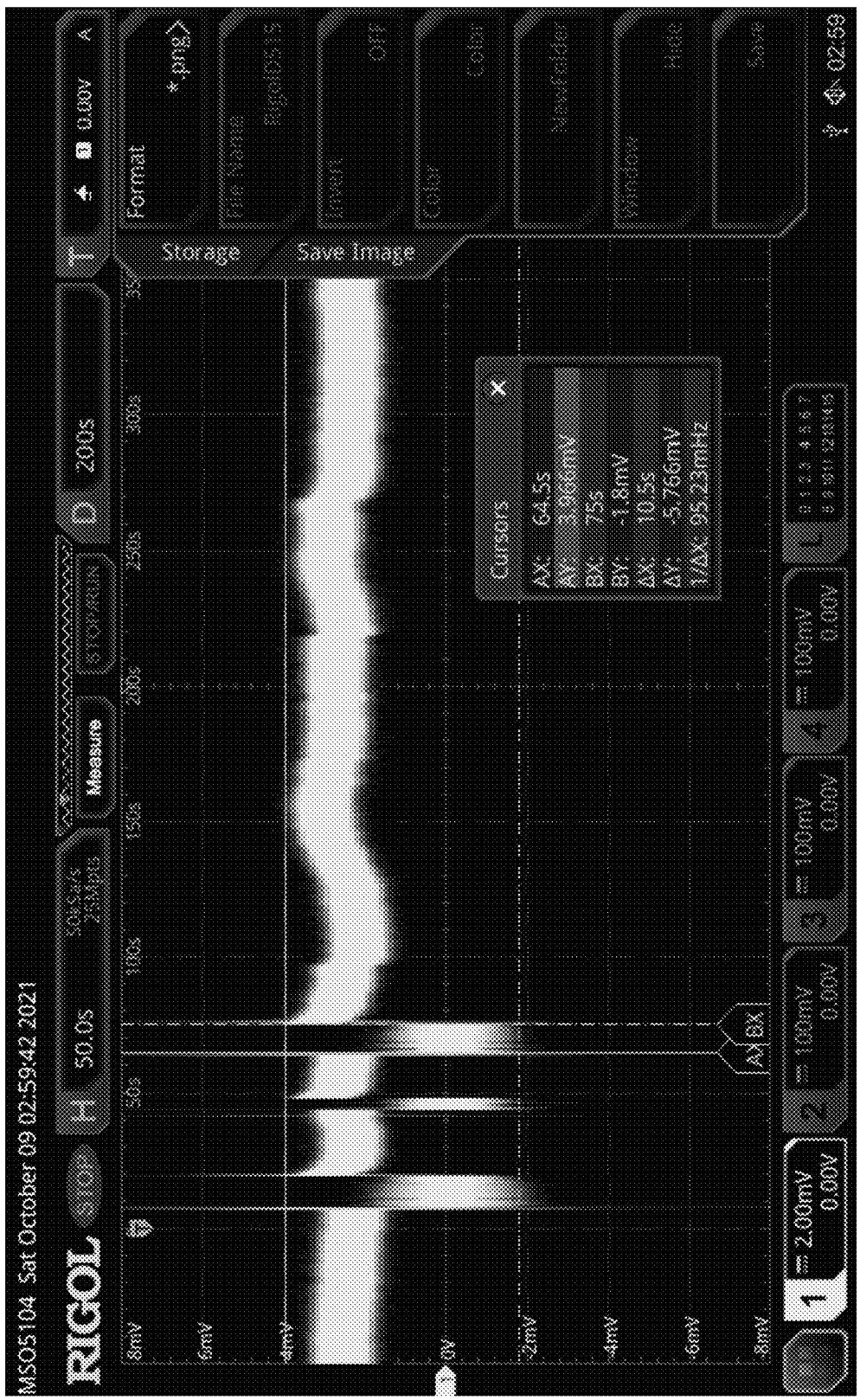
FIG. 71 illustrates a chemical sensor being activated and deactivated within a circuit showing a rapid build-up of charge and discharge as the sensor's electrodes attempt to reach equilibrium at 1 PPM forming one aspect of this disclosure.
Figure 72:
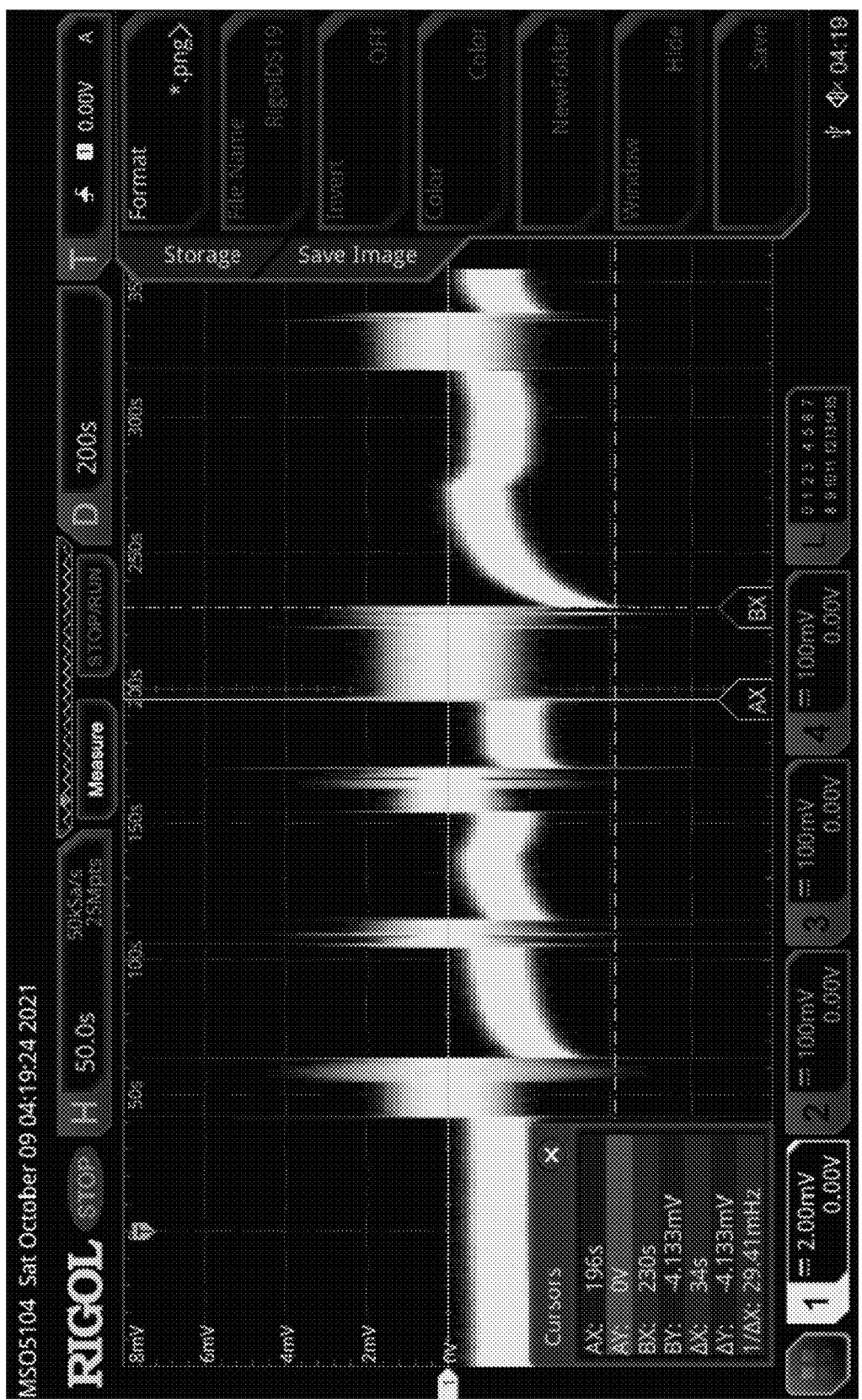
FIG. 72 illustrates a chemical sensor being activated and deactivated within a circuit showing a rapid build-up of charge and discharge as the sensor's electrodes attempt to reach equilibrium at 5 PPM forming one aspect of this disclosure.
Figure 73:
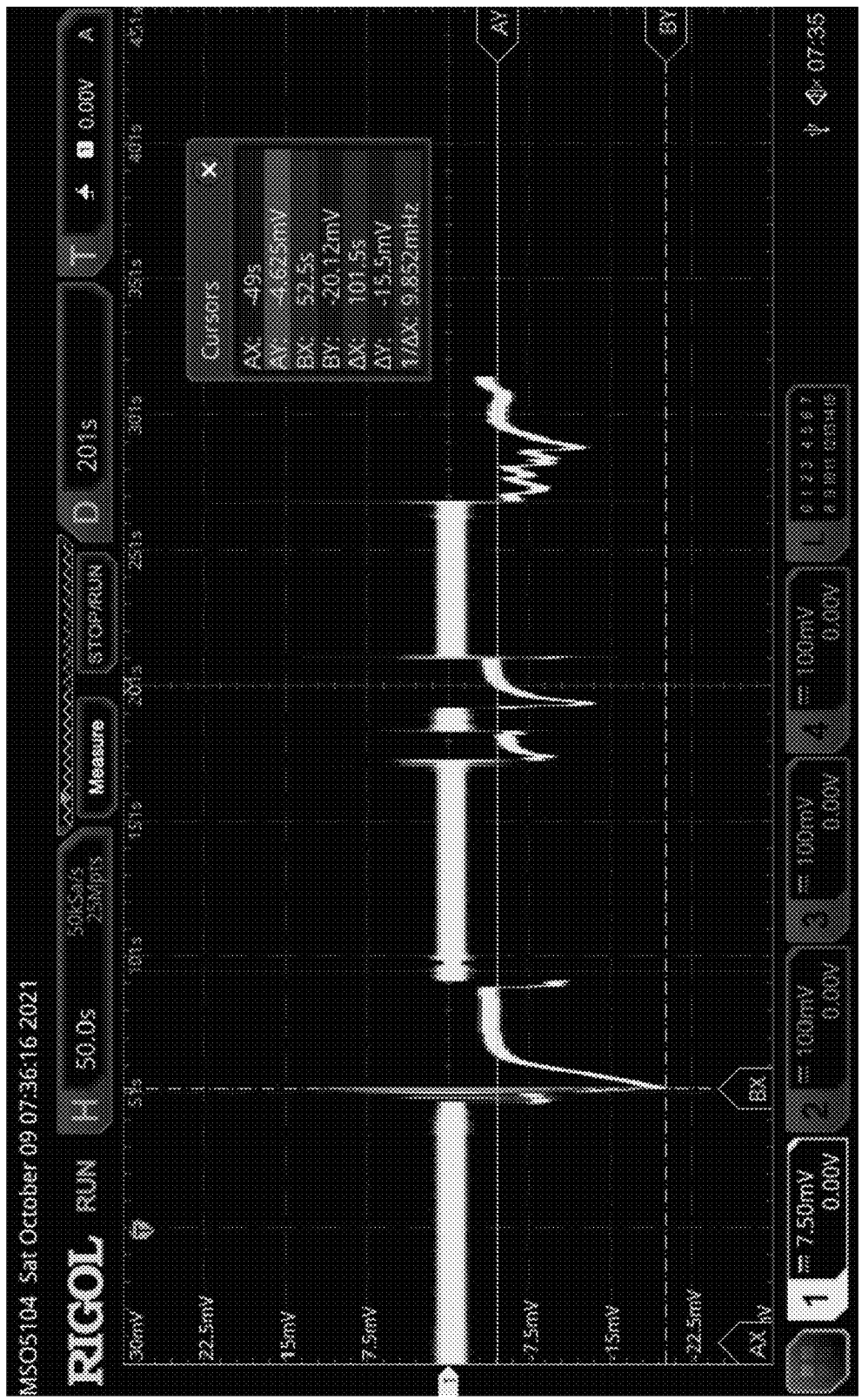
FIG. 73 illustrates a chemical sensor being activated and deactivated within a circuit showing a rapid build-up of charge and discharge as the sensor's electrodes attempt to reach equilibrium at 25 PPM forming one aspect of this disclosure.

With reference to FIGS. 71-73, these figures illustrate a chemical sensor being activated and deactivated within a circuit showing a rapid build-up of charge and discharge as the sensor's electrodes attempt to reach equilibrium at 1 PPM, 5 PPM and 25 PPM, respectively. The sensor 20' is able to rapidly equilibrate with low charge levels. These low charge levels are sustainable as they represent the reaction occurring on the sensor 20' and can maintain so long as the chemical components are in the environment. As a result, the switch operates both in a passive sense (where activation occurs when an external trigger tests the switches' state) and an active sense (where the sensors circuit is connected via a constant power supply).

Since this system requires a form of chemical detection that results in a voltage potential build up, this switch is capable of working at low voltage changes (through the application of the opamp) or high-level voltage changes (above 0.7 Volts will not require the application of the opamp and the original switch is applicable). However, the opamp may be used with higher voltage potentials, but too high a voltage damage the transistor. The effects of the charge/voltage build up from a chemical reaction that is detected must be contemplated before applying the chemical switch.

Table 1 shows the various decrease rates of the sensor switch and the baseline that is generated from the equilibrated reactional process, i.e., voltage discharge responses of different chemical PPM's. The increase in PPM shows direct correlation with the stabilized base lines minimal voltages, time to fully charge, peak voltage and time to reach baseline voltage. All of these effects agree with the sensor's ability to create a charge build up and maintain the charge based on the ongoing reaction with the chemical its detecting.

TABLE 1

| Ammonia Concentration | Time to baseline voltage | Baseline voltage (High) | Baseline voltage (Low) | Peak Voltage | Time to Full Charge (Approximated) |
|---|---|---|---|---|---|
| 1 ppm | 27.5 seconds | −1.8 mV | 100 uV | −3.9296 mV | 10.5 seconds |
| 5 ppm | 38.5 seconds | 1.666 mV | −500 uV | 4.2868 mV | 34 seconds |
| 25 ppm | 125 seconds | −6.25 mV | −4.625 mV | −21.795 mV | 101.5 seconds |

Figure 65A:
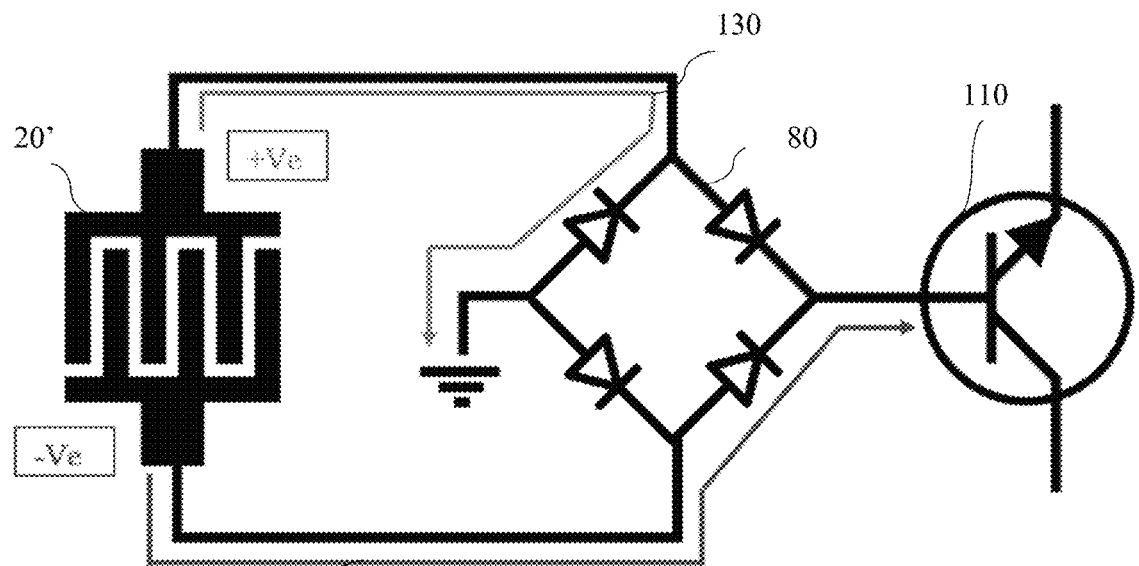
FIGS. 65A and 65B are circuit diagrams of the sensor switch forming one aspect of this disclosure.
Figure 65B:
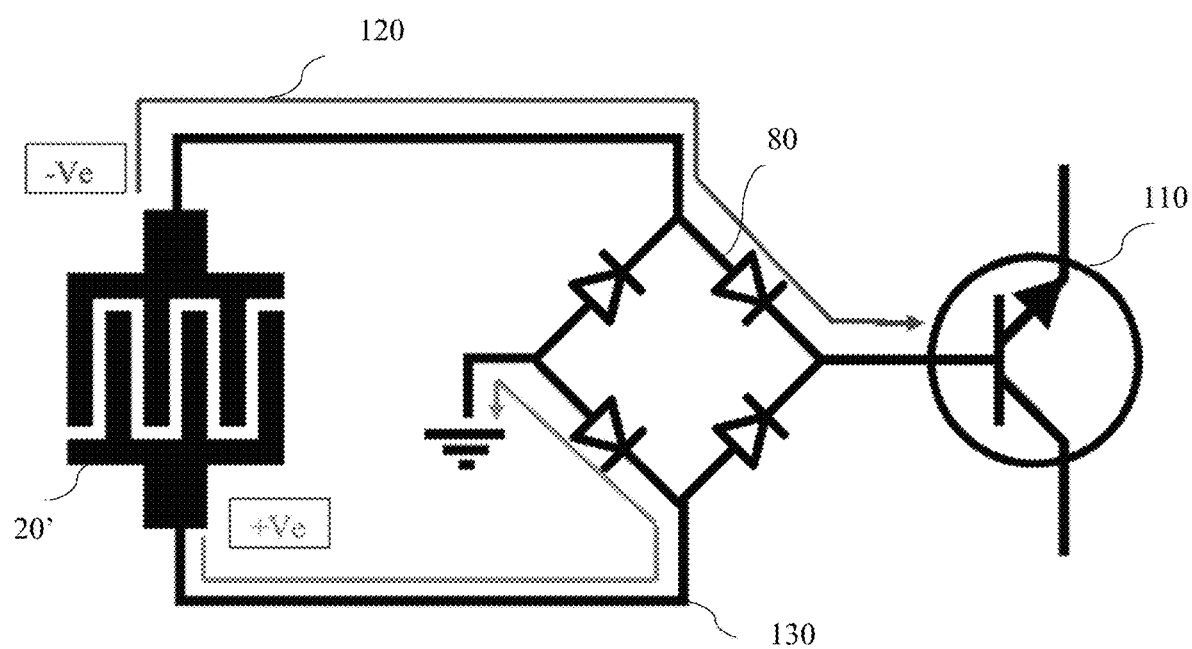

Additionally, it is highlighted that the sensor is neither initially polarized, nor does it require a specific polarization to activate the switch as shown in FIGS. 65A and 65B. The lines 120 in FIGS. 65A and 65B denote the direction of travel by the electrons, while the other lines 130 denote the direction of travel of the positively charged particles or holes.

The application of the AC rectifier circuit ensures electrical potential is correctly directed to the transistor 100. The ideal diode amplifier circuit amplifies the potential in order to activate the transistor for smaller voltages or more sensitive reactions. The circuit operates by flipping a chemical switch on (or off depending on the type of transistor). If the opposite potential is required, it is possible to re-direct the potential to correctly effect an alternate style of transistor (PNP instead of NPN for example). Additionally, it should be noted that the use of an opamp will result in a current being exude to the transistor. Again, for this switch, a small current will be passable from the sensor to the transistor without the aid of the opamp. This small current activates the transistor completing the switching circuit.

The sensor switching mechanism offers a number of advantages over other sensor devices. For example, the sensors have the ability to retain charge, irrespective of external potential difference. Indeed, the electrode poles in the sensors will flip, but overall charge will remain the same. Unlike the sensor switching mechanism disclosed herein, other devices require a predefined polarity and charge carrier direction to activate an additional switching function or logic process that will then operate.

Turning back to FIG. 3, in another embodiment, a discrete RFID/Zigbee/Bluetooth (aerial) and/or IC chip 40 with included or separate A/D converter circuit 80 is utilized with the sensor 20 and the antenna 30. In this approach, the antenna 30, aerial/IC chip 40, and A/D circuit 80 act as one general cluster of components with consistent behavior. The sensor 20 then varies depending on Amine and TVB-N content of the environment being sensed. In one embodiment, an inductive RFID/NFC external signal is provided, wherein the antenna 30 collects energy and activates the aerial or IC chip 40 which reads the sensor data. Thereafter, the antenna 30 broadcasts a unique identifier (specific to a particular perishable item, such as a specific serial number to distinguish devices/tags for a particular item to another), pulse tests a signal through the sensor 20 and detects a voltage drop from the sensor 20. The A/D converter circuit 80 interprets the voltage drop from analog into digital form data, and transmits the digital data to the external receiver. In other words, the A/D converter circuit is configured to convert the data acquired by the sensor (typically in analog form) into digital values.

The receiver may be a mobile phone, tablet or other computing device, which may have an input unit, a central processing unit, a memory or storage unit and an output unit. The receiver applies a freshness algorithm to the digital form data in order to provide a freshness interpretation value via a software application running on the receiver. In some embodiments, by making use of such a sensor 20 and delinking the function of the sensor from the function of the antenna 30, it allows any failures in the sensing circuit to not prevent the identity capability from functioning.

Figure 4:
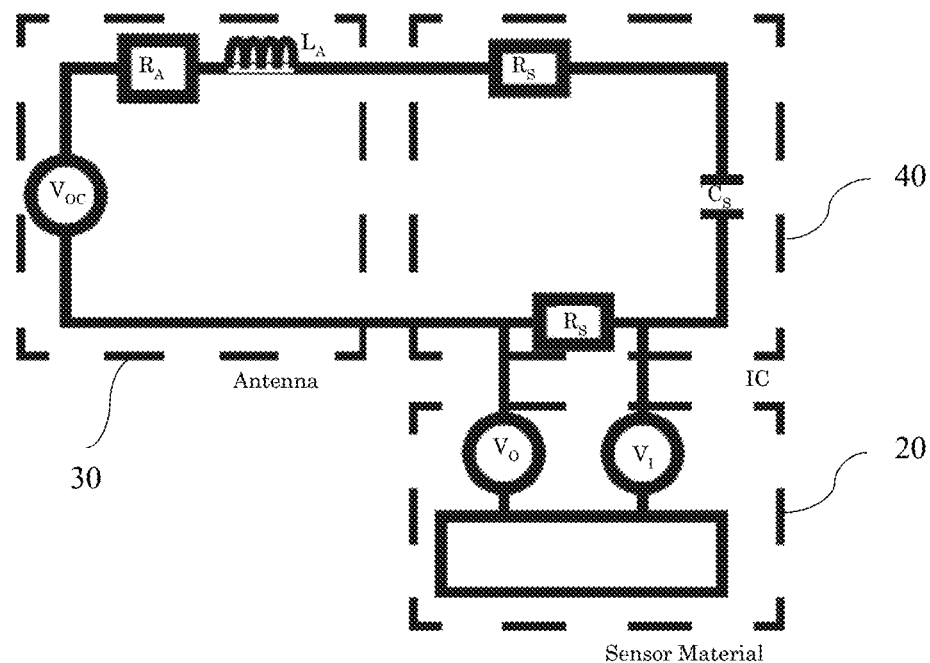
FIG. 4 is a circuit diagram for a freshness sensor device designated a voltage drop binary presence sensor forming one aspect of this disclosure.

In the approach illustrated in FIG. 4, an antenna 30, an aerial or IC chip 40, and a sensor 20 is provided, but the sensor value is read as a binary value because it lacks an A/D converter circuit 80. This approach is similar to the approach in FIG. 3, but the A/D requirements are reduced. Consistent with an existing inductive RFID/NFC external signal, the antenna 30 collects energy, activates the aerial chip 40, broadcasts a unique identifier, pulse tests a signal through the sensor 20, determines continuity data (binary and dependent on Amine and TVB-N content detected), and transmits the continuity data to a receiver. Again, the receiver takes this data and provides a freshness interpretation value via a software application running on the receiver. In this approach, the stock-keeping function is maintained even in case of sensor faults. This approach is designed to only detect one concentration of Amine and TVB-N, which indicates whether the perishable item is fresh or not.

Figure 5:
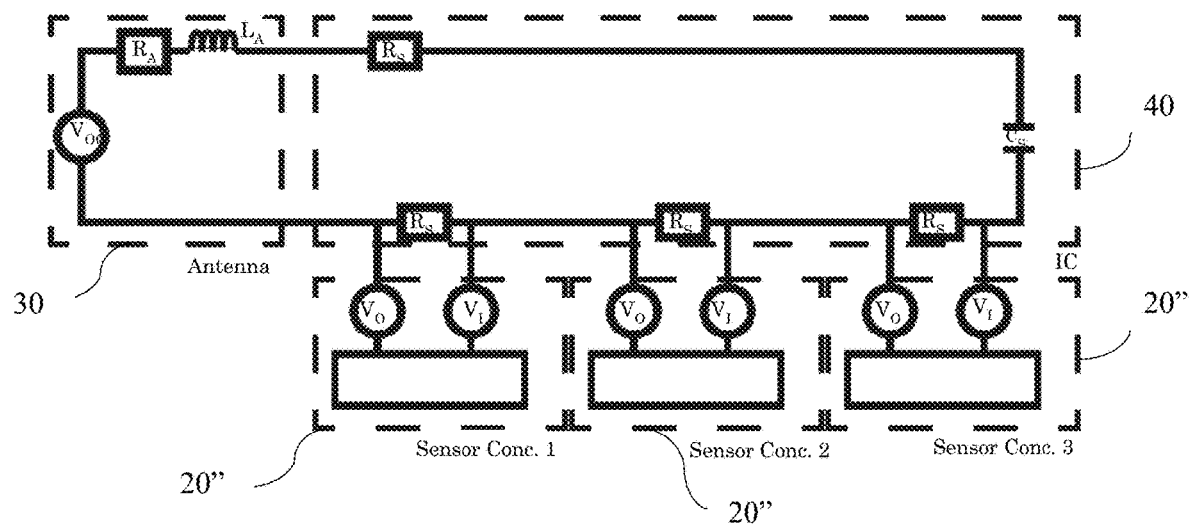
FIG. 5 is a circuit diagram for a freshness sensor device designated a voltage drop binary presence ladder type sensor forming one aspect of this disclosure.
Figure 50:
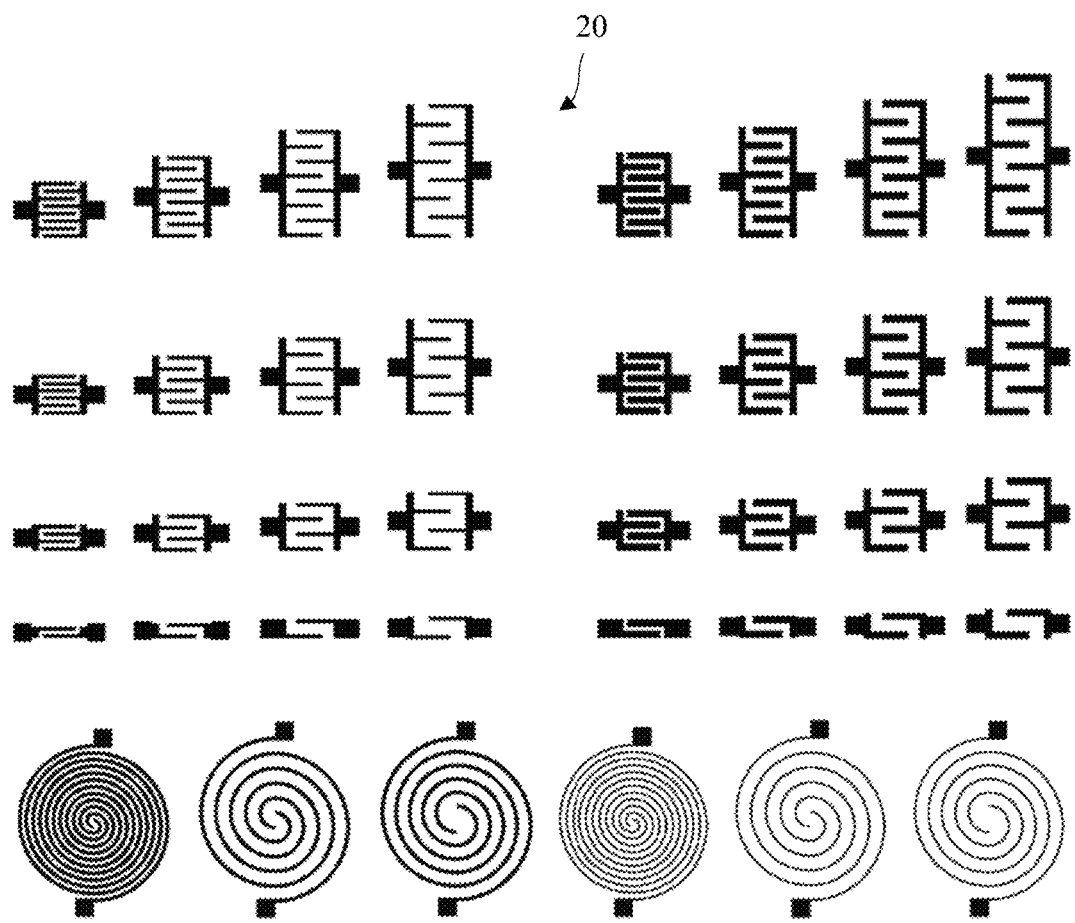
FIG. 50 is a schematic diagram illustrating various sensor designs with variations in sensor length, width and thickness forming one aspect of this disclosure.

With reference to the approach illustrated in FIG. 5, the third approach (detailed above) is extended with the addition of multiple binary sensors 20″, each tuned to a different Amine and TVB-N concentration. In the illustrated embodiment, three binary sensors 20″ are shown, but it should be appreciated that a different number of sensors may be utilized. This approach avoids the added complexity of the A/D converter circuit 80. Further, the variety of concentrations sensed are based on the differing geometries of each sensor. For example, the sensitivity of each sensor may be based on the whether it is linear or spiral (as shown in FIG. 50), the electrode gap within the sensor, or other factors related to the dimensions and shape of the sensor.

Figure 6:
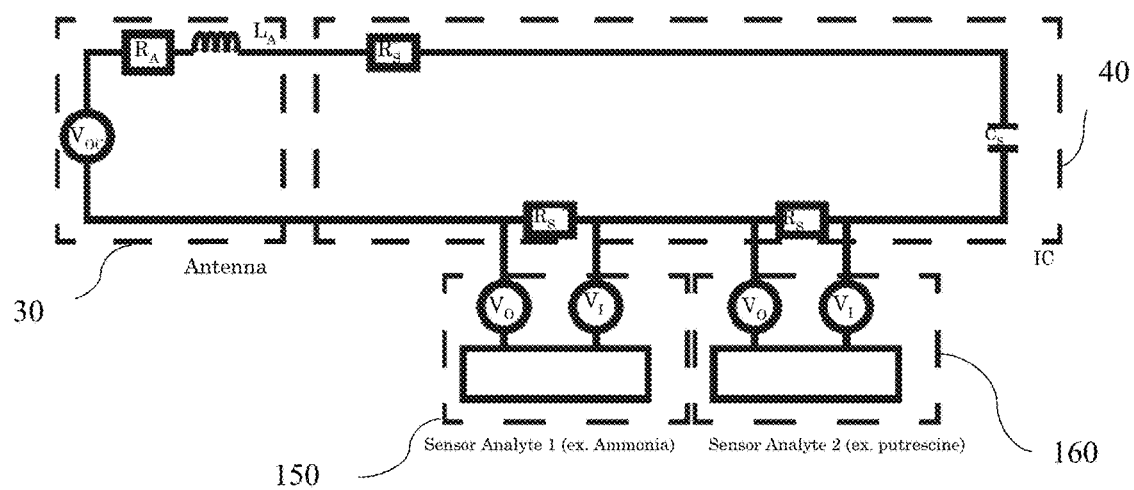
FIG. 6 is a circuit diagram for a freshness sensor device including multiple sensors for detecting different analytes forming one aspect of this disclosure.

Turning to FIG. 6, the fourth approach is extended with the addition of multiple binary chemical sensors 150, 160 that are designed to identify a different chemical. For example, the first sensor 150 is configured to detect a first analyte, such as ammonia, while the second sensor 160 is configured to detect a second analyte, such as putrescine. Again, this approach avoids the added complexity of an A/D converter circuit 80. Moreover, the different sensors used is based on the differing byproducts given off by microbes and bacteria or perishable good during the decay process. Examples of these byproducts, including but are not limited to cadaverine, putrescine and the like. The presence of these byproducts at a given concentration triggers an affirmative binary signal which is communicated over the antenna/radio 30 to the external receiver. The receiver then leverages the results of the binary sensors 20 to provide a freshness interpretation value via a software application running on the receiver.

Figure 7:
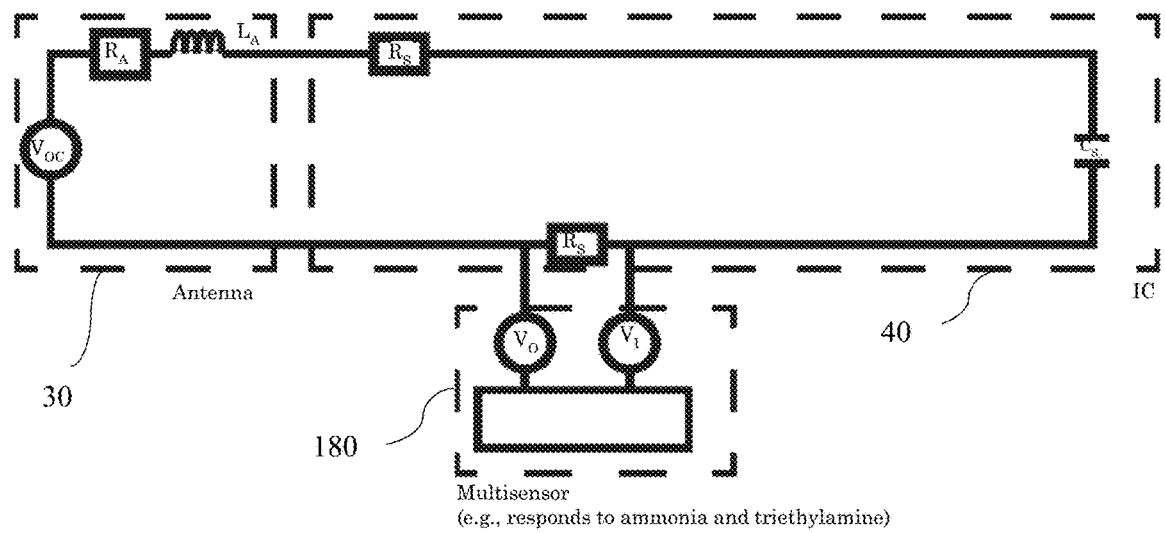
FIG. 7 is a circuit diagram for a freshness sensor device including a multi-analyte presence type sensor forming one aspect of this disclosure.

As shown in FIG. 7, this approach extends the third and fifth approach (discussed above), by utilizing a multi-sensor 180. Again, the variety of sensors used is based on the differing byproducts given off by microbes and bacteria during the decay process, which include cadaverine, putrescine and the like. For example, in the illustrated embodiment, the multi-sensor 180 is able to detect both ammonia and trimethylamine. Once detected, the IC 40 is configured to process/convert a signal related to the detected chemical(s) from the sensor 20 into a digital signal, which is reported to a receiver over the antenna 30. A freshness value is interpreted using calculations via the software application to provide a user-readable value of the freshness of the perishable item.

Regardless of which circuit approach is utilized, the freshness sensor device 10 is designed to leverage the increase of analytes to gauge freshness of the particular perishable item. Additionally, each approach leverages an external energy source to energize the IC and enable radio communication via the antenna 30 back to a reading device that provides information or lack thereof to determine the state of freshness of the perishable item. Generally, each approach uses inductive energy to power the IC, i.e., RFID and NFC. However, none of the approaches are limited to this format and can be easily changed depending on the environment. Alternative methods of power include harvesting from different radio types, solar, heat, and kinetic/piezoelectric are contemplated. Typically, the radio communication leverages standard communication methods and protocols (RFID, NFC, Zigbee, Thread, 802.15.4, Bluetooth, etc.) and functions as such.

Figure 8:
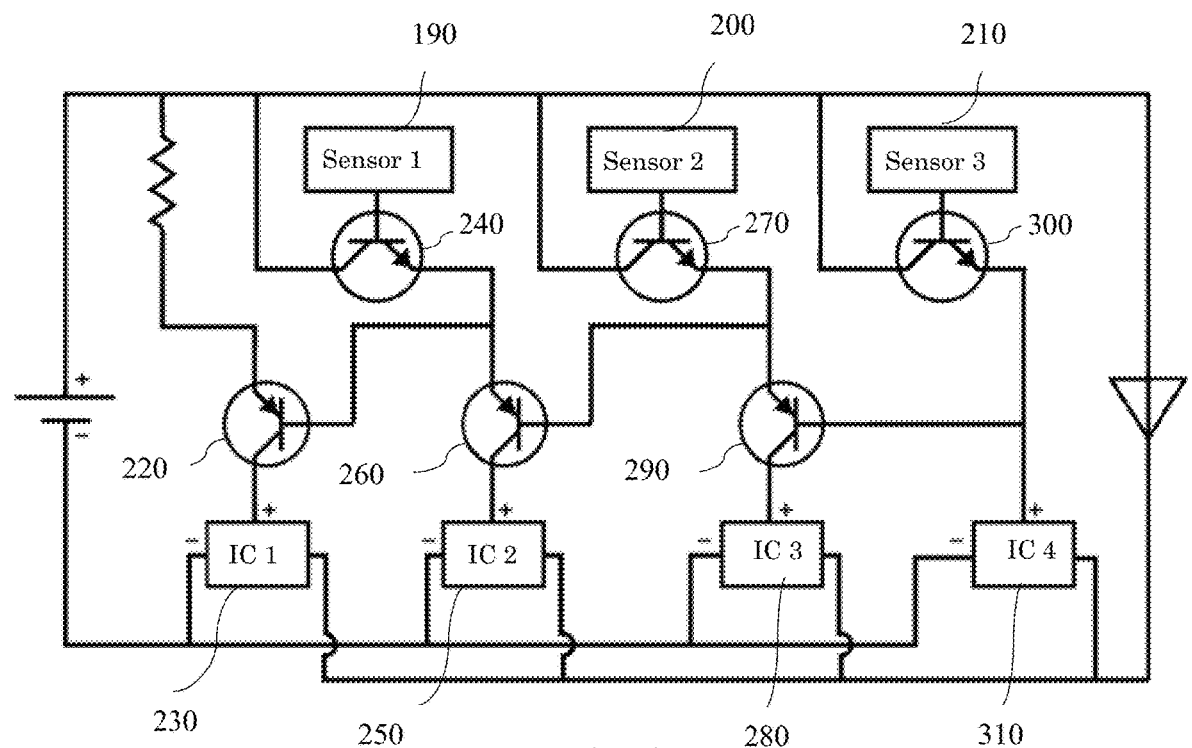
FIG. 8 is a schematic diagram of a freshness sensor device forming one aspect of this disclosure.

Turning to FIG. 8, a sensor switch utilizing a step-ladder design is illustrated. Each successive sensor is configured to require more of the detectable substance than its predecessor (indicated numerically) in order to activate, i.e., sensor 190 is more sensitive than sensor 200, which, in turn, is more sensitive than sensor 210. Because sensor 190 is the most sensitive, it will activate upon the smallest detection of the detectable substance.

Initially, prior to detection of any detectable substance, the sensors 190, 200 and 210 are not activated and the circuit operates via current flowing through the first transistor 220 and the first IC 230. When sensor 190 detects a pre-defined amount of the chemical under detection, the sensor 190 is activated. Upon activation, the sensor 190 then activates the corresponding transistor 240, which allows for the flow of current through towards the second IC 250. This current is then used to deactivate the first IC 230 through the application of an equivalent PNP transistor 220 that switches the first IC 230 off when current is applied to it. In other words, upon activation of sensor 190, the path to the first IC 230 is shorted out and the second IC 250 is activated.

Subsequently, sensor 200 becomes triggered by detection of a pre-defined amount of the chemical under detection. Upon activation, the sensor 200 activates the corresponding transistor 270, which allows for the flow of current through towards the third IC 280. This current is then used to deactivate the second IC 250 through the application of an equivalent PNP transistor 260 that switches the second IC 250 off when current is applied to it, i.e., the path to the second IC 250 is shorted out and the third IC 280 is activated. Sensor 210 operates in the same manner along with the corresponding transistor 300 and fourth IC 310, whereby upon activation of sensor 300, the path to the third IC 280 is shorted out and the fourth IC 310 is activated. It should be appreciated that more than three sensors may be utilized.

The step-ladder design illustrated in FIG. 8 also leads directly to another embodiment, wherein the application of multiple sensors are capable of detecting unique/more specific chemicals. For example, in the embodiment detailed above, each of the sensors detects the same detectable substance, i.e., TVB-N's, albeit each sensor is tuned to a different concentration of the detectable substance. In other embodiments, each additional sensor may be configured to identify other/different volatile organic compounds (VOC's), carbon dioxide ($CO_2$) variations and with the application of simple logic gates a series of circuit binary responses can be used to activate relevant IC signals. For example, a two sensor system detecting multiple two separate chemicals would require 4 IC signal options. Binary responses for a two chemical sensor detection system are shown below in Table 2:

TABLE 2

| Compound | IC response |
| --- | --- |
| None | IC 1 (normal response) |
| Chemical 1 | IC 2 (found Chemical 1) |
| Chemical 2 | IC 3 (found chemical 2) |
| Chemical 1 and 2 | IC 4 (Found both chemicals) |

Clearly, the number of ICs will increase in an $2^n$ order of complexity. Advantageously, the external application (given unique RFID ID's from the sensors) will be able to record multiple IDs with multiple chemical detectors to deliver a more holistic view of the detected environment. In other words, a sensor tag can detect one or more chemicals and relay that through an ever increasingly complex logic circuit, or each chemical can be assigned its own sensor tag (ladder or binary) and through the application of an RFID signal source and a receiver (i.e., a mobile phone), the passively charged tags can relay multiple environmental factors that are individually detected. Resistance changes in response to all or some of the following meat decay gasses include but are not limited to ammonia, cadaverine, putrescene, water, nitrogen and sulphur.

The detection of groups of chemicals may also be achieved by observing the resistance or some other form of data, including but not limited to ratio values or rates of change of resistance. These changes allows a matrix of possible reasons why the sensor has been activated to be developed. For example, if the resistance value decreases significantly, a TVB-N is most likely present. If the ratio calculations have a specific value above 0.5 and remains stable, then a VOC may be present. Using these variations, a matrix of rules may be developed to understand if a simple warning should be given, i.e., food is starting to spoil or a more explicit warning, i.e., eat at your own peril, which is dependent on the programming of the application. The raw data of these sensors is continuously sent to the receiver, such as a computing device or mobile phone over the radio or antenna 30, and the receiver applies a determined rule set via the software application to provide a human-readable freshness value.

Figure 9:
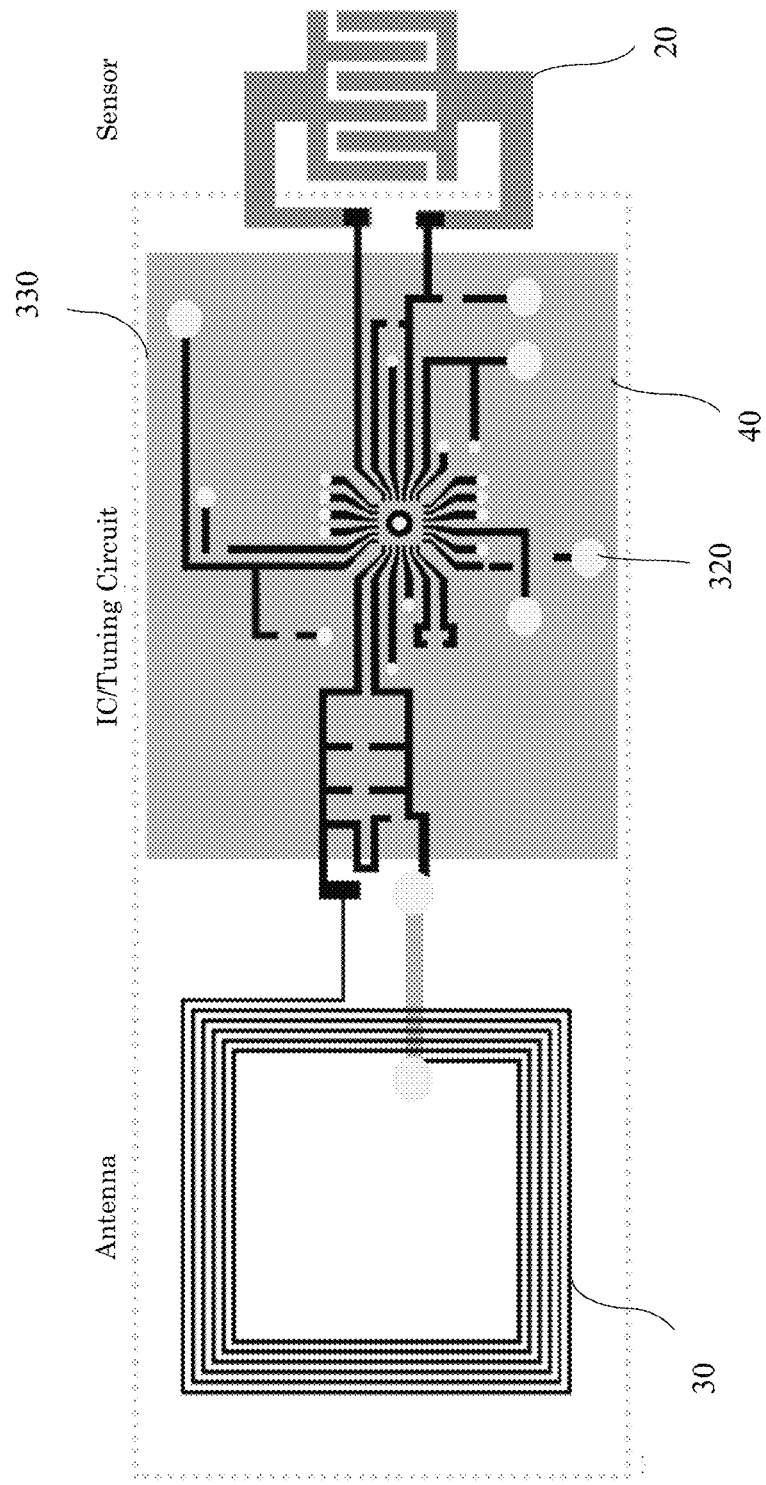
FIG. 9 is a component level printed sensor circuit of a completed IC forming one aspect of this disclosure.
Figure 10:
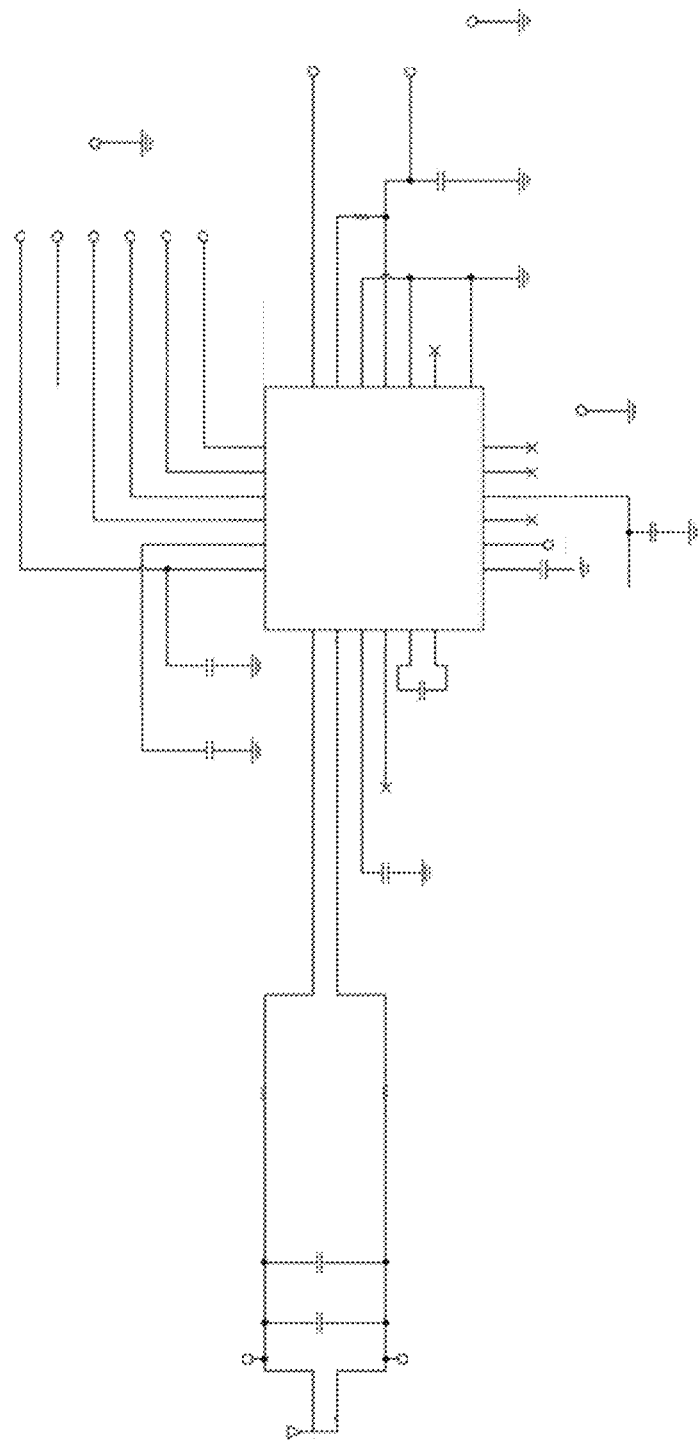
FIG. 10 is a component circuit diagram of the electrical components of the IC illustrated in FIG. 9 forming one aspect of this disclosure.

Turning to FIGS. 9-15, various different circuit variations and alterations for the freshness sensor device utilizing an analog to digital convert process are illustrated to show the capabilities of the print press process onto a substrate 330. In FIGS. 9 and 10, the individual component placed circuit is illustrated. The sensor 20 connects via electrically wiring through the ground plane to the NFC antenna 30. The circles 320 represent the connection to the rear side of the substrate 330.

Figure 11:
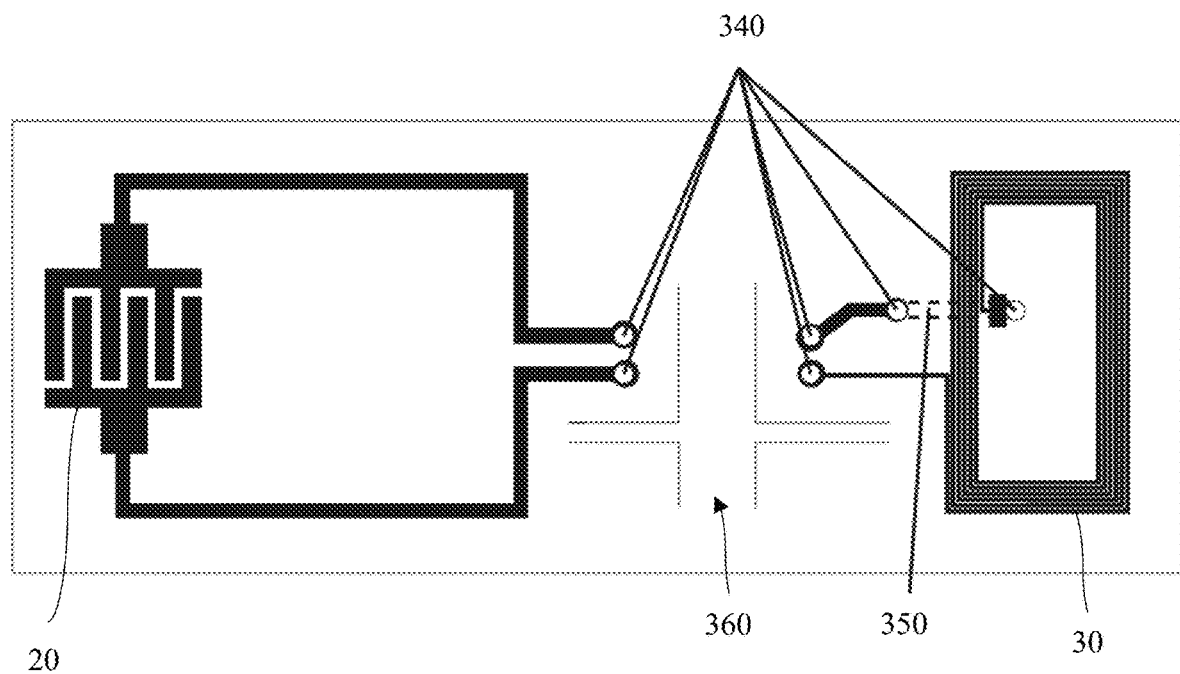
FIG. 11 is a component level printed sensor circuit having a self-contained IC forming one aspect of this disclosure.
Figure 12:
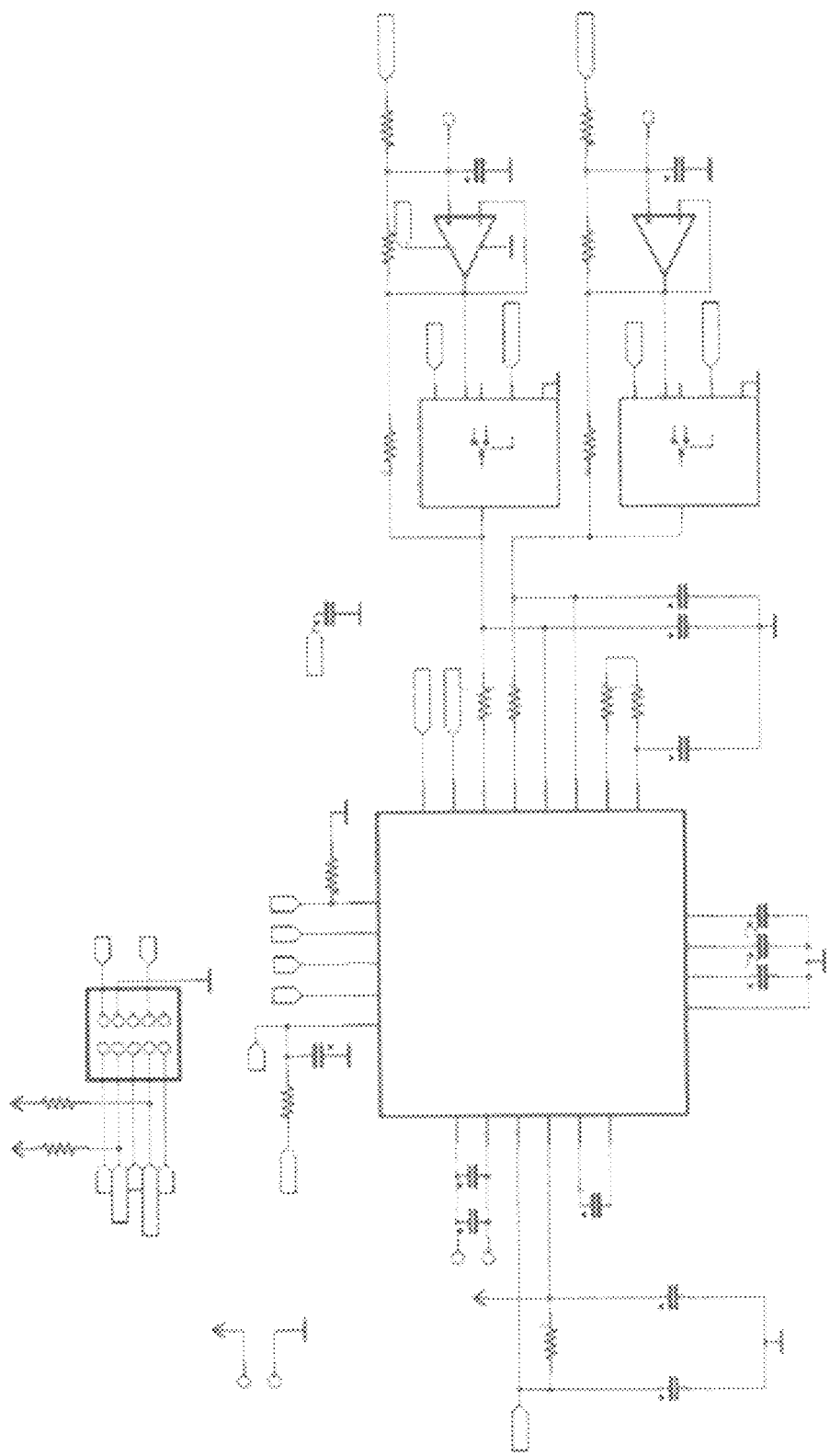
FIG. 12 is a component circuit diagram of the electrical components of the IC flex chip illustrated in FIG. 11 forming one aspect of this disclosure.

With respect to FIGS. 11 and 13-15, an internal IC is illustrated, while FIG. 12 illustrates the components of the self-contained IC applicable to these figures. Both the internal IC and the individual component placed circuit allow the freshness sensor device to detect and convert the resistance reading from the sensor to a digital signal. FIG. 11 illustrates a printed sensor circuit having a self-contained IC, i.e., the IC is located within an insert pocket 360. Silvering dots 340 may be positioned on the substrate via a rotary screen printing process. The silvering dots 340 are connected to the NFC antenna 30 via a backside connection 350. As with the previous designs, the digital signals are transferred to an external device, interpreted via the software application into a human-readable result.

Importantly, the internal IC circuit holds several advantages over the individual component, including the application of an A/D component, which is able to give a more varied response to the sensor's detection and activated state. Additional memory components can also be added to store more information on the freshness tag directly as well as the application of having multiple programmable signal responses (described in more detail below).

Figure 13:
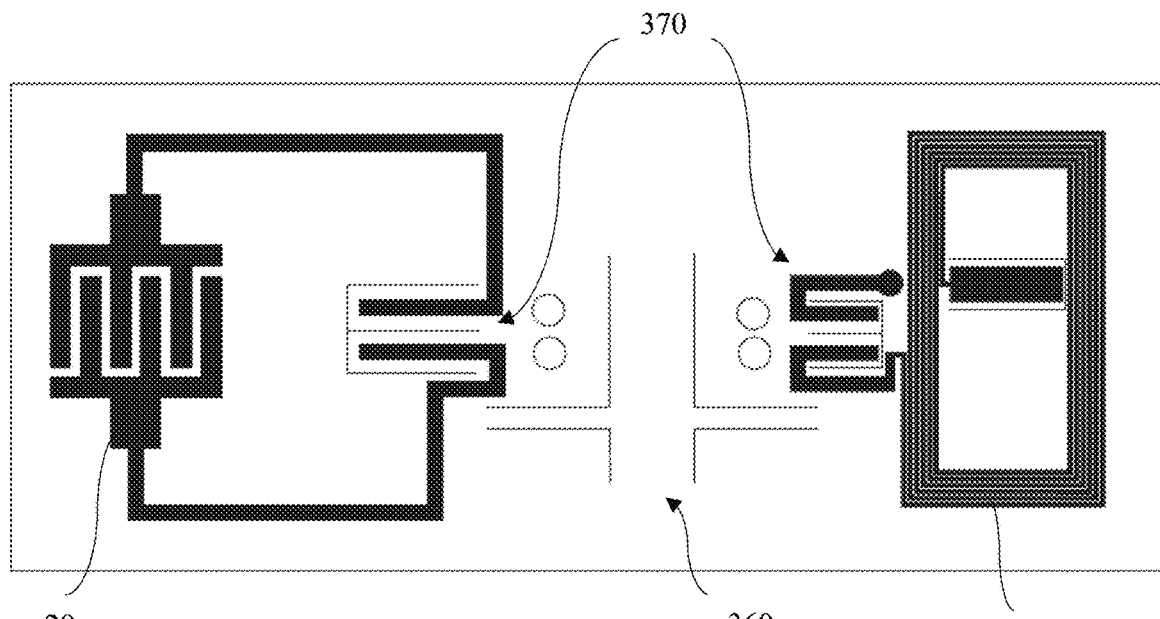
FIG. 13 is a component level printed sensor circuit of a completed IC having an insert pocket forming one aspect of this disclosure.
Figure 14:
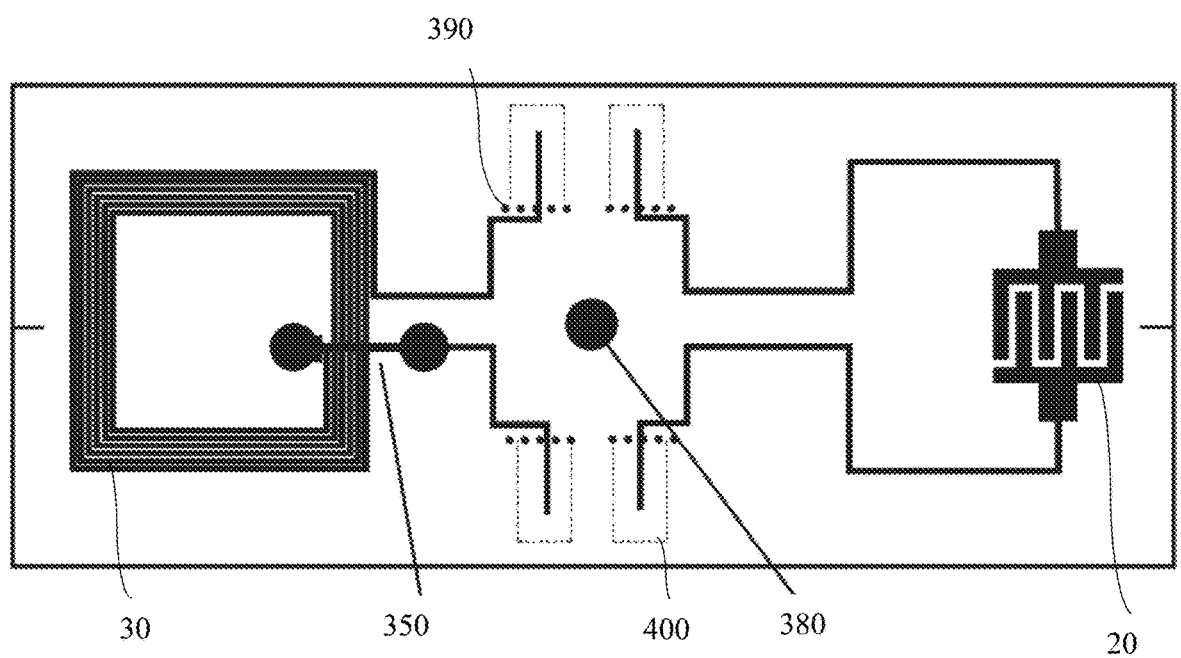
FIG. 14 is a component level printed sensor circuit of a self-contained IC having a foldable electrical connection forming one aspect of this disclosure.
Figure 15:
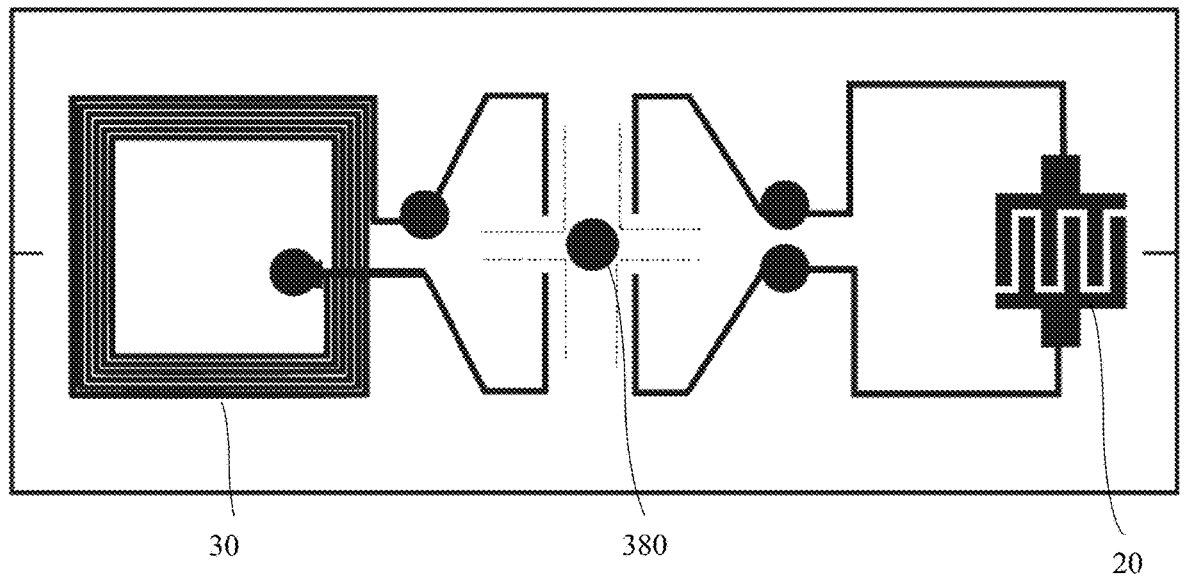
FIG. 15 is a component level printed sensor circuit of a completed IC forming one aspect of this disclosure.

Turning to FIG. 13, it shows an IC contained circuit having connection tabbing 370, which is partially cut out of the paper substrate to allow for physical looping out of the plane of the paper, i.e., it is folded upwards to connect to the IC. Similar to FIG. 13, FIG. 14 illustrates a foldable electrical connection along with the addition of a central ground plane 380 for a self-contained IC that is glued to the substrate 330. The substrate 330 includes fold lines 390 and cut lines 400 for the self-contained IC. FIG. 15 shows a circuit diagram having a cut in the paper substrate 330 that allow for the folding or bending of hot electrodes onto a component contained IC device.

Figure 16:
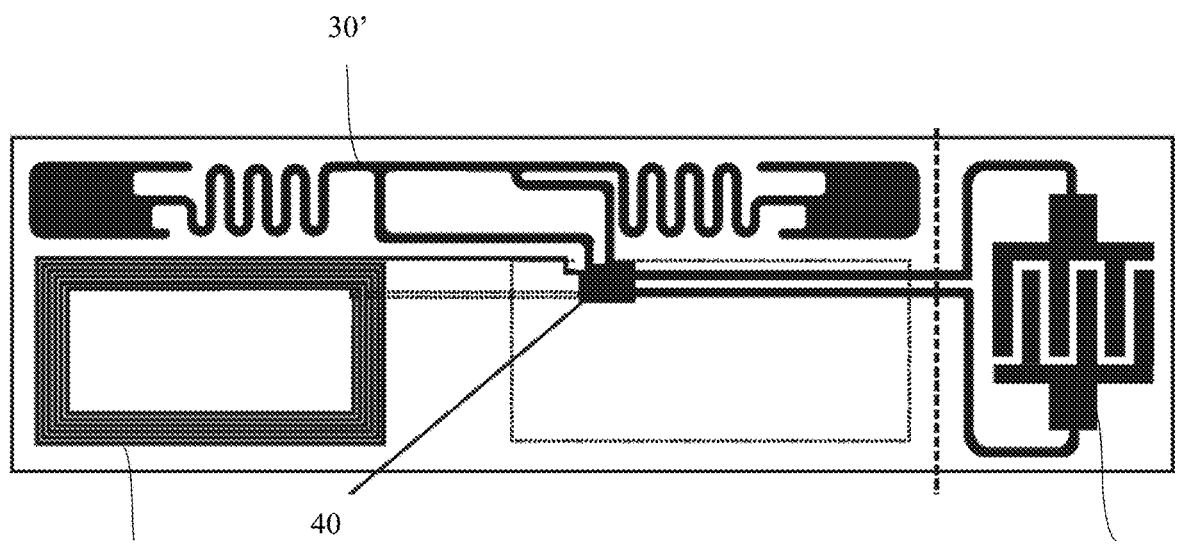
FIG. 16 is a dual antenna print design for responding to and/or making use of both NFC and RFID protocols forming one aspect of this disclosure.
Figure 17:
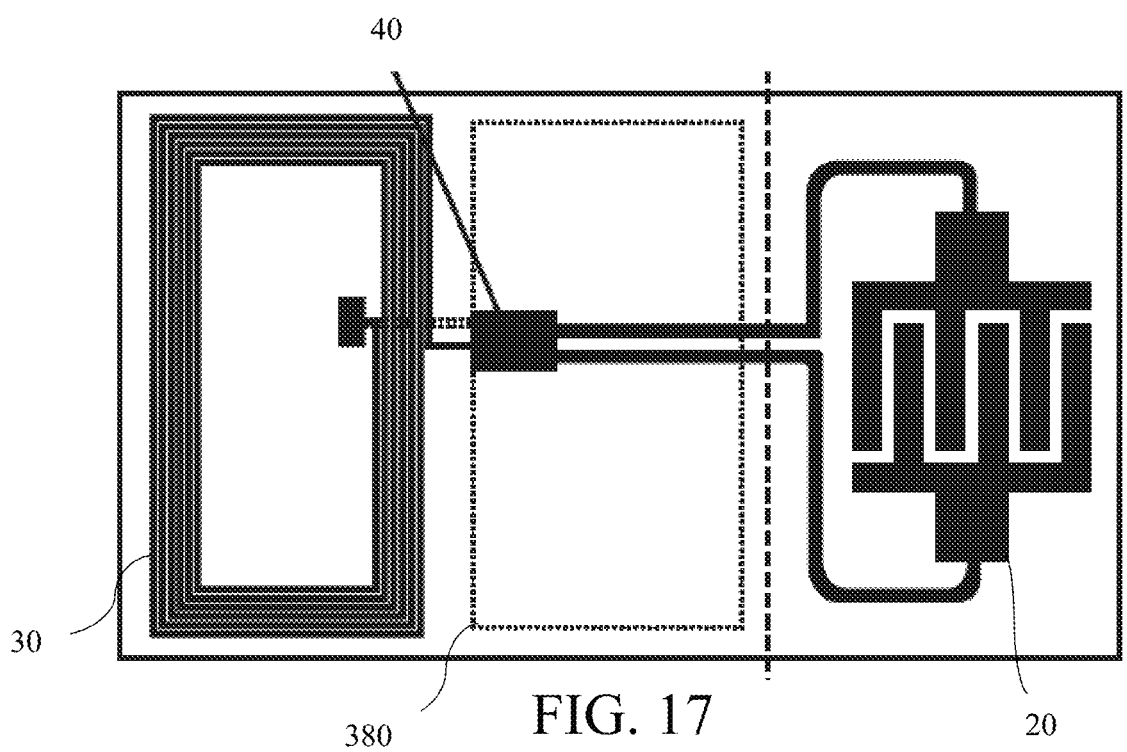
FIG. 17 is a single antenna print design for responding to NFC protocols forming one aspect of this disclosure.

The freshness sensor device or tag 10 is built such that it can send NFC and/or RFID signals. This may be accomplished as either a two-antenna system (as shown in FIG. 16), wherein the first antenna 30 responds to NFC, while the second antenna 30' responds to RFID. Alternatively, a single antenna may be utilized that is responsive to both NFC and RFID protocols. As shown in FIG. 16, the RFID 30 and NFC antennas 30', the IC 40 and sensor 20 components are printed on a single piece of substrate paper, such as a multi-functional substrate paper discussed in more detail herein. Furthermore, as shown by the dashed line, the substrate 330 is foldable such that the sensor 30 may be folded to the backside of the substrate With RFID high frequency and NFC tags operating in the same frequency, and the NFC specification being built off of an existing RFID specification, it is possible to leverage the common ISO/IEC 14443 specification to communicate with the same hardware (and even the same antenna) with either protocol. As such, consumer or associate mobile devices can then communicate using the NFC protocol, while longer-range access points or readers can use the RFID protocol to communicate. Of course, this does not negate the possibility of using a single antenna 40 device of either NFC or RFID design to convey the information (as illustrated in FIG. 17, wherein a NFC antenna 30 is illustrated, but the NFC antenna may be replaced with a RFID antenna or other passively reachable wavelength/frequency ranges).

Furthermore, this is a solution due to NFC and RFID reader devices using multiple initial trigger pulses to activate multiple NFC or RFID's at once. Due to the technology requirements that result in the readers pulsing their particular signal repeatedly, the addition of an "external" capacitor circuit and capacitance activated switch can be used to trigger both NFC and RFID antenna responses only once sufficient charge is held to power both antenna responses. The antenna print designs illustrated in FIGS. 16 and 17 both show a foldable flap to allow the sensor to be folded in order to reduce the space of the device/tag, so that it does not take up significant limited space in packaging of perishable item.

In the embodiments described herein, passive tag activation may be utilized to power the sensors and device. In use, an external device floods the antenna 30 space with electromagnetic radiation (specifically within the RF range) to activate the IC 40 and cause an antenna response. The antenna is then scaled in size to adapt to different RF ranges, which leads to changes in size of the sensor or device as a whole (sensor+antenna+IC components). As noted above, it may be beneficial to utilize a printable battery (not shown) that can be directly incorporated into the sensor such that Amine's and TVB-N's responses being emitted when Amine's and TVB-N's levels are able to trigger an electrical response of significant size.

Figure 18:
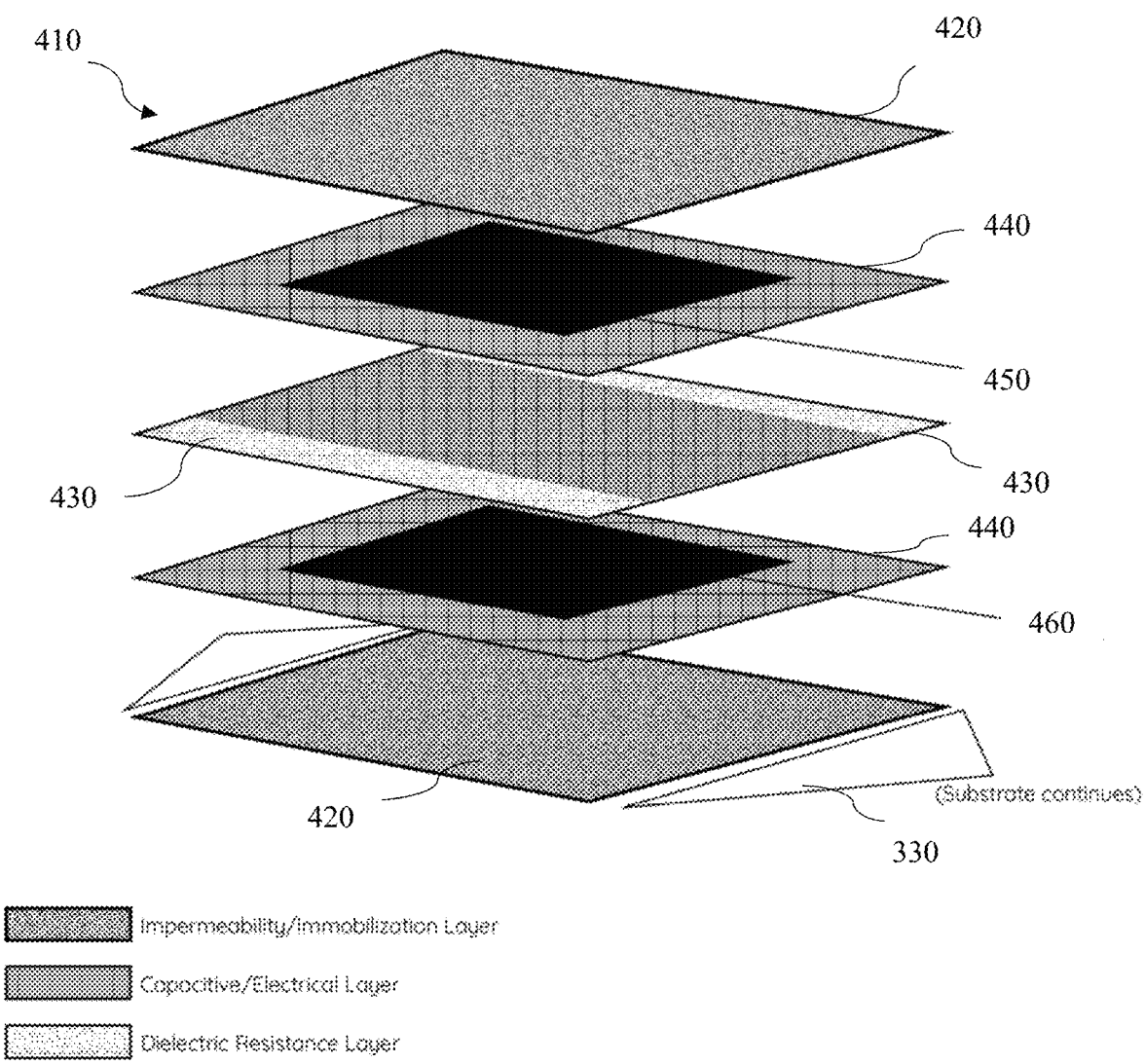
FIG. 18 is an exploded view of a printed capacitor forming one aspect of this disclosure.

There are various manners in which a capacitor 410 may be able to be construed for the tag or device 10. In accordance with one embodiment, a printed capacitor is illustrated in FIG. 18. The printed capacitor 410 has an A side 450 and a B side 460. The printed capacitor 410 further has an impermeability/immobilization layer 420, a dielectric resistance layer 430 and a capacitive/electrical layer 440. It should be appreciated that the capacitors described herein are not limited to use with freshness sensors, but are configured to operate in multiple applications in a wide variety of fields.

Figure 19:
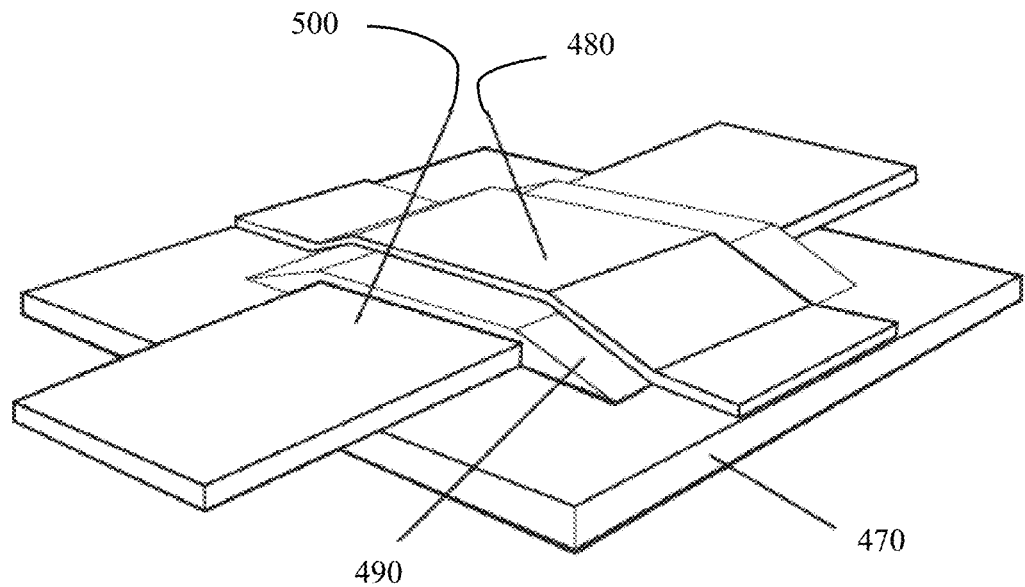
FIG. 19 is a perspective view of a capacitor built on a substrate using an inkjet or screen print printer forming one aspect of this disclosure.
Figure 20:
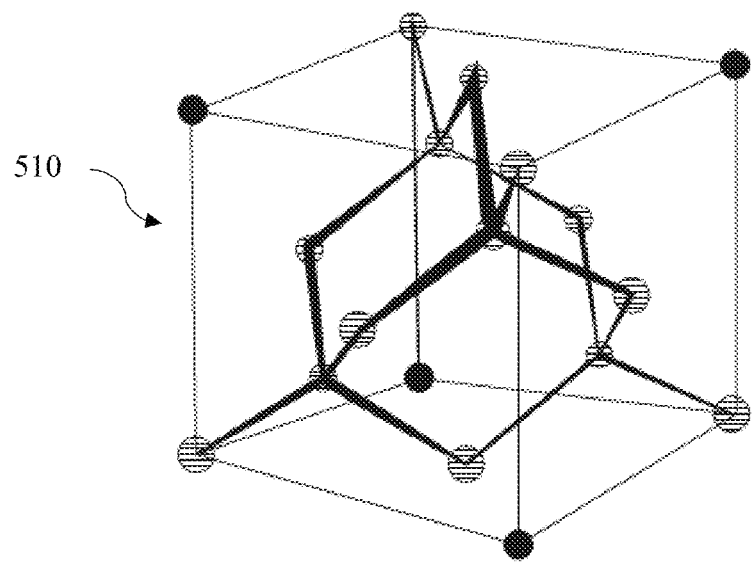
FIG. 20 is a perspective view of a diamond cubic crystal structure of a silicon unit cell forming one aspect of this disclosure.

In one embodiment shown in FIG. 19, the printed capacitor 410 is made for the device by coating a polyethylene terephthalate (PET) or other substrate 470 with a first electrode 480, a printed dielectric/insulator 490 and a secondary electrode 500, which is the standard configuration of the printed electrodes. The device may be fabricated from the substrate (PET) outwards. These structures are built upon wafers that are developed to be nearly defect free with near perfectly periodic crystal lattices of the unit cell structure 510 shown in FIG. 20.

Figure 21A:
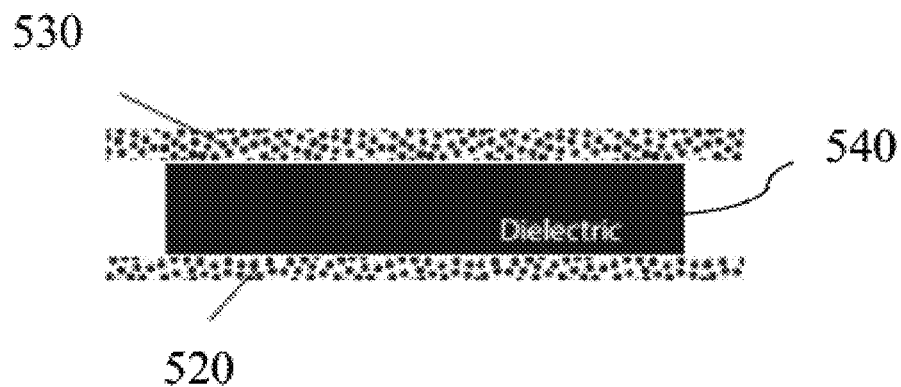
FIGS. 21A-21C are various views of a capacitor built using the substrate as the dielectric forming one aspect of this disclosure.
Figure 21B:
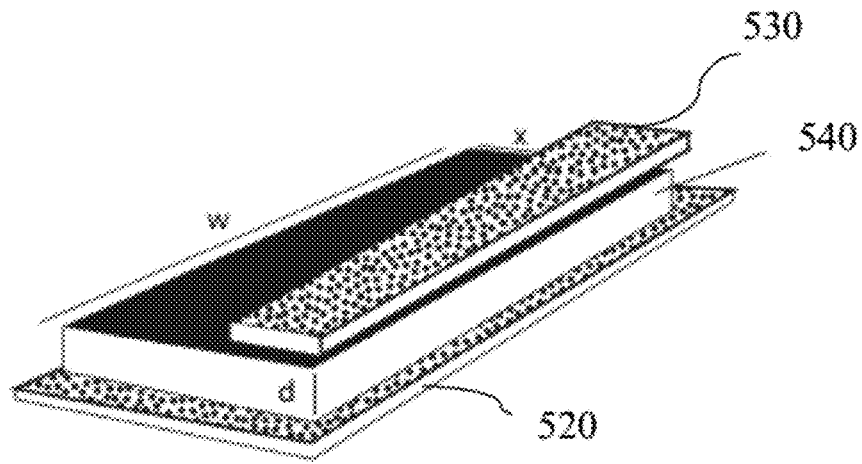
Figure 21C:
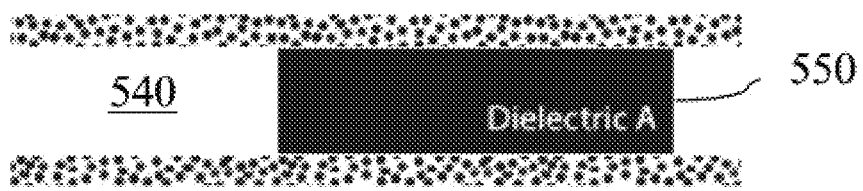

Turning to FIG. 21, an alternative method of developing the capacitor is illustrated. This method involves depositing the electrodes around the substrate (one fixed plate 520 and one mobile plate 530), which is then able to act as a dielectric bridge 540. Depending on the substrate, an additional dielectric coating 550 may be needed to reduce ink bleeding (as shown in FIG. 21C). One result of partial bleeding led to the possibility of expanded-surface-area and multi-layered expanded-surface-area dimensional capacitors.

Figure 22A:
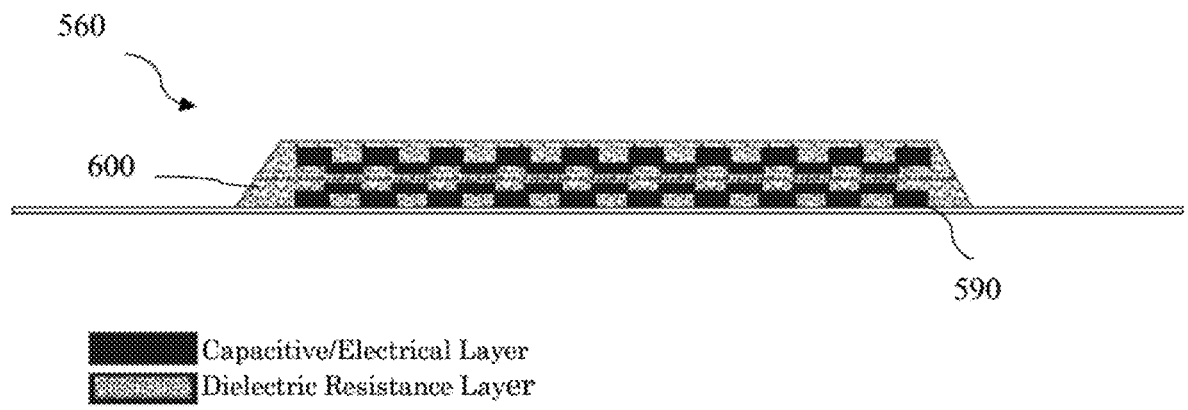
FIGS. 22A and 22B are cross-sectional views of expanded-surface-area printed capacitors forming one aspect of this disclosure.
Figure 22B:
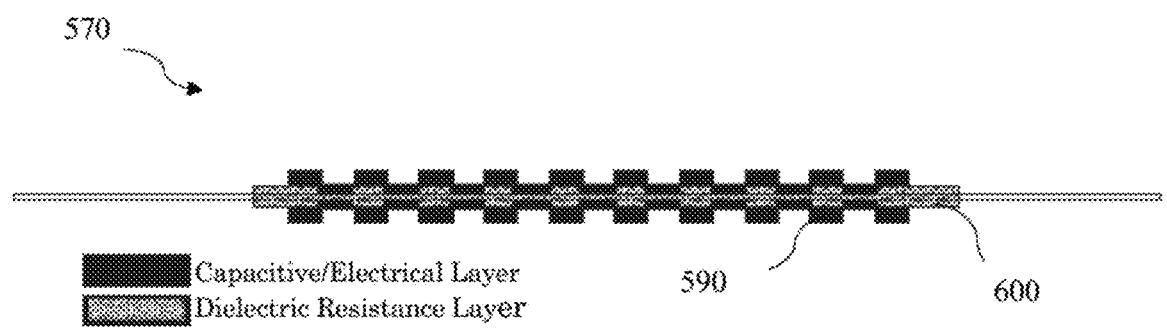

An expanded-surface-area printed capacitor is illustrated in FIGS. 22A and 22B. In FIG. 22A, an expanded-surface-area dielectric supported printed capacitor 560 is shown, while FIG. 22B illustrates an expanded-surface-area substrate gapped printed capacitor 570. Each of the capacitors 560, 570 has a capacitive/electrical layer 590 and a dielectric resistance layer 600. In other words, the substrate acts as the dielectric layer in both embodiments.

Figure 23:
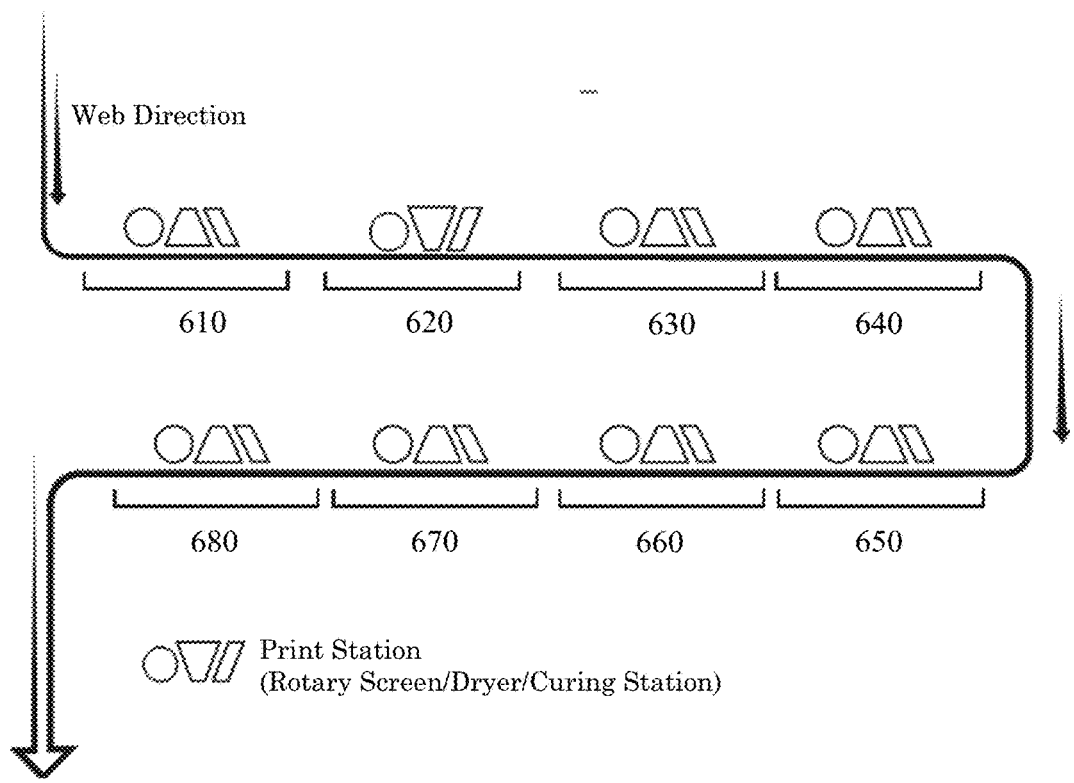
FIG. 23 is a diagram of an eight station approach of building the expanded-surface-area capacitor forming one aspect of this disclosure.
Figure 24:
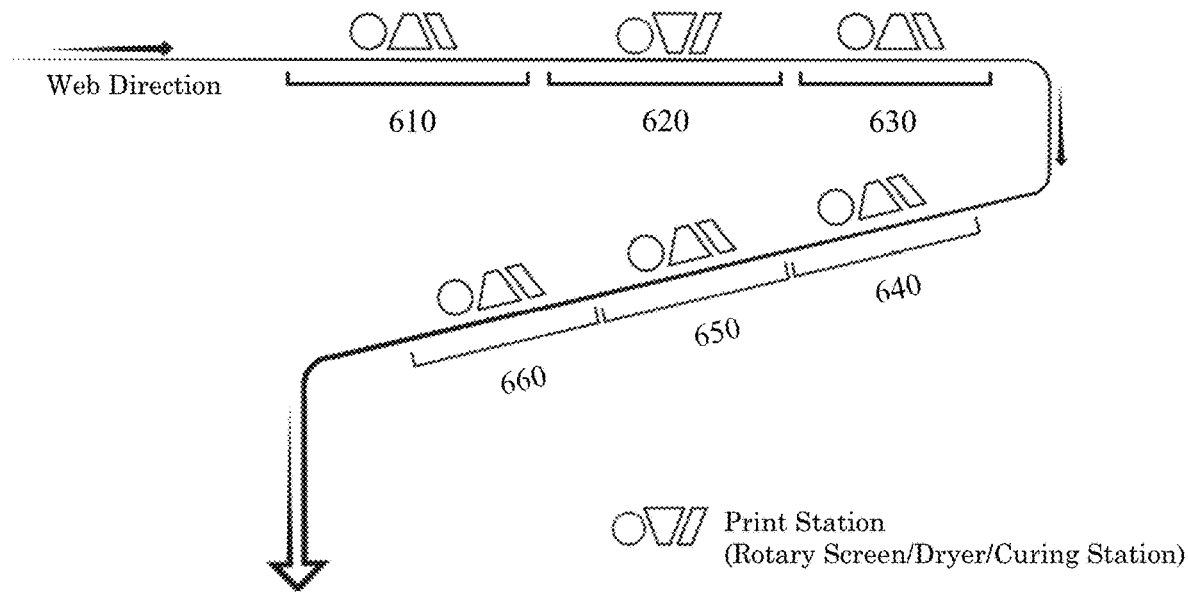
FIG. 24 is a diagram of a six station approach of building the expanded-surface-area capacitor forming one aspect of this disclosure.

The expanded-surface-area printed capacitors may be made via a six-step or eight-step approach illustrated in FIGS. 23 and 24, respectively. The eight-step approach includes: (i) a dielectric shim print 610; (ii) a conductive electrical layer 620; (iii) a conductive shim print 630; (iv) a dielectric fill print 640; (v) a conductive fill layer 650; (vi) a dielectric shim layer 660; (vii) another conductive shim layer 670; and (viii) a dielectric fill layer 680. The six-step approach includes the same steps except eliminates the dielectric shim layer 660 and the second conductive shim layer 670. The print station for both approaches includes a rotary screen print station, a dryer and a curing station.

Capacitors have smooth parallel plates that are separated by a dielectric. The possibility of controlled bleeding or substrates with pre-determined indentations allowing for periodic or random isotropic regains of closer electrodes, which provides two advantages. The first is the increased surface area of that is generated by the extension of the dips or nodules. The second is that these areas, being slightly closer together and with less dielectric (assuming the substrate centered acts as the dielectric) may be able to retain areas of grater charge density.

With respect to Amine's, TVB-N's and other gaseous byproducts of decay capable of being detected by the sensors and devices described herein, multiple sensors can be used to detect ranges of Amine's and TVB-N's. In certain embodiments, such ranges of ammonia can extend from 0-100 ppm with a sensitivity of 0.05 ppm. In some embodiments, TVB-N's may have a safety range that the sensor must cover which is 35 mg N/100 g. Of course, it should be appreciated that the detected ranges of Amine's, TVB-N's and other byproducts can vary with different perishable materials (from 0-1 part per 100). Furthermore, it is contemplated that to cover different ranges for different perishable items and provide a sensor having ranges to accommodate a particular level of sensitivity, various sensor designs, including changes in electrode surface area, length, conductivity and resistance may be utilized.

Similarly, it is known that the decay rates (while showing a slight variation in temperature) can be normalized to show a consistently similar decay trend of individual cuts of meat. It may be further contemplated that to accommodate for a desired range or sensitivity, the substrate upon which the inks are printed can be changed by methods, such as flood coating, caldering or other known printing techniques.

Figure 25:
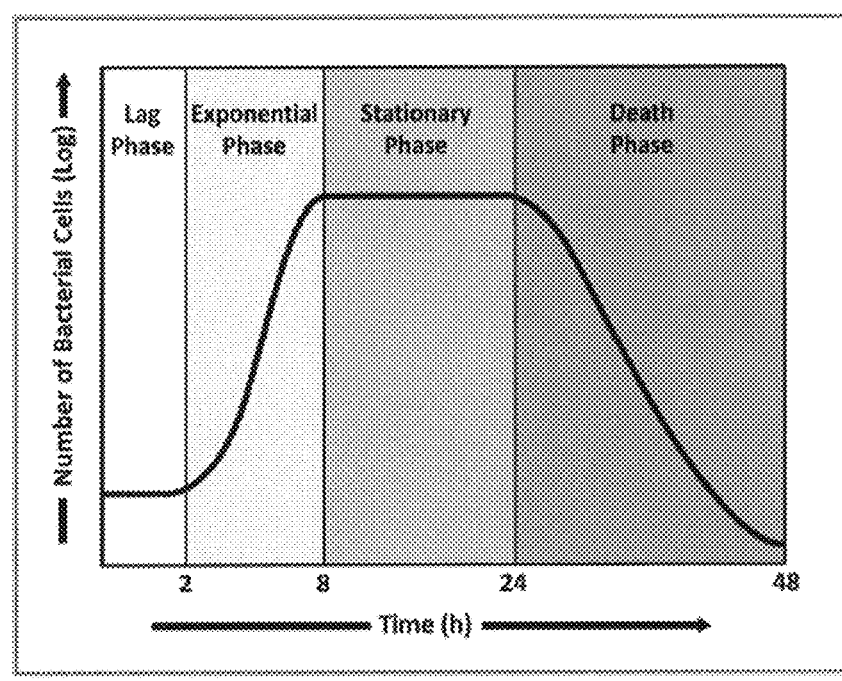
FIG. 25 is a prior art graph showing bacterial growth phases (see "Eradicating Bacterial Biofilms with Natural Products and their Inspired Analogues that Operate Through Unique Mechanisms." Aaron T. Garrison, Robert W. Huigens, Current Topics in Medicinal Chemistry, 2017, 17 1-8)
Figure 26:
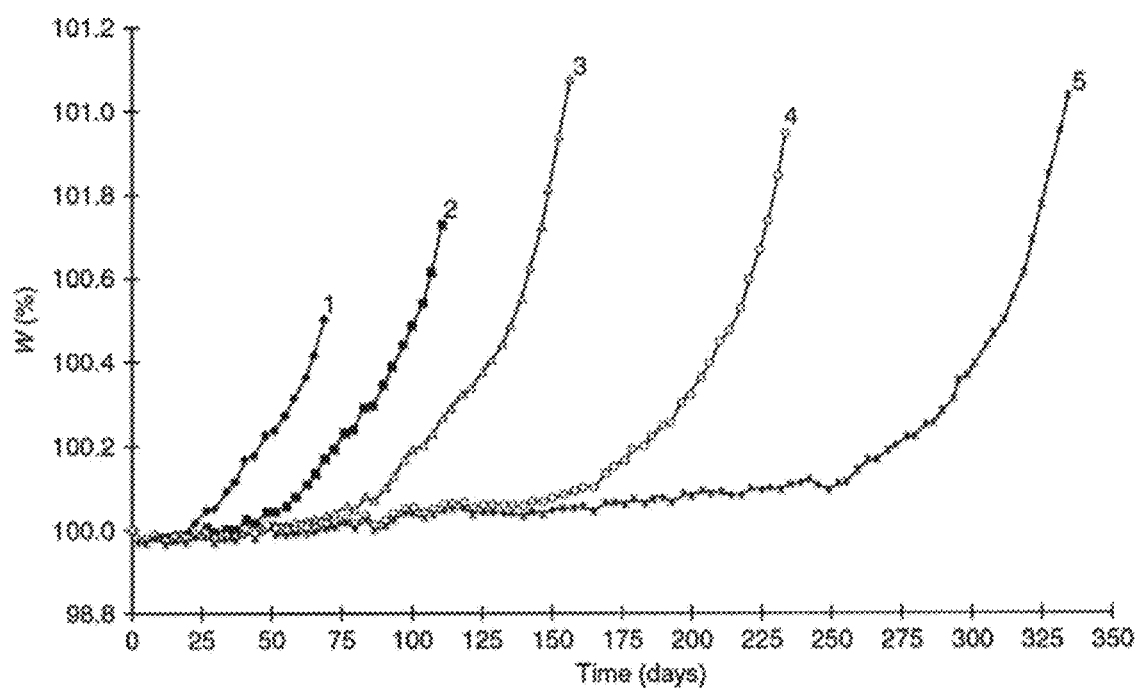
FIG. 26 is a prior art graph showing an exemplary course of oxidation of an oil (see "Handbook of Food Preservation." Editor M. Shafiur Rahman. $2^{nd}$ ed.)

With reference to FIG. 25, it is known that the byproducts released by microbes are directly proportional to the growth rate of the microbes. Similarly, the natural decay processes (chemical degradation of proteins, oils, fatty acids, and other constituent biomolecules of food items) will increase according to a similar trend. Turning to FIG. 26, it illustrates the oxidation reaction during storage of stabilized rapeseed oil.

In some embodiments, the addition of semi-permeable membranes allows for the removal of certain chemicals and/or the delayed effect of the chemicals activating the sensor 20. By coating the one or more sensor(s) with specific membrane types, a better match of chemical concentrations can be performed within the sensor's dynamic range. In other words, the application of a semi-permeable membrane 690 may result in an increase in time of the detection of specific chemicals.

Figure 27:
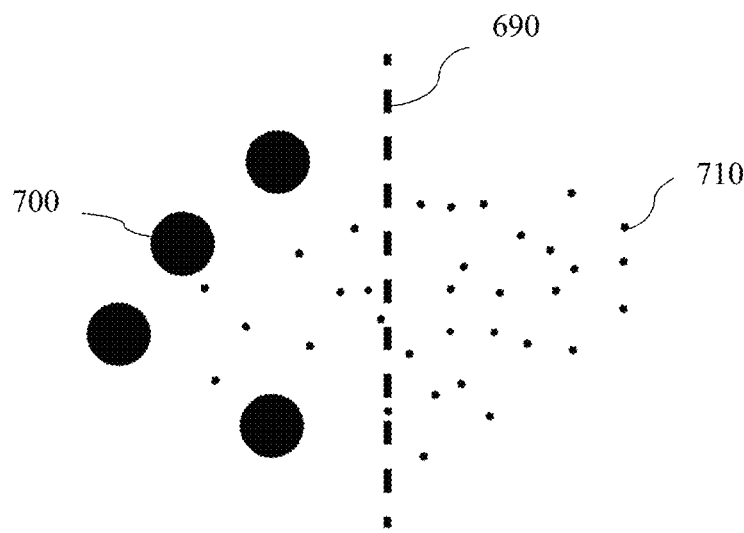
FIG. 27 is a prior art diagram of a semipermeable membrane acting as a filter to separate larger molecules from the smaller ones (see https://learn.concord.org/resources/760/diffusion-across-a-semipermeable-membrane)

Although this process does not affect the rate of decay or spoilage of the perishable items, it allows for periodic activation of separately coated sensors. Sensors having a semi-permeable layers of varying thicknesses can act as activation stages for the different concentrations of the chemicals being detected. For example, FIG. 27 is a prior art diagram of a semi-permeable membrane 690 acting as a filter to separate larger molecules 700 from the smaller ones 710. These sensors are also able to act as filtration devices, i.e., blocking larger unwanted molecules from being detected. This will remove specific large molecules for this device, but it does not allow for the specific isolation and detection of any one chemical. Thus, the detection of the spoilage or decay process results without specifically identifying any one chemical or molecule in the system.

In addition to coating an entire sensor with a semi-permeable membrane 690, it is possible to coat sections of the sensor with the membrane. From a resistance perspective, this results in a sudden periodic drop of resistance (also a change in voltage) experienced by the sensor 20. These sudden changes can be interpreted as crossing specific thresholds that indicate the current state of the spoilage or decay process of the perishable item. This is an additional benefit that can be used with the stepladder circuit shown in FIG. 8. Applying this style of coating to the sensor (staged or on separate sensors) can allow for a tunable activation process of different IC components as the voltage (and resistance) values change across the circuit.

It should be appreciated that different food types have different rates of decay, target compounds, compound specificities and/or sensor reactivity. Furthermore, different microbes on the food may affect this rate uniquely depending on food type and composite. In this regard, in certain embodiments, a predictive freshness may be determined by using a software application to track the freshness results from the sensor at different times. In turn, the application may be to warn consumers, retail stores, packaging plants and/or transport and delivery companies of the effects of external influences on the food freshness.

Figure 28:
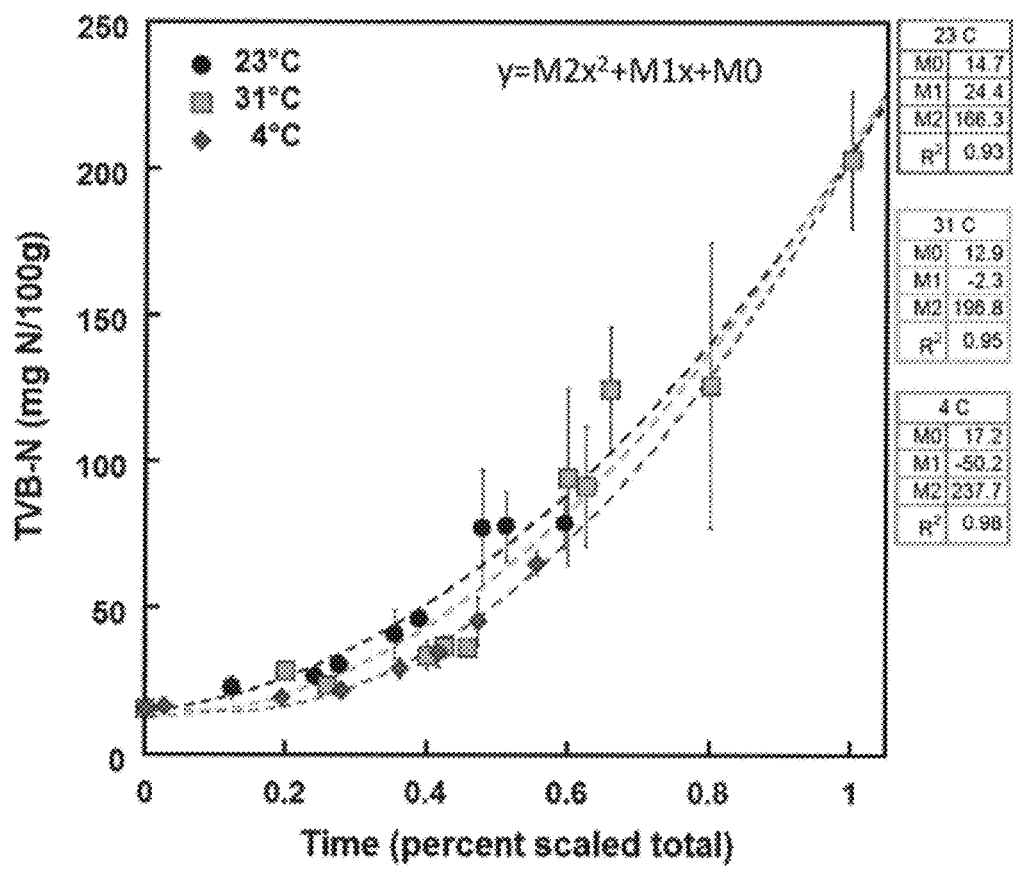
FIG. 28 illustrates normalized rates of TVB-N gaseous release from Tilapia forming one aspect of this disclosure.

Turning to FIG. 28, a clear correlation between the rate of TVB-N release in the gas phase and the normalized time values taken is shown. The normalization is used to scale the decay rates to a common trend, which can then be reintroduced to the product use by prediction for a given set/fixed temperature. The equation is described as a second order polynomial equation. The resultant variation due to temperature shows an optimal spoilage rate that is subsequently reduced for higher and lower temperatures. This is due to the optimal or ideal conditions needed to rapidly decay food. Deviations from this optimal rate, i.e., due to temperature or any other influence factor, reduces the rate of decay as they deviate from the ideal conditions.

Figure 29:
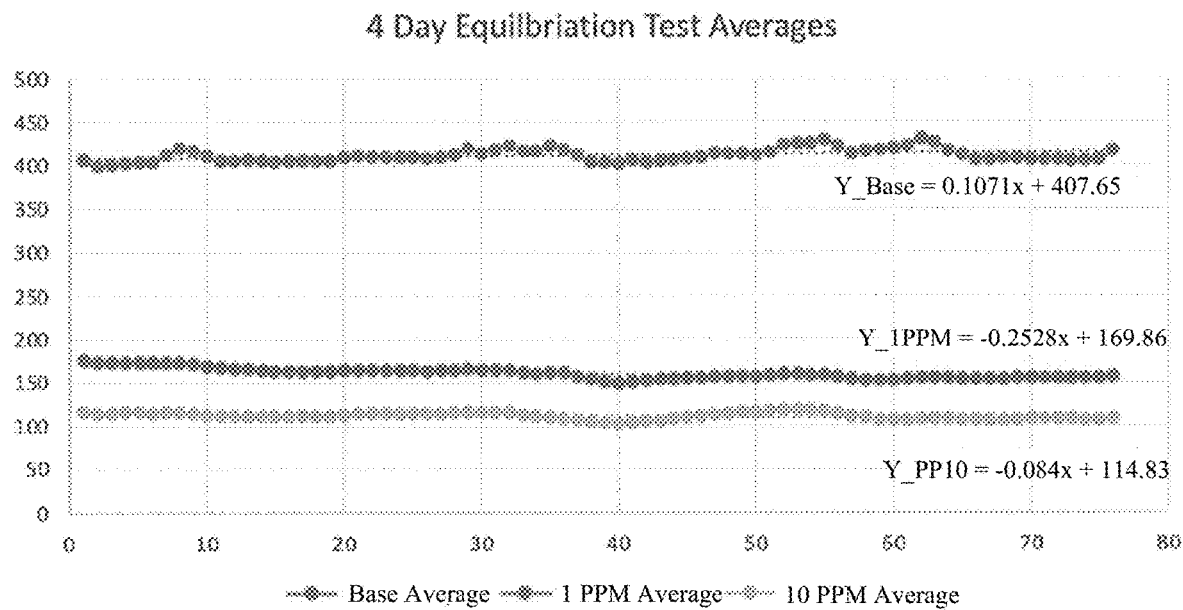
FIG. 29 illustrates $NH_3$ data lines with trend line equations showing the predicted trend of the resistance decline forming one aspect of this disclosure.

With reference to FIG. 29, $NH_3$ data lines with trend line equations showing the predicted trend of the resistance decline over four (4) days are shown. Each step represents an hour increase in time along the X axis, while the Y axis represents resistance. This acts as a baseline resistance value for demonstration purposes. It should be appreciated that a longer equilibration time can be used or tailored to a specific application or function based on the number of data points recorded.

In more detail, FIG. 29 shows the linear trends of the of the $NH_3$ values over time. The resistance value changes linearly over time and, therefore, a correction equation may be used to adjust for the slope of the resistance over time. Notably, the decline in resistance values is so slow that at the point at which an overlap would occur, the meat will have already become more spoiled. Given these initial results, the decline will take eight (8) days to impinge on the lower ammonia valued resistance. Although this indicates that no additional correction feature for this chemical is needed, this is not necessarily the case for all detectable chemicals and a correction algorithm may be used for some chemicals. It should also be noted that the difference in amount of ammonia results in a clear difference in resistance levels. These discrete changes allow for clear variations in the resistance values, which not only allows the device to determine the level spoilage the meat is currently undergoing, but given a recorded time-stamped history of the resistance values, a prediction of when the food will become unsafe can be estimated by the equations provided in FIG. 29.

Figure 30:
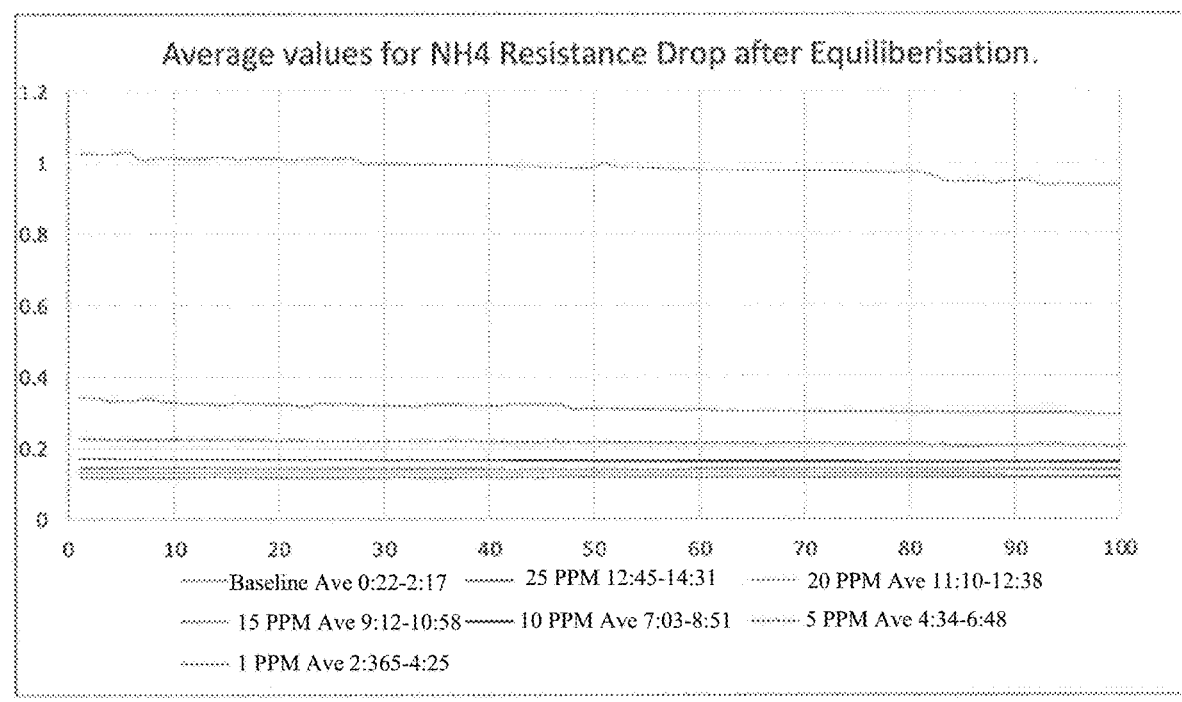
FIG. 30 illustrates resistance ratio values for multiple $NH_4$ concentrations added into the same environment over a 14-hour period forming one aspect of this disclosure.

Turning to FIG. 30, resistance ratio values for multiple $NH_3$ concentrations added into the same environment are illustrated. Each sample concentration reached equilibration (approximately 10-20 minutes) before the data was averaged. In addition to recording the resistance ratio values, it is possible to develop a ratio of resistance variations or effects that are consistent with the addition of $NH_3$ and other detectable chemicals. In light of the resistance ranges covered by the sensor, FIG. 30 shows the ratios compared to a base line of each individual sensor. This ratio allows for variations in the manufacturing process that can impact the sensitivity of the sensor to be minimized. The ratios may also allow for individual sensor normalization.

Figure 31:
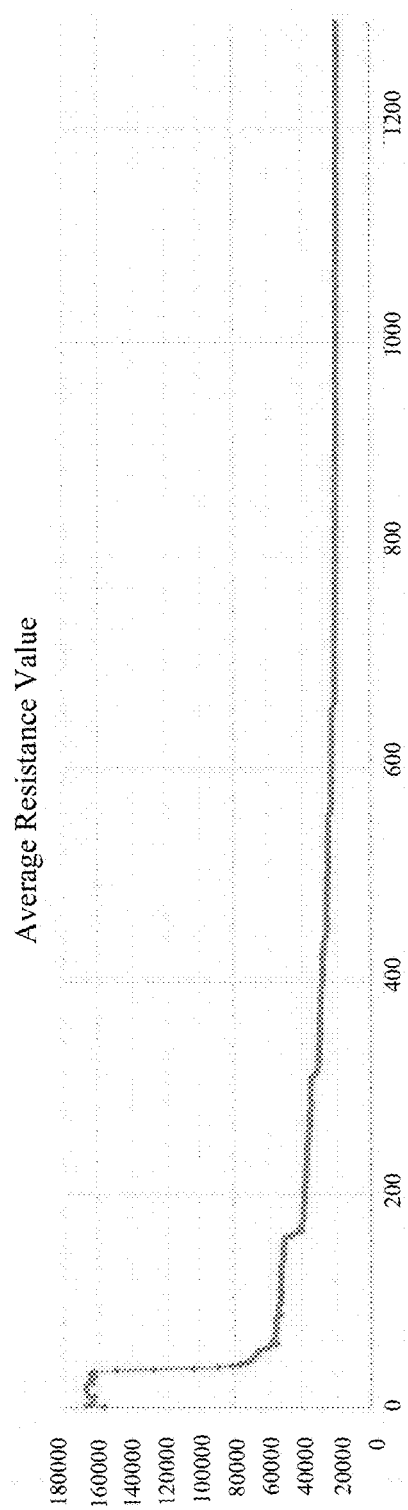
FIG. 31 illustrates a graph of the average resistance values for different $NH_4$ values over time forming one aspect of this disclosure.
Figure 32:
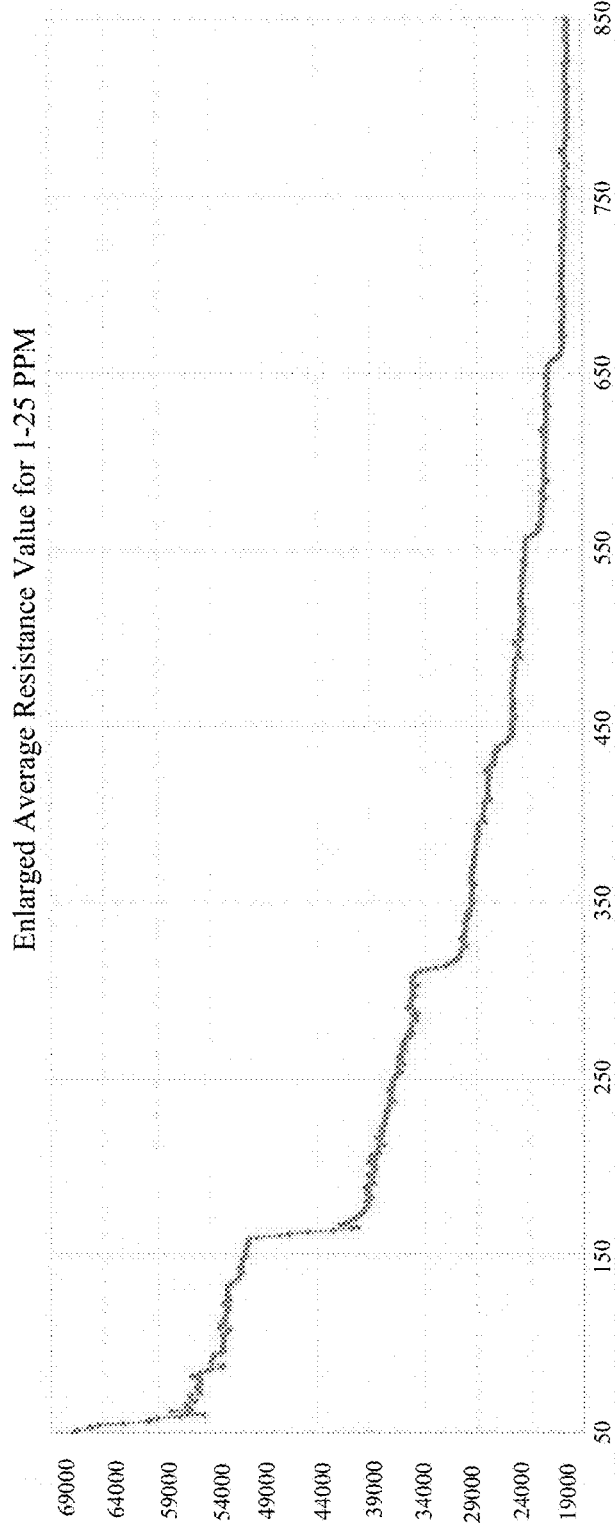
FIG. 32 is an enhanced view of the ammonia steps showing 1, 5, 10, 15, 20 and 25 PPM forming one aspect of this disclosure.
Figure 33:
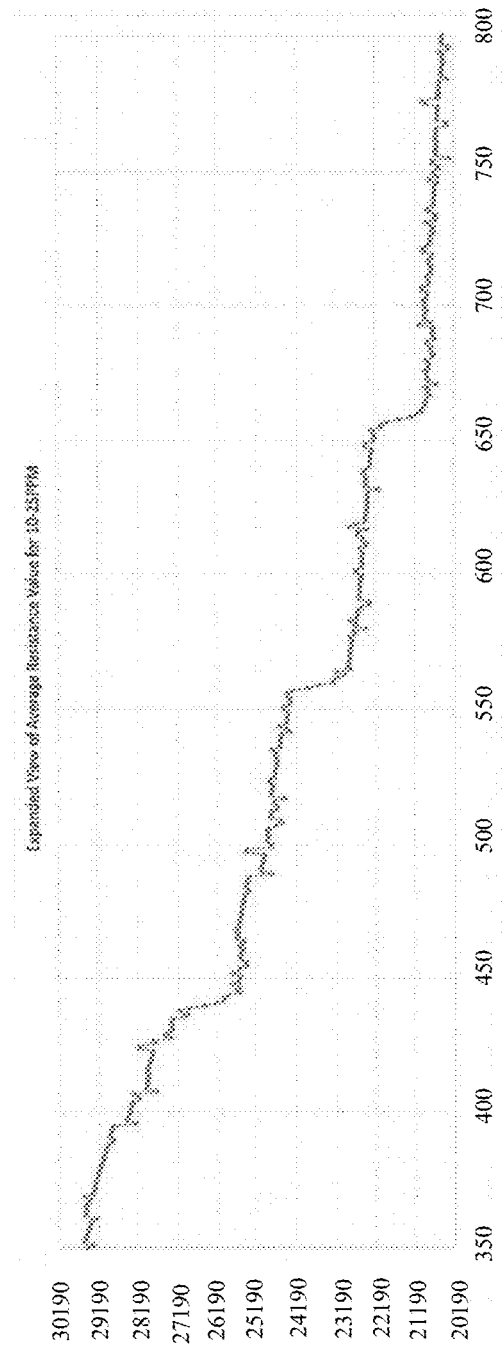
FIG. 33 is an expanded view of the steps observed by the increasing ammonia value changes forming one aspect of this disclosure.

As also shown in FIG. 30, regardless of whether a ratio or direct resistance results is used, the values for the ranges between 15-25 PPM become closer and difficult to distinguish. This particular range is less important from a specific value perspective as it is occurring on the exponential phase of the decay graph (see FIG. 25). Although a larger error may be represented in the resistance detection, it should be noted that the time variations (being along the exponential growth phase) will show a smaller variation in its prediction. With reference to FIGS. 31-33, these graphs are expanded views of the graph from FIG. 30 and show various views of the average resistance values for 1-25 PPM and 10-25 PPM.

It should be appreciated that depending on the substrate or coatings being used, equilibration can be affected by varying diffusion rates. These can be corrected by using a correction function. As the substrates absorption of the electrical or dielectric medium changes over time (for ammonia sensor case, water acts as the ion transport medium), the resistance (assuming no external tampering with the environment) can slowly lower. Similarly, the absorption of the charge carriers in that medium and the rate at which the charge carriers can cluster around the electrodes can also vary over time. As noted above, FIG. 33 shows an exploded view of the 10-25 PPM range detected by the sensor, wherein the changes appear to be very small. However, there are still clear steps and effects that occur when the sensor experiences changes in the concentration of the chemical under detection. These changes can be magnified and isolated using multiple data science and mathematical techniques, which will be described below.

Figure 34:
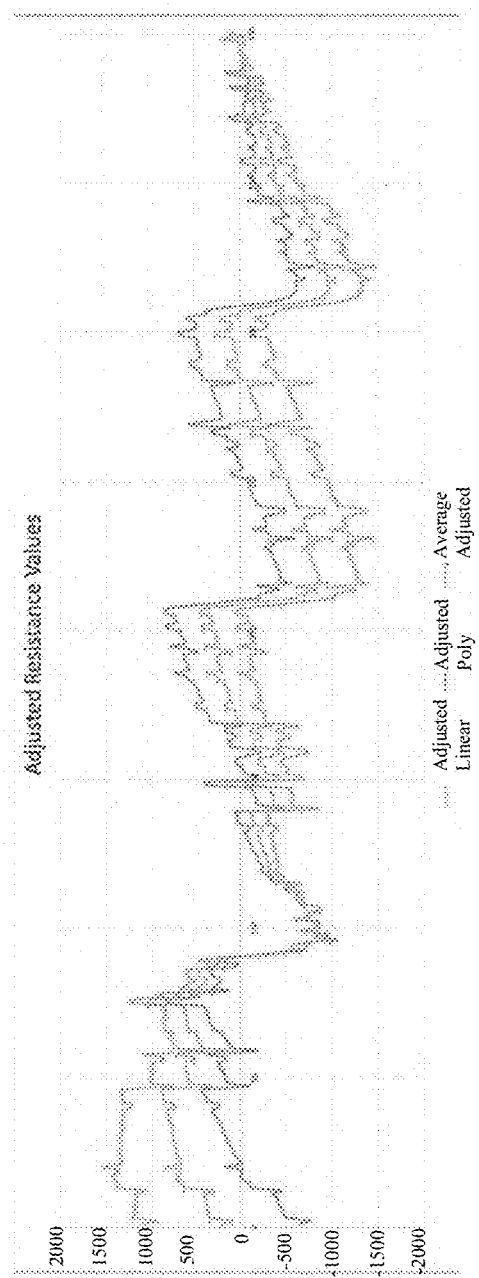
FIG. 34 is a graph showing a correction algorithm used on the average data forming one aspect of this disclosure.

A correction algorithm associated with the software application may be used to alter the data in order to make the ammonia changes more obvious. For example, FIG. 34 illustrates a correction algorithm that may be applied to the digital form data acquired by the sensor 20 in order to provide a freshness interpretation value via the software application running on the receiver. Additional rules may be added to identify common trends that occur when the spoilage ammonia values change. Specifically, a linear and polynomial regression as well as an average calculation were used in FIG. 34, but other algorithms may be used such that the freshness trends for particular perishable items may be monitored and updated in real-time.

Figure 35:
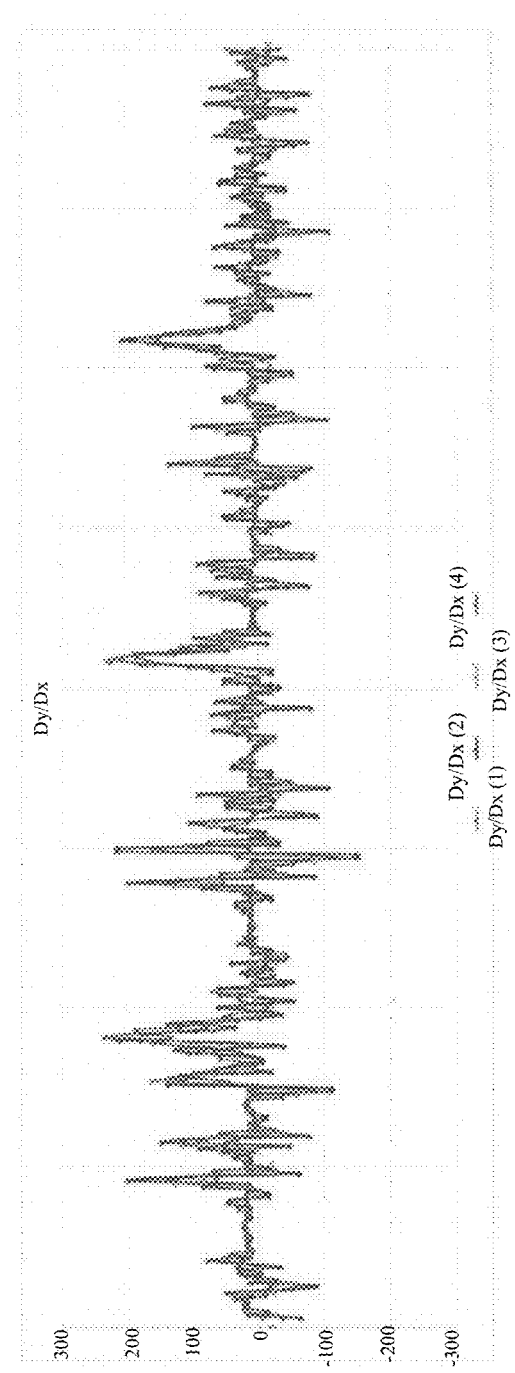
FIG. 35 illustrates differential calculations of ammonia levels experienced by the sensor forming one aspect of this disclosure.
Figure 36:
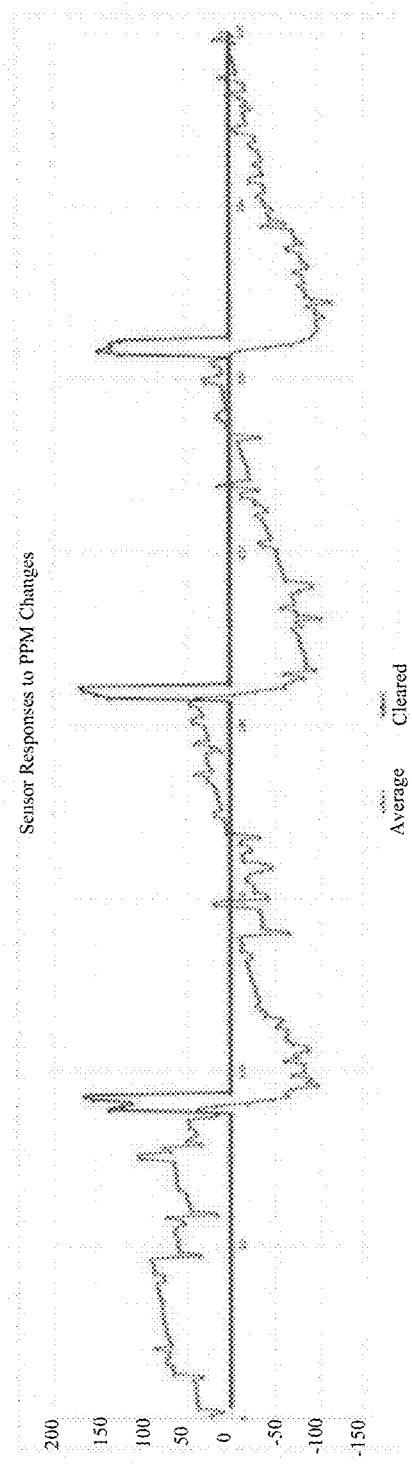
FIG. 36 illustrates rate of change calculations for the varying ammonia detected by the sensor forming one aspect of this disclosure.

In addition to a correction function, other functions can be used to identify effects caused by the sudden detection or change in concentration of the chemical being detected. For example, FIG. 35 shows the rate changes that are experienced by the sensor, while FIG. 36 shows an isolated graph of one of the differential methods used and with the application of additional data science tools. This one is particularly useful for the detection of changes in ammonia. The changes experienced by the sensor show consistent and clear spikes that occur exactly when the ammonia levels are changed.

The application of other algorithms can be used to add to the accuracy of the software application's ability to isolate and detect the changes experienced by the sensor 20. Additionally, the various algorithms may be used together to improve the accuracy of the software application over time (as more real-time data is recovered and entered into the application) as well as reading the resistance ranges that are detected on the sensor for different values of ammonia. This may be accomplished in stages based on resistance values or other experienced effects the sensor undergoes.

Figure 37:
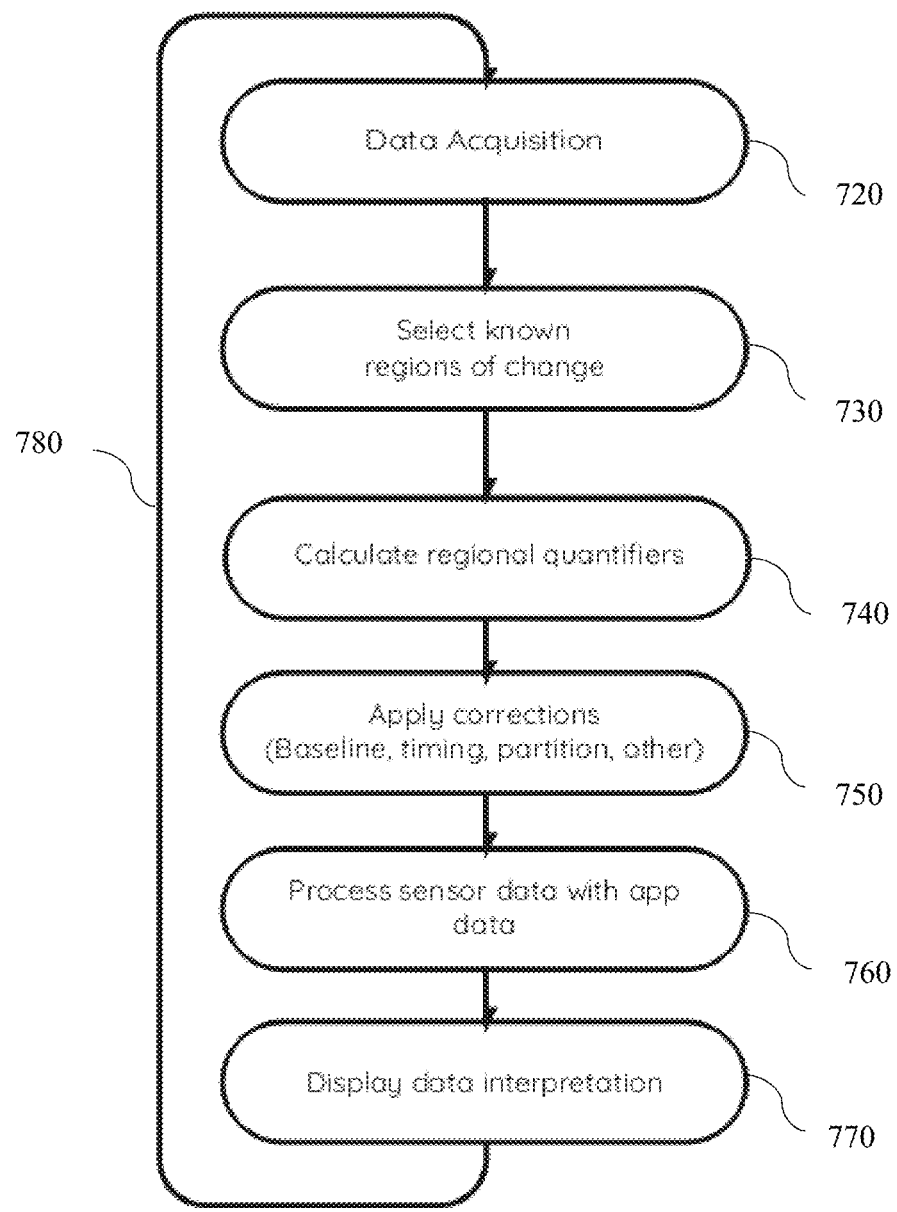
FIG. 37 is a logic diagram for calculating data inclusion for the software application calibration and chemical detection forming one aspect of this disclosure.

An example of the logic diagram for a method of calculating data inclusion for the software application calibration and chemical detection is shown in FIG. 37. Specifically, the logic flow is as follows: (i) data acquisition 720; (ii) select/isolate known regions of change 730; (iii) calculate/determine unique regional qualifiers (trend lines, value ranges, etc.) 740; (iv) apply corrections, data science tools, logical decisions to data (baseline, timing, partition, other) 750; (v) process/incorporate sensor data with application data 760; (vi) display data interpretation 770, including updating data with real-time application data; and (vii) repeat logical process with new data 780. It should be emphasized that different calibration curves may be used for each perishable item.

The method of calculating and predicting spoilage may involve taking the resulting patterns (from the data analysis of the sensor resistance patterns) and correlating the patters to resistance equivalency values (x Ohms is equal to y chemical concentration). This relates directly to the current ammonia levels that have been correlated with specific resistance values. The ability to time-stamp all the resistance values also allows the relative ammonia values to be time-stamped, which can then be used to in correlation with the decay equation calculated for a particular type of meat. Subsequently, this information is used to determine the current state of the spoilage decay and predict when the future state of the spoilage and decay will reach dangerous levels. This process of resistance to ammonia concentration to time stamp to current state to future decay state and decay rate can be processed to deliver this important information through the software application, NFC/RFID and sensor device.

Importantly, these processes and data analysis methods have led to the development of a series of discrete markers for identifying spoilage and decay on meat as shown below in Table 3, which illustrates an example of the logical progression used to govern the software application response from the different chemical values.

TABLE 3

| Stage # | Resistance Range KΩ | Ratio to Baseline | Spoilage Equivalence (PPM) | External Message |
|---|---|---|---|---|
| 0 | +120 | 1 | <0.05 | Food is safe |
| 1 | 60-45 | 0.4-0.2 | 1-5 | Spoilage has begun approximately X days remain. |
| 2 | 45-34 | 0.19-0.15 | 5-10 | Spoilage is occurring, eat today or tomorrow. |
| 3 | 34-26 | 0.18-0.13 | 10-20 | Spoilage is becoming a problem. Cook Food well. |
| 4 | 26-23 | 0.12-0.1 | 20-30 | This may be unsafe to eat even after cooking. |
| 5 | 23-20 | 0.1-0 | +30 | This is no longer safe to eat. |
| 6 | 100-80 | 0.8-0.65 | Unknown | An unknown chemical is detected, this food may not be safe to eat. |

It should be appreciated that the sensors described herein are able to detect multiple other TVB-Ns besides Amines. These by-products can vary in concentration and rate of release depending on the meat and external environmental conditions. These other by-products include, but are not limited to cadaverine and histamine.

Figure 38:
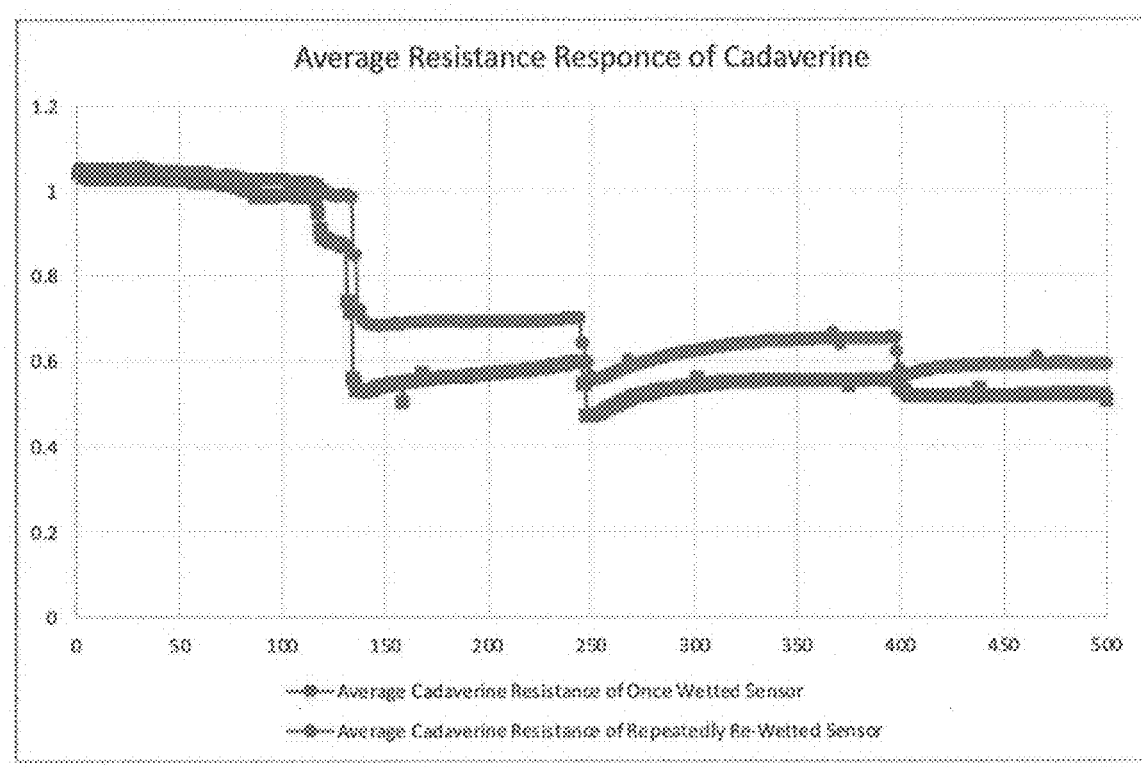
FIG. 38 illustrates average cadaverine resistance at different PPM values over time forming one aspect of this disclosure.
Figure 39:
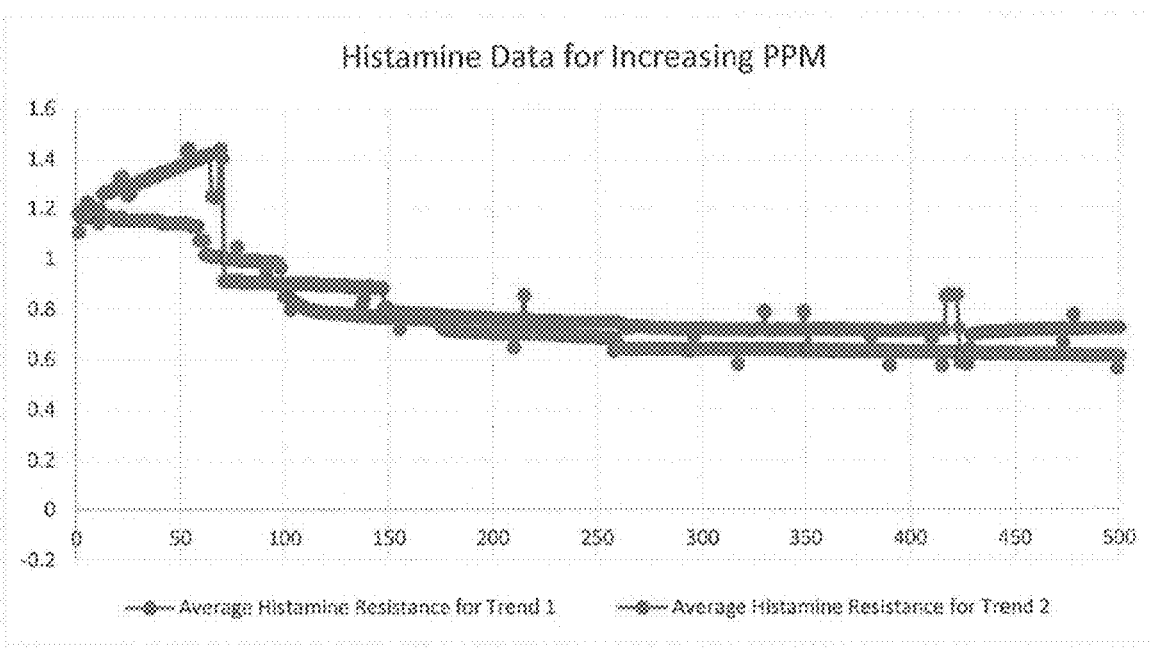
FIG. 39 illustrates detection of histamine data for increasing PPM values forming one aspect of this disclosure.

For example, FIG. 38 illustrates the average resistance response of cadaverine, while FIG. 39 illustrates Histamine data for increasing PPM values. Specifically, FIG. 38 shows the sensor resistance reaction to changing PPM values of cadaverine. As illustrated, the introduction of cadaverine has clear and rapid resistance changes. Unlike ammonia, cadaverine shows a more stabilized resistance ratio of above 0.4. Consequently, it is clear that the specific chemical versus resistance fingerprint for cadaverine is different to ammonia.

FIG. 39 illustrates a similar trend for histamine as clear resistance drops occur at increasing PPM values. Similar to the cadaverine, the resistance ratio does not to drop below 0.5. Using artificial intelligence (AI) and data science tools, the identification of a non-ammonia emission may be made, but it is not currently possible to differentiate between TVB-Ns to act as a clear chemical identifier. This detection does allow for the additional detection of other chemicals given of during the spoilage process that causes meat to become rapidly inedible.

Using the ammonia values from FIG. 28 and the correlation between known ammonia, cadaverine or histamine levels and the equivalent resistance value or ratio, it is possible to predict the remaining life of the meat once the decay process has started. It should be noted that most retailers currently use "sell by" or "use by" dates on their perishable items. These dates only give a statistical predicted or estimated life span of the perishable item, such as meat before spoilage occurs. Importantly, these dates do not take into account any other variables that may be experienced by the perishable item.

To this end, the onset of the smallest detectable amount of a spoilage gas will, through the application of the freshness sensor device or tag and the related application, allow for an accurate prediction of the remaining fresh/safe life of the perishable item and a determination of toxicity that would be considered dangerous to the consumer. By comparing and time-stamping the resistance levels to against the statistical "use by" date, it is possible to determine that a perishable item is still safe even after its "use by" or "sell by" date. Similarly, if the product is poorly maintained but has not reached its "use by" or "sell by" date, the freshness sensor device described herein can warn the consumer of the product's state to potentially avoid illness, food poisoning and, in extreme cases, death.

Because the decay process is repeatable, it is also predictable and as shown in FIG. 28, it can be normalized. The process of normalization allows for a simplification of the equation to be used ($Y=M_2X^2+M_1X+M_0$). This is used to adjust the results to different storage temperatures (that can be inputted either by the consumer, via the application or from a temperature sensor on the freshness sensor device). Additionally, once the decay process begins, the known spoilage equation for a particular perishable item may predict the remaining edible life and more accurate approximate time until toxic spoilage.

Figure 40:
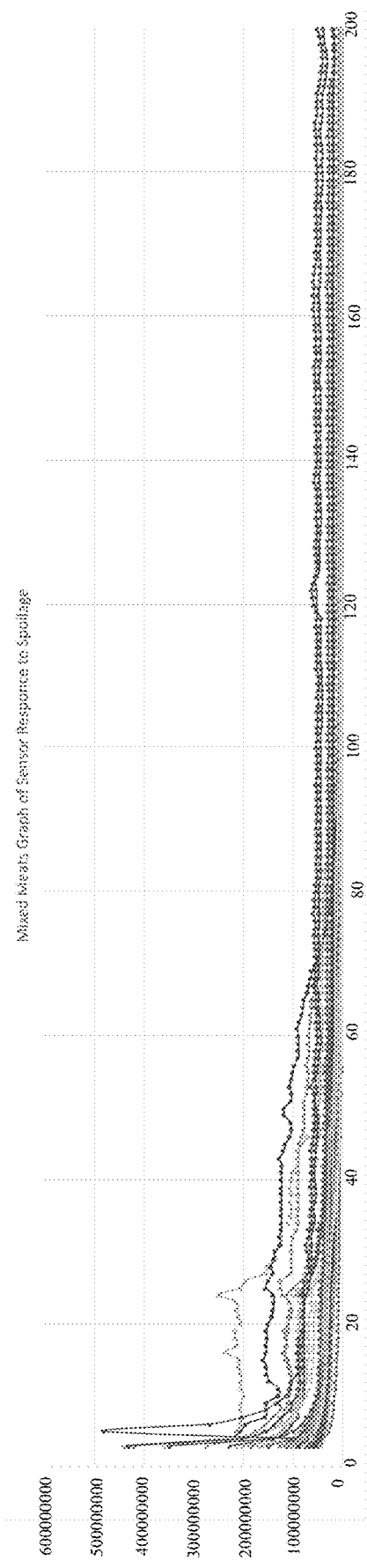
FIG. 40 illustrates an approximate nine day overview of resistance trends of various meats forming one aspect of this disclosure.

Tests were done to show the ability of the sensor to detect the variations of TVB-Ns emitted by multiple meats. The results show a clear correlation between resistance values experienced by the sensor as the meat spoils. Its important to note that these results are from the general TVB-N gasses released. No specific gas is detected or identified. The results shown in FIG. 40 show a clear decline in the resistance after the start of the experiment. Importantly the sensors are (during the equilibration phase—hours 0-20) should not be interacting with any TVBN gasses. Between the 40th hour onwards the meat begins to show a varying range of resistance values. The meats tested are Chicken, Fish, Pork and Steak.

Figure 41:
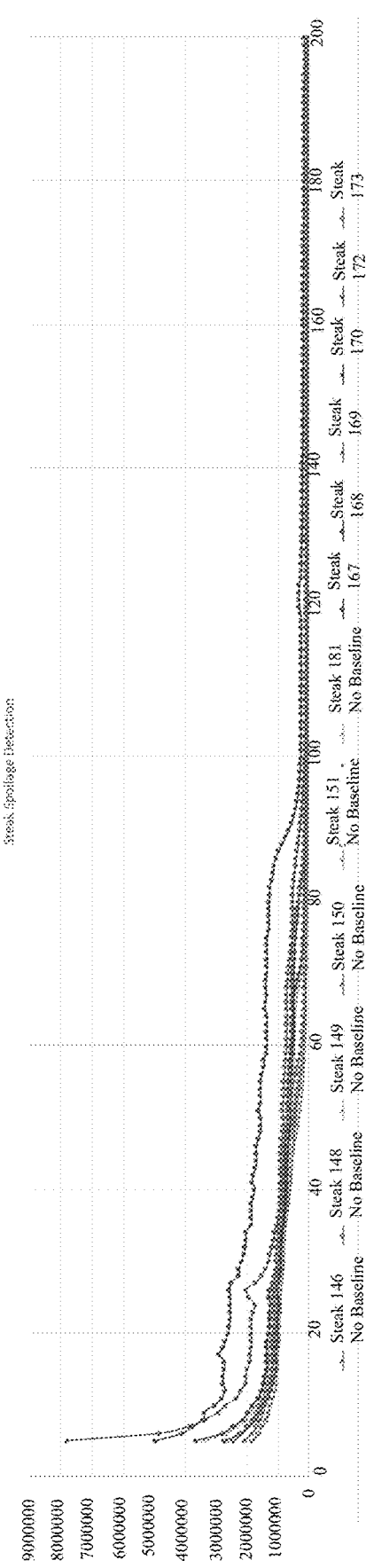
FIG. 41 illustrates an approximate nine day overview of steak spoilage detection forming one aspect of this disclosure.

FIG. 41 illustrates steak spoilage and decay over a nine-day period, wherein the X-axis is in hours and the Y-axis is in Ohms. In more detail, FIG. 41 shows an isolated group of steak taken from the data shown in FIG. 40. It should be noted that the steak was not placed into the detection environment at the same time, which resulted in a clearer activation of the sensors at varying (but similar) times. Furthermore, the graph in FIG. 41 shows a tighter cluster of resistance bands for the spoiling steak. One important point is that the steak shows specific resistance drops at different times. This indicates the steak is spoiling at different times, which is expected and can be clearly identified and monitored.

Figure 42:
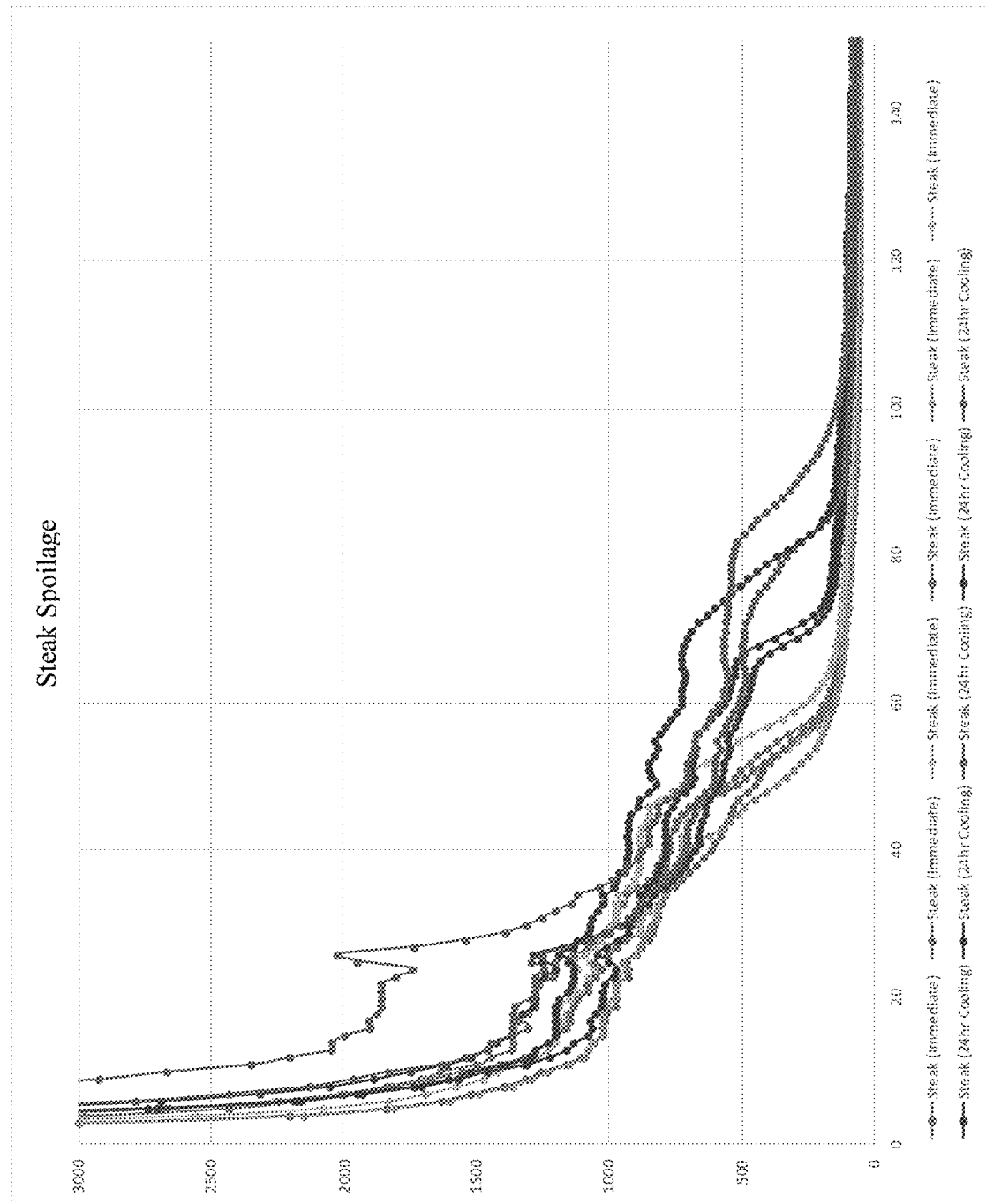
FIG. 42 illustrates varying spoilage rates of steak between being tested immediately and after being cooled forming one aspect of this disclosure.

With reference to FIG. 42, it is an expanded view of the spoilage effects occurring in the steak, wherein the X-axis is in hours and the Y-axis is in kOhms. In more detail, the varying spoilage rates of steak tested immediately and steak that was cooled for an additional 24 hours. The results show varying spoiling rates occurring at over 50 hour. Furthermore, although the rates of resistance change appear different for each sample, they are all significantly different from the natural sensor equilibration resistance rate change shown in FIG. 40. This is one of the identifying markers that the spoilage process has begun, which is discussed in more detail below.

Figure 55:
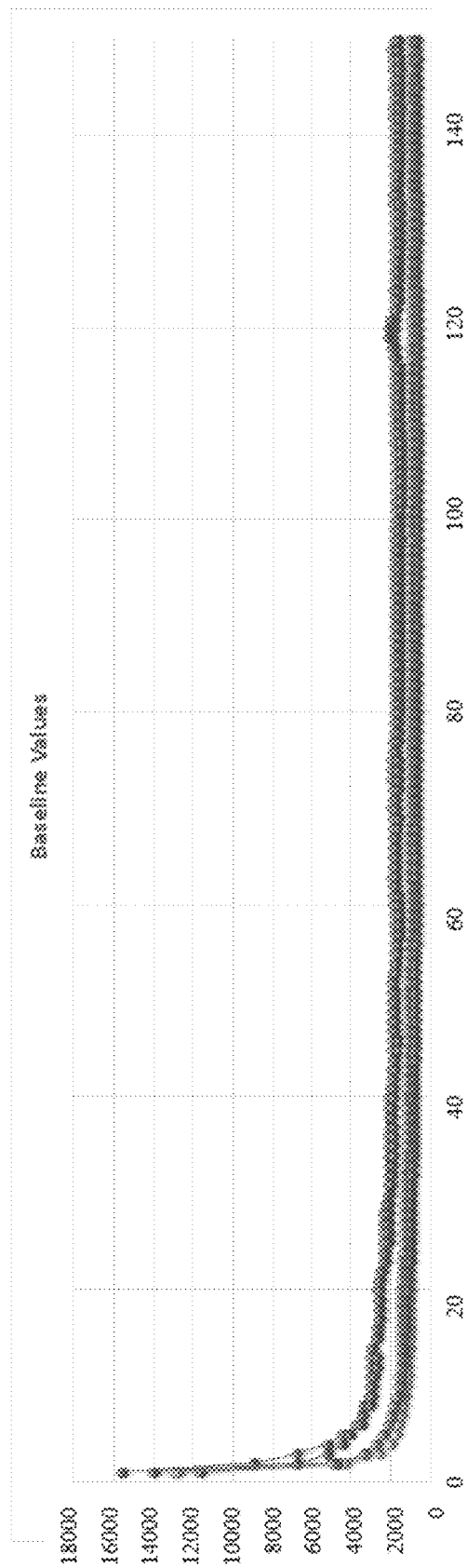
FIG. 55 is a graph of baseline values of multiple sensors without any chemical activation forming one aspect of this disclosure.

Turning to FIGS. 55-62, a detailed data analysis related to sensor responses were performed. It should be appreciated that there are multiple methods for identifying the arrival of the spoilage process, which are discussed below. However, the present disclosure is not limited to any particular method of data analysis or data science to identify the presence of spoilage. FIG. 55 shows the baseline values of multiple sensors without any external stimulus, i.e., chemical reaction, but with the conditions required to activate. These sensors require water to act as the chemical medium and as such require an additional moisture equilibration time. Taking this information into account allows for a baseline normalization process.

Figure 56:
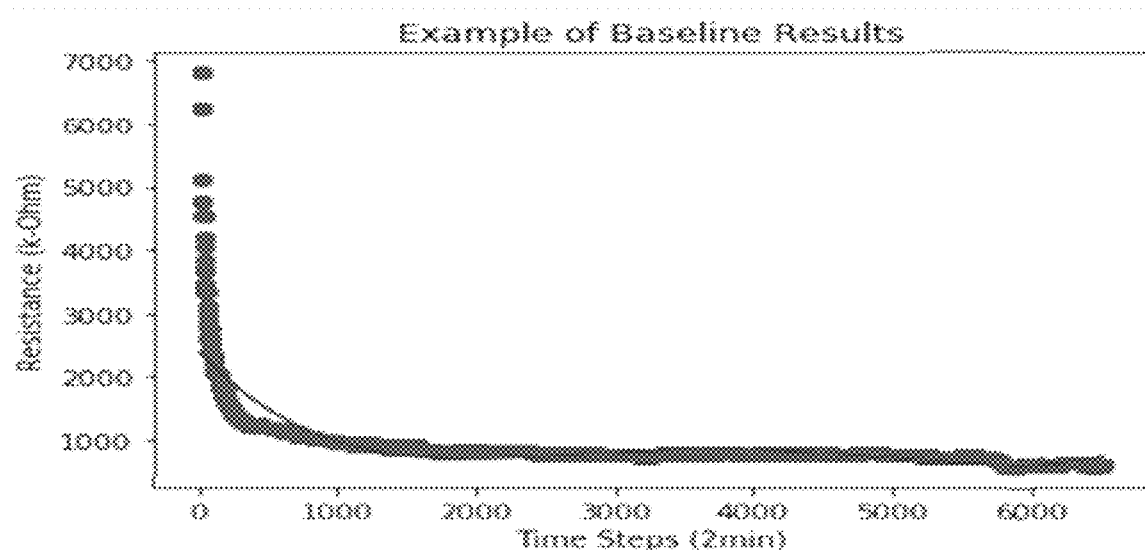
FIG. 56 is a graph of baseline results of a sensor response without any stimulus or chemical activation forming one aspect of this disclosure.
Figure 57:
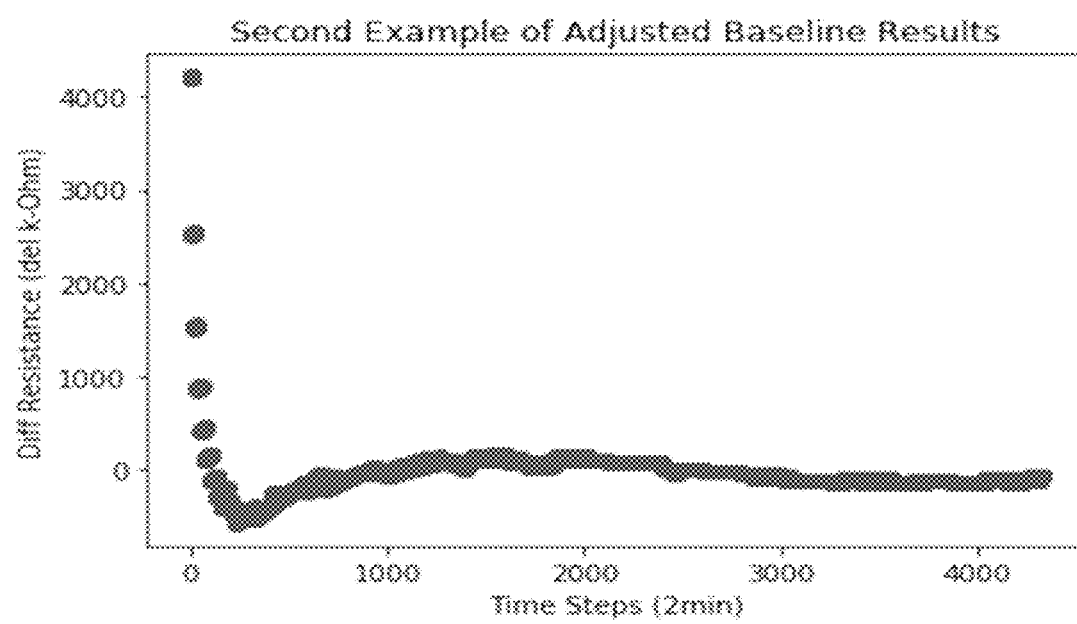
FIG. 57 is a graph of adjusted baseline results using a polynomial adjustment protocol forming one aspect of this disclosure.
Figure 58:
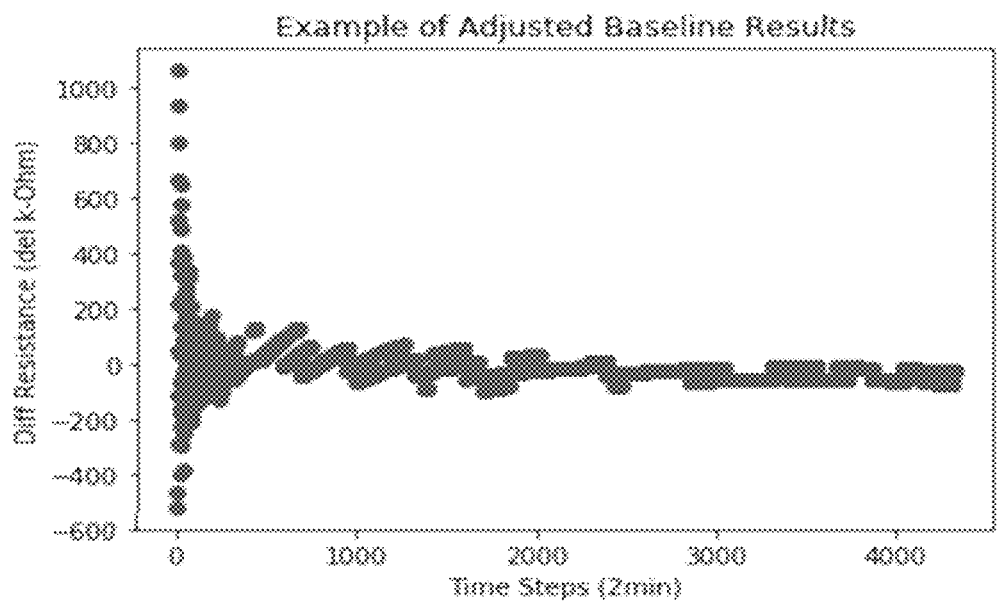
FIG. 58 is a graph of adjusted baseline results using a complex protocol forming one aspect of this disclosure.

FIG. 56 illustrates the baseline results of a sensor response without any stimulus or chemical activation for nine days with results taken every two minutes. Again, there are multiple methods for describing the equilibration function observed, i.e., methods to correct for the natural equilibration process experienced by the sensor. Once a method is selected, an adjusted baseline is used to identify when the sensor is undergoing some form of chemical interaction and being activated. As shown in FIG. 56, the curved value fluctuations are a response to both the sensors sensitivity (of approximately 0.05 PPM) and the tags IC's internal error when calculating the resistance. These combined with the correction algorithm (discussed above) resulted in the bobbling appearance. An example of adjusted baseline results is shown in FIG. 57, wherein a simple polynomial adjustment protocol is used in adjusting the baseline results based upon the sensor data collected and analyzed via the software application. FIG. 58 illustrates another example of adjusted baseline results wherein a more complex process is utilized.

Figure 59:
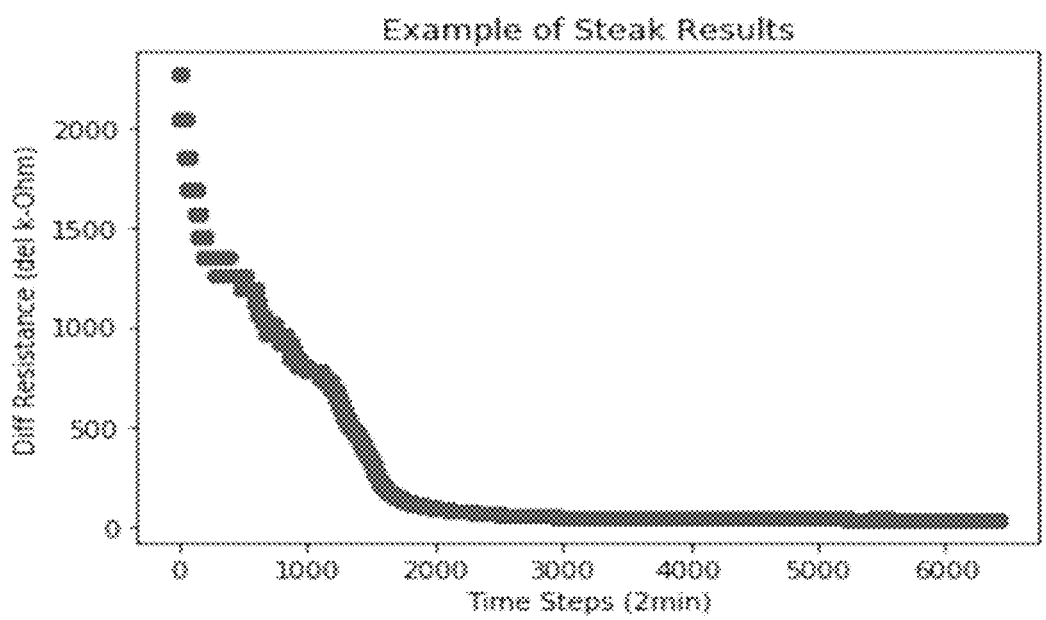
FIG. 59 is a graph of spoilage of steak over a nine-day period forming one aspect of this disclosure.
Figure 60:
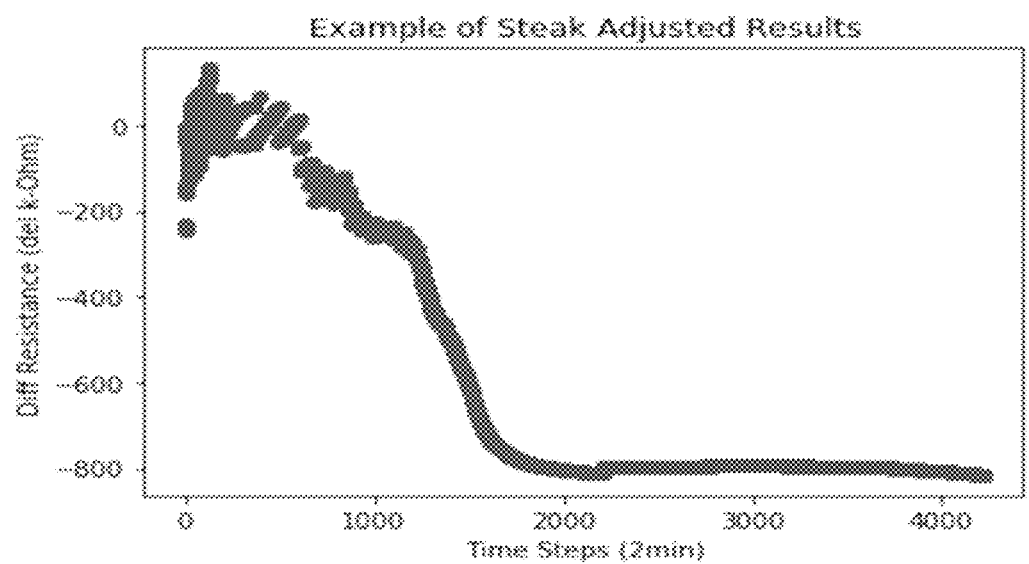
FIG. 60 is an adjusted graph of steak spoilage forming one aspect of this disclosure.

Once the baseline is corrected or adjusted, identifying the effect of sensor activation is simplified. For example, FIG. 59 is a graph for steak spoilage over time. However, these results are not adjusted so that they appear similar to the baseline results shown in FIG. 56. Turning to FIG. 60, an adjusted graph of steak spoilage is illustrated. It is highlighted that there is an extreme deviation from the Y=0 baseline that the previous baseline sensors were oscillating around. It is clear that the spoilage process allowed for the results to substantially deviate from the known baseline values.

As a result, this process has identified a region where the meat has spoiled. Using this information (the deviation from the baseline 0), the data can then be used to identify the degree of spoilage of the meat. One representation of this is a direct comparison of resistance values to those recorded by the ammonia tests shown in FIGS. 30-33. Due to the variability within the sensors, it is difficult to determine the degree of spoilage of the meat. Other calibration methods may be used with the ammonia results to identify specifically when the meat reaches some of the more known states of spoilage. It should emphasized that the sensors are accurate and able to detect 0.05 PPM of ammonia and accurate measurements of other chemicals being imitated are currently unknown (as a specific chemical is not being detected). This means that other chemicals may have similar effects to ammonia. For this example, the ammonia detection limits and the mathematical calibrations and/or adjustments are used to identify when the meat is spoiling to a similar state of 1, 5, 10, 15, 20 and 25 PPM of ammonia in the atmosphere. Assuming only ammonia is released, the 1 PPM region may be used to activate the software application to look more closely at the resistance curve and identify (in addition to time taken of the first detection point) how far the meat is within its spoiling processes.

Figure 61:
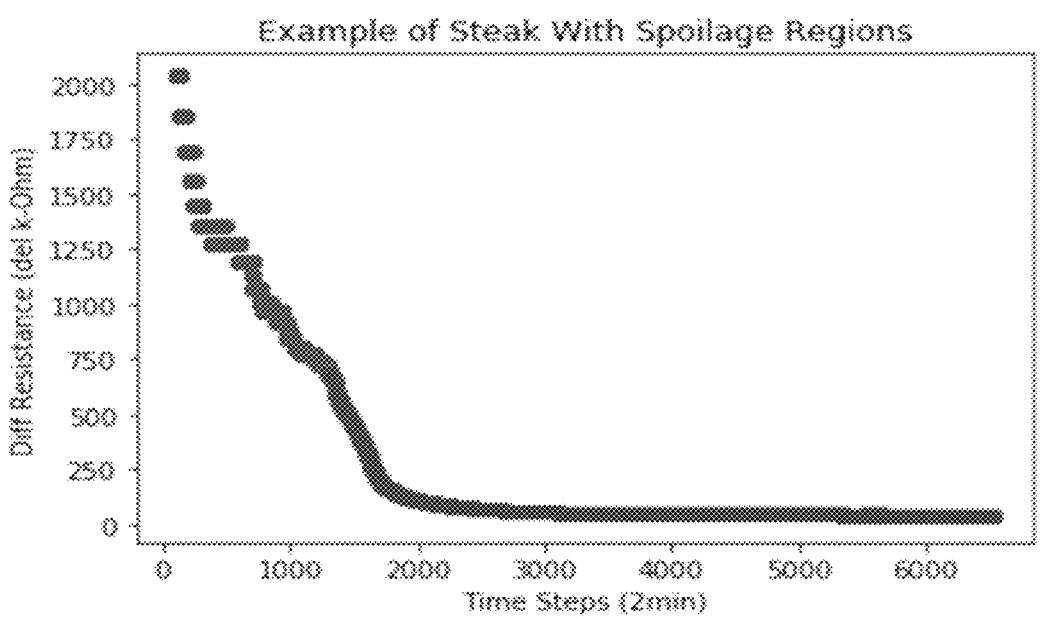
FIG. 61 is a graph showing spoilage regions for steak forming one aspect of this disclosure.

FIG. 61 shows the areas that are within the known spoilage regions. Due to the issues with variable resistance values, the measured resistance values are used to help identify the specific onset of ammonia, as well as ratios and other patterns (such as gradients or rate of change deviations) to more accurately identify the regions believed to be more likely effected by ammonia. These regions are highlighted in red, while green represents the safer regions that are merely experiencing equilibration.

There is no differentiation between a harmful spoilage state and an acceptable state where the food is still savable and edible. To isolate the specific phase of the spoilage process, additional processing is needed. There are two ways that complement each other for this that will be shown here for demonstration purposes. However, the solutions used to describe these phases are not limited to these examples.

Figure 62:
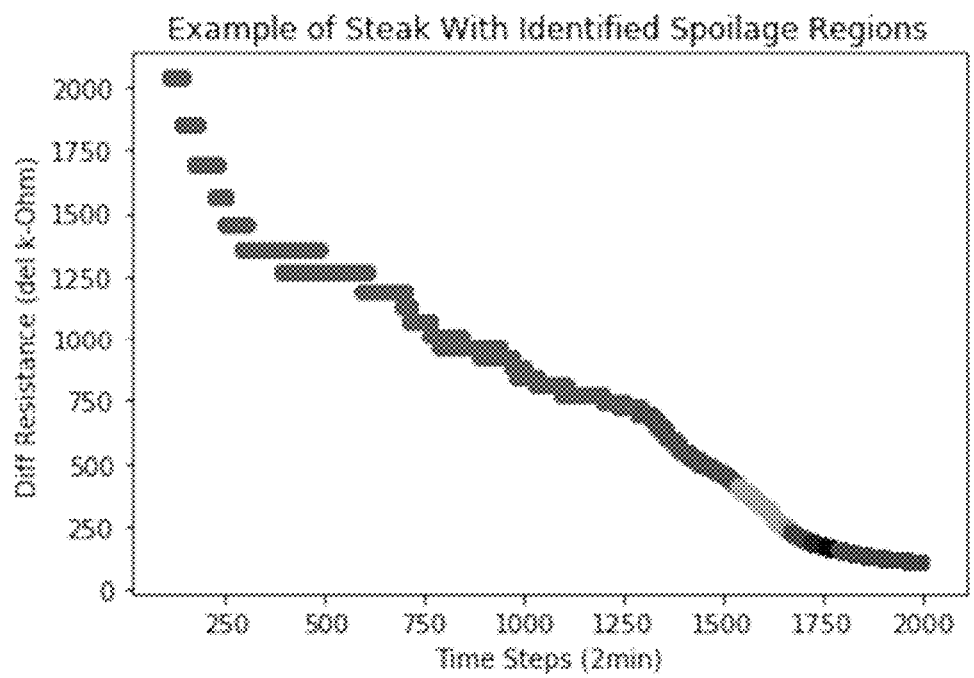
FIG. 62 is an expanded view of the spoilage regions from FIG. 61 detected by the sensor forming one aspect of this disclosure.

The first method follows the example shown in FIG. 61, using a more detailed analysis of the rates of change experienced by the resistance changes and the ratios at particular stages demonstrated by the results shown in FIGS. 30-33. Specifically, FIG. 62 illustrates an expanded view of the spoilage regions detected by the sensor. The colors represent the spoilage state of the meat in ammonia by PPM: Blue: 0, Green: 1, Yellow: 5, Cyan: 10, Red: 15, Navy: 20, Black: 25, Magenta: 30+. In more detail, FIG. 62 shows the first 2000 time steps with the different tested ammonia values and their corresponding estimated regions. It should be noted that the sensitivity of the sensor has shown that as the PPM value increases, the relative change resistance that occurs reduces. This is clearly reflected in the ever-shrinking area of color regions. These differences allow for a clearer and more well-defined spoilage alert system.

The second method of analyzing the spoilage is to use the time-stamp dates in conjunction with the onset of the earliest detection of the resistance deviation from natural baseline equilibration process (described above). The emission of gases illustrated in FIG. 28 shows the emission trend of TVB-N's normalized against time. This equation ($Y=M_2X_2+M_1X+M_0$, with X representing normalized time and Y representing the TVB-N values detected) can be rearranged to solve for X. This requires that the onset of the detected changes of the resistance rate as well as the ratio and rate of change values, can be used to approximate where on the spoilage timeline that particular time-stamp should be located. The approximate spoilage time (taken experimentally for different meats at different storage temperatures) experienced by the perishable item once the decay process has started is used to estimate how long the food has left before it reaches a toxic or harmful level of spoilage.

For example, given that approximately 1 PPM of TVB-N is detected by the sensor, its place on the curve is relatively fixed, which indicates that once the processes has started and assuming the storage temperature is within the tested and calibrated range (4-30° C.), an estimation of time remaining from optimal to poor storage conditions may be calculated (the warmer it is, the more rapidly the food would spoil resulting in a shorter approximate spoilage time range). This process can also be repeated with other PPM values as the approximate location of detection with regards to its concentration of the TVB-N emission graph (FIG. 28).

One advantage to this particular system is that if multiple resistance readings are recorded and those values are time-stamped, any variation experienced by the decaying food (unusually slow or fast emission changes) can be used to rescale the approximation of time remaining until the point of harmful spoilage occurs. This results in each food item being scanned effectively having its own unique "use by"

and/or "consume by" date that is specifically and uniquely linked to that one item due to the unique identifier. Further, the coefficients for each meat or decaying food type would need to be determined in order to use the normalized time coefficients to create and adaptive consume by date.

Figure 43:
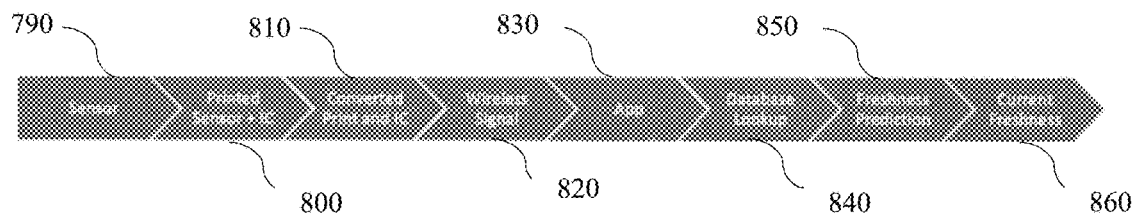
FIG. 43 is a flow chart showing an exemplary implementation of a method of using a freshness sensor device forming one aspect of this disclosure.

Turning back to FIG. 43, a flowchart showing an exemplary implementation of using the freshness sensor device 10 is illustrated. In step 790, a sensor 20 or printed sensor material is first provided and has a configuration for interacting with its environment. In step 800, the IC 40 is queried or induced by an outside or external source. In step 810, upon detection of an analyte of interest, the sensor 20 transmits sensor information that is received and read by the IC 40 through the printed circuit, wherein the information is converted into a binary response or digital interpretation based on the circuit being used (binary switch or A/D) and is stored in memory. In step 820, upon conversion, a wireless signal is sent from the printed device/tag to a receiver or reader device, such as one running the software application. In step 830, the application decodes the signal and converts it to usable information. In step 840, once decoded, the useable information contains a unique identifier that links to the item's specific information via a database. In step 850, the latest freshness reading data is stored and registered with a time-stamp to allow the application or retail store system to match the freshness trend with the stored predicted trend for that perishable item/food type. In step 860, a current freshness value may be calculated and displayed on the application or stored in the store system such that it can be referenced to the use-by-freshness point (the point at which the gasses indicate it is possibly not fresh enough to consume).

Figure 74:
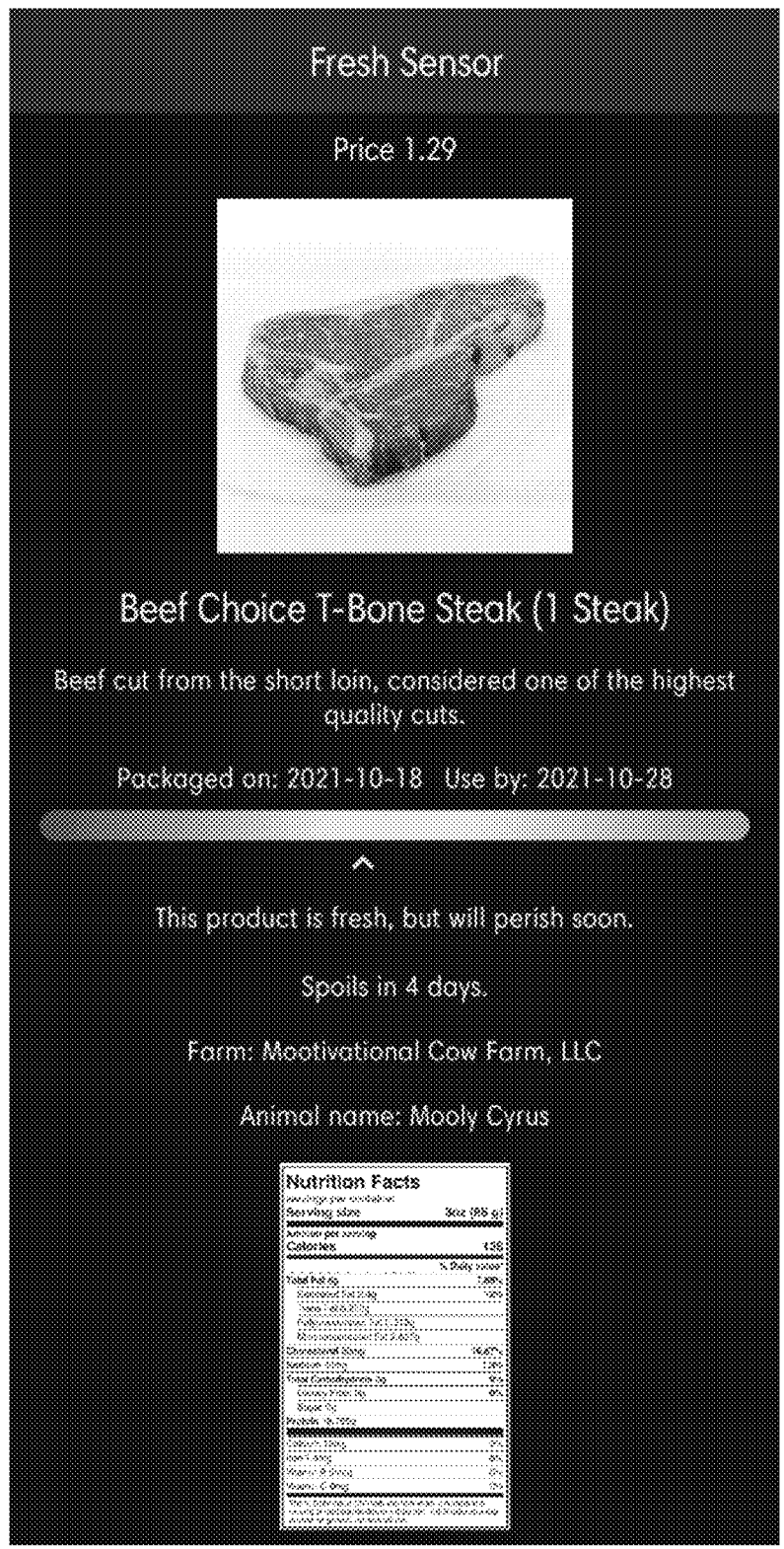
FIG. 74 illustrates a representative view of the display screen view to a consumer of the freshness value determined by the software application forming one aspect of this disclosure.
Figure 75:
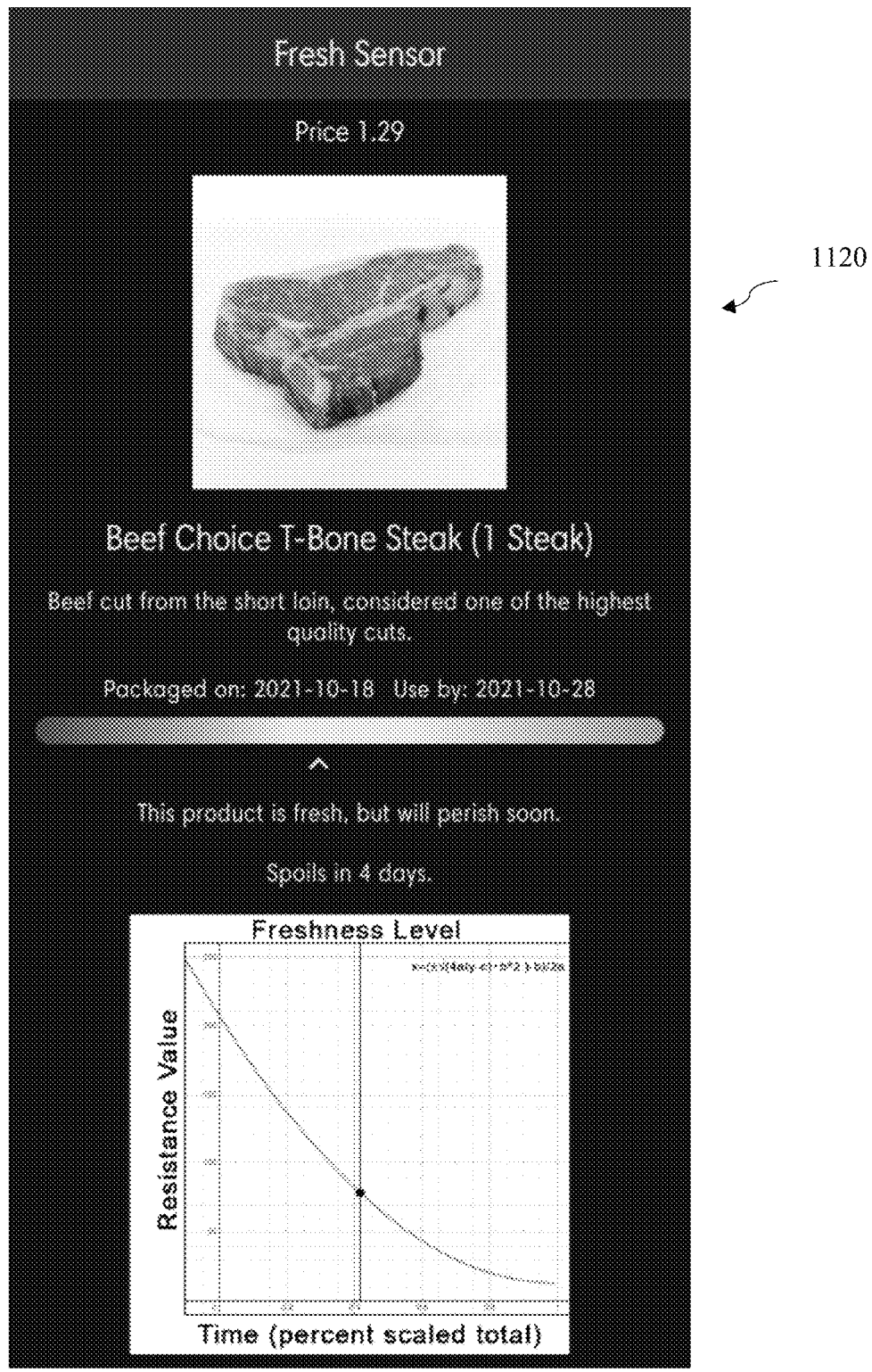
FIG. 75 illustrates a representative view of the display screen view to a retailer of the freshness value determined by the software application forming one aspect of this disclosure.

For example, FIGS. 74 and 75 illustrate representative views of the display screen view to a consumer 1110 and retailer/associate 1120, respectively, of the freshness value determined by the software application. Specifically, in FIG. 74, the consumer view 1110 of the software application shows customer-relevant information pertaining to a product and its assigned freshness sensor. Once scanned, the tag's unique ID allows the application to look up the product information that pertains to the assigned product, such as product name, price, and nutritional information. The current resistance reading is also pulled from the tag when scanned, which in this example is processed through the corresponding algorithm and is translated to a text description, days until spoilage, and an indicator on a red-yellow-green freshness scale. Additional supply chain and traceability information may be included here, as evidenced by the package and use by dates in the example. This could also include information up to the farm level where applicable. It should further be appreciated that other data may also be provided on the consumer view display screen.

Figure 76:
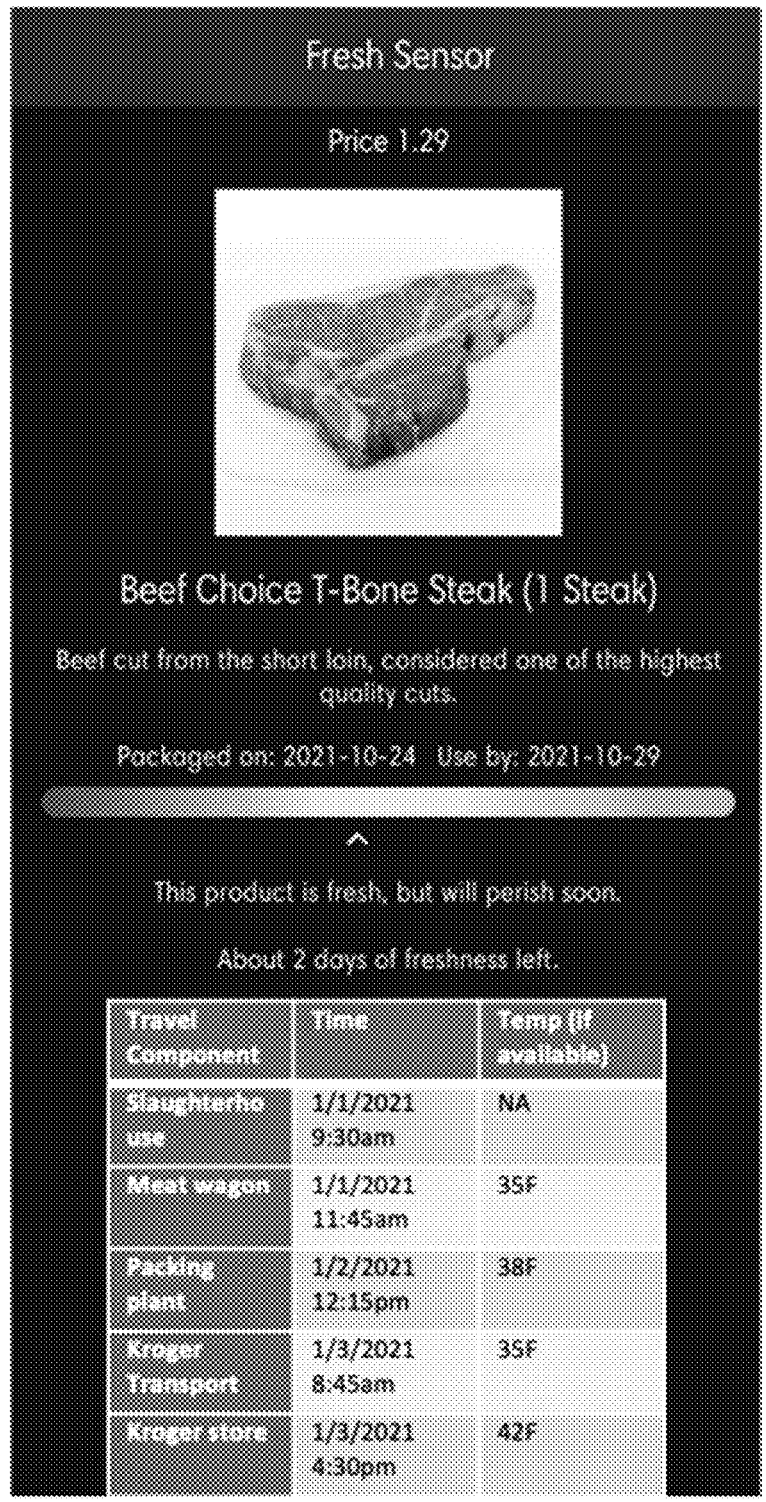
FIG. 76 illustrates another representative view of the display screen view to a retailer of the freshness value determined by the software application forming one aspect of this disclosure.

Turning to the associate view screen 1120 in FIG. 75, the associate view may include all of the same information provided by the consumer view 1110 to facilitate employee activities, including assisting customers that may not have an NFC-capable smart phone. In this view, the nutritional fact information, farm and animal information is omitted, but again all of this information may be included on this screen as well as additional information to further enhance the associate experience. For example, a historical freshness reading graph to show the trend of freshness over time is displayed on screen 1120, which can be leveraged by employees at any stage to ensure freshness of a product. The graph is also able to demonstrate (using color coded boundaries) graphically where the product is within its freshness life. Employees can use this data when receiving product from the farms, providing the opportunity to reject products that do not meet the retailer's freshness standards. The historical readings, as perhaps shown best in the alternative associate view 1122 provided in FIG. 76, also allow new levels of traceability, helping to track down any unnecessary negative impacts to the freshness of a product along its entire journey. These tags also give the retailer the capability of location positioning and inventory tracking, which can also be presented to and used by employees.

In one particular embodiment, the intelligence of the system is completed on the application and server side such that the freshness sensor device is maintained as simple as possible to reduce size, complexity and costs. The resistance reading from the sensor is converted to a digital signal that may be retrieved by the application. This digital value is applied to a freshness equation stored in the software application to calculate the amount of freshness left in a product. The services and application program interfaces (APIs) allow the results of the equation to be mapped along with prediction trends customized for each perishable item/type. Advantageously, this allows for a prediction of the number of days remaining until spoilage, providing a more useful, accurate replacement of "use by" or "sell by" dates currently used.

Figure 44:
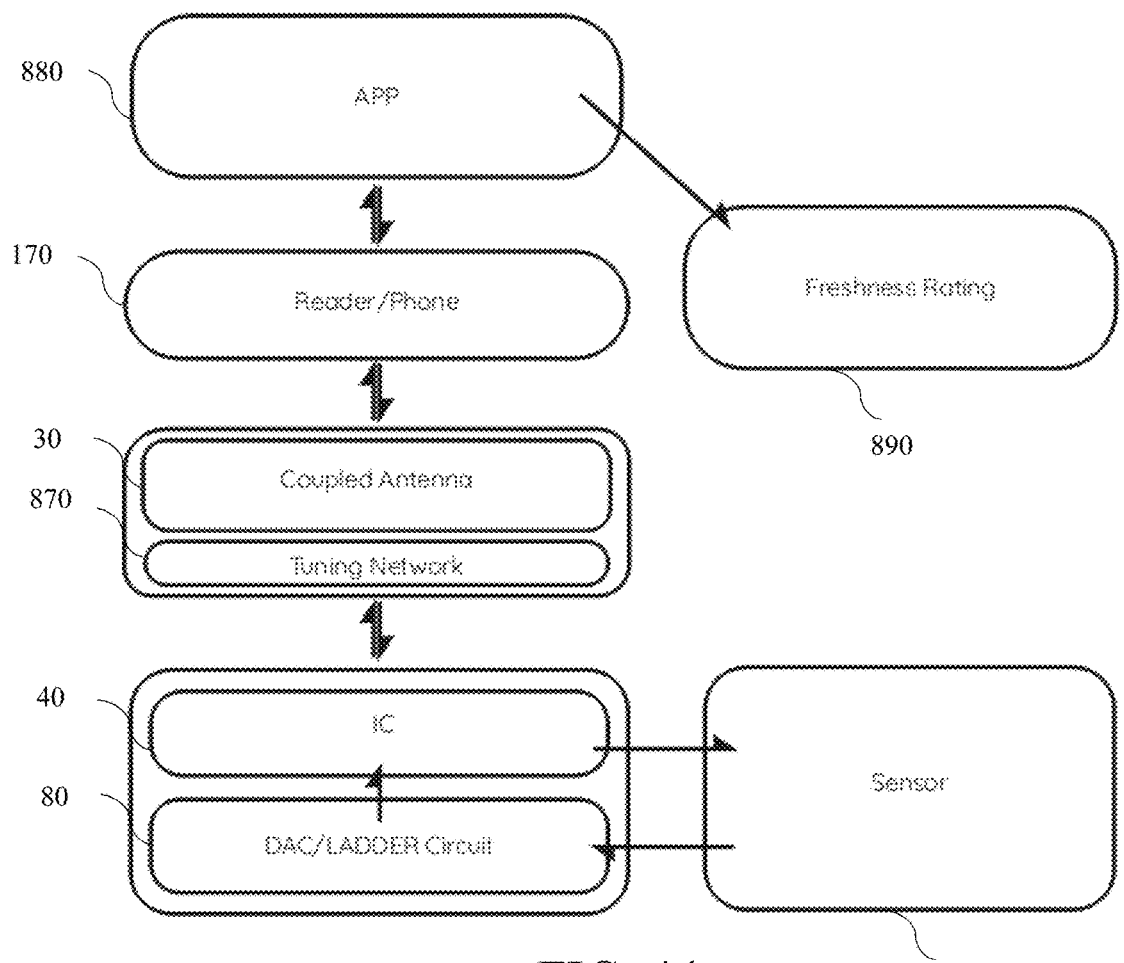
FIG. 44 is a flow chart for the freshness sensor device and related application processes from the consumer's perspective forming one aspect of this disclosure.

FIG. 44 illustrates a flow chart for a method of using the freshness sensor device 10 and related application processes from the consumer's perspective. Upon detection of an analyte of interest, the sensor 20 transmit sensor information that is received and read by the IC 40 through a printed DAC circuit or ladder circuit 80. The sensor information is tuned (step 870) and transmitted by the antenna 30 to mobile computing unit or receiver, such as a mobile phone or tablet having a reader device, such as one running a software application. The application 880 converts the sensor information into a freshness rating 890, which may be stored for use in future calculations and displayed on the application to the user. In some embodiments, the user interface of the application provides a color scale for freshness, written warning and/or a written time until spoilage.

In certain embodiments, the sensors and devices may be further integrated with other consumer devices and systems to provide an overall system for determining the freshness of a perishable item. For example, the NFC/Bluetooth aerials may interact with consumer devices, i.e., mobile phones, smart watches, or tablets which have built-in NFC and Bluetooth readers. The RFID, Bluetooth, Thread, Zigbee, and other 802.15.4 and 802.11 aerials can interact with the store's built-in access points. In some embodiments, the consumer and store system's interactions may be combined in a single device. For example, one antenna may be configured to communicate with both long-range (RFID) and short-range (NFC) protocols or, in the alternative, two antennas to address each case individually. RFID, Bluetooth, and Zigbee Green Power have shown to be viable avenues with passive interactions at range, and the others with the introduction of an alternative power source.

To develop the integrations into other systems, additional software enhancements or tools enable the connection of the tag's aerials to the retail database systems that can track and identify unique items when scanned. Specifically, each tag may be given a unique product and item code embedded into the device during its initial "activation." Upon further passive or induced activation, the unique code can be referenced by either the store, associate, consumer to identify the item. This code is then used to extract the item information and freshness of the product (when relevant).

It should be appreciated that this data is particularly relevant for and to be integrated into retail store inventory, production planning, checkout out, logistics, warehouse inventory, pickup and delivery systems. In certain embodiments, this may be achieved by an access point or associate reading device querying the tags, reading the unique ID and freshness reading, and sending this information over an existing data management platform. The data management platform will store this information in a server for historical usage and also to trigger events for the other relevant applications to consume. Advantageously, this provides an opportunity to develop additional tools and web applications to review and monitor freshness at broader scales, including store-wide, division-wide, and enterprise-wide.

For the consumer interactions in retail stores, the freshness application is designed to allow customers to scan these devices, and retrieve the unique IDs and current freshness reading. This data would similarly be transferred to the store servers, and the application will use the stored equations (detailed above) to display a human-readable freshness reading and predicted time until spoilage on-screen for the customer.

It is further contemplated that in home use of the devices and sensors described herein will allow such devices and sensors to integrate and "communicate" with smart appliances as well, such as smart refrigerators. The integration would automate the scanning of the sensors and provide data needed to remind the customer of food that needs to be used before spoilage. In other embodiments contemplated herein, the devices and sensors may be integrate the RFID tests with the "take home" meal kits. Furthermore, it is contemplated that providing inventory monitoring in the home and store, as well as storage of cooking instructions, as well as freshness capabilities. Further integration could be accomplished by enabling automated cooking when smart appliances/connected smart apps scan the device and all relevant appliances in the home are turned on to the appropriate settings. Ultimately, a fully automated appliance may run an end-to-end cooking process if the packaging were to be compartmentalized.

In certain embodiments, each reading of a freshness sensor device may be captured by software services and saved to the database to provide historic reading trends and insights for an end user, such as retail store. These freshness readings captures may be paired with location, time-stamps, and other data to generate additional insights for utilization with other systems. For example, upon reading a freshness reading, a request is made to upload to the reader device all the information associated with that specific item. This information can include but is not limited to the date of processing and packaging, initial tag response (resistance), item historic information (farm of rearing or growth, slaughter or picking information), temperature tracking of items throughout the retail chain until the point of scanning and all the time-stamped data of these events. This information is uploaded to a mobile device and displayed to the consumer or a store associate. In some embodiments, upon pairing the data with consumer loyalty information, the data can further be used for food recalls.

Once the consumer downloads the data to their personal device, the item's type, i.e., pork, fish, beef, etc., can be used to identify which spoilage equation is applicable to the particular food type. For example, FIG. 28 shows the spoilage effects for tilapia and is representative of how a specific meat's spoilage rate is expressed mathematically as a polynomial. The downloaded data contains the coefficients for the polynomial as well as the estimated total spoilage time for that particular food item stored at multiple temperatures.

During the spoilage process, data recorded by the consumer can then contribute to the spoilage prediction events and once the item is no longer scanned (assuming that the after a certain number of days the item will either be frozen for long-term storage or consumed), the new data collected by the consumer can then be submitted or uploaded to the device and then to the original data hub to improve and validate the system.

Turning to the production of the sensors and devices described herein, a number of printing processes are known. Generally, rotary textile or wide web screen printing operations, such as registered printing and curing or drying of films are known. Similarly, with respect to electronic device manufacture, pick and place operations and sheet fed circuit printing are known. Similarly, in some sensor manufacturing operations, it is known to use paper as an analytic base. However, the combination of these operations into a single manufacturing process to cheaply and quickly produce functional sensor devices is not only not known, but highly desirable for the reasons detailed herein.

Figure 45A:
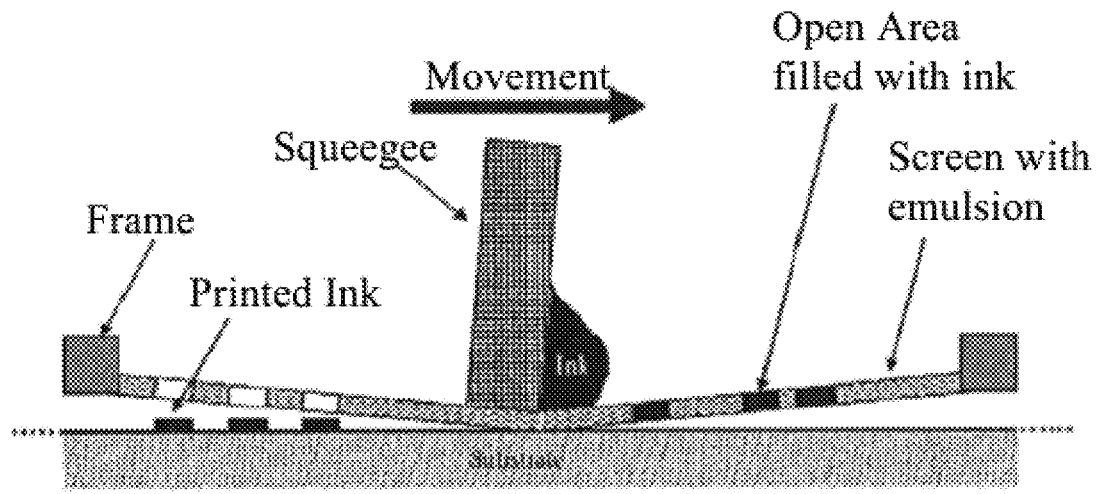
FIGS. 45A and 45B are schematic diagrams showing exemplary rotary scale printing technique (see "Recent advances in upscalable wet methods and ink formulations for printed electronics." J. Mater. Chem. C, 2014, 2, 6436-6453 https://doi.org/10.1039/C4TC00618F) forming one aspect of this disclosure.
Figure 45B:
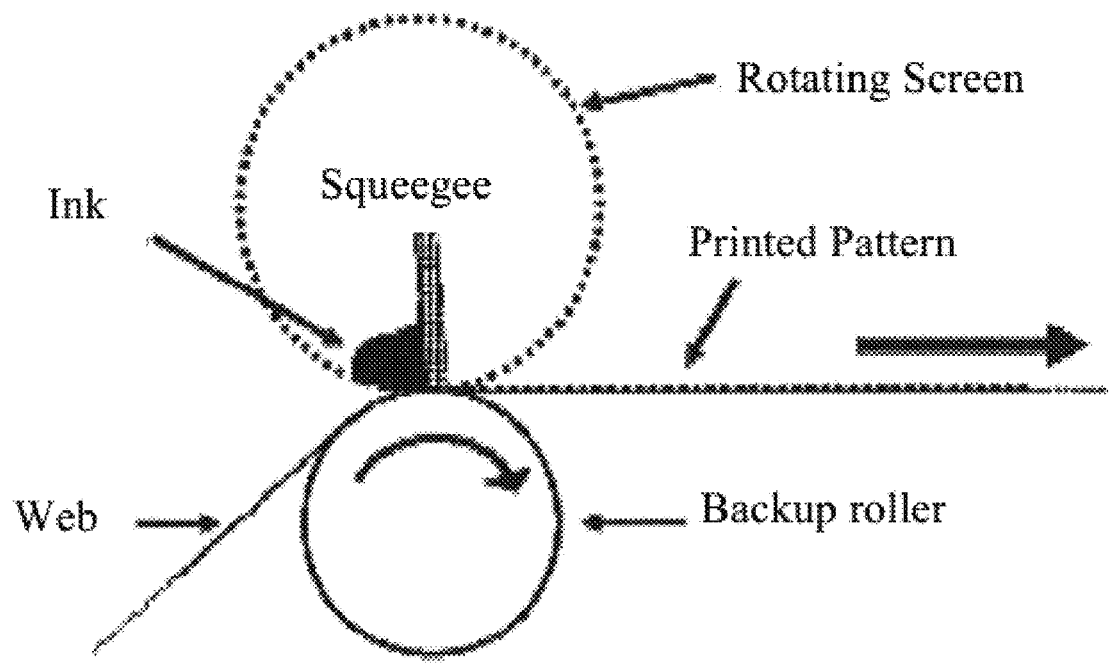
Figure 46:
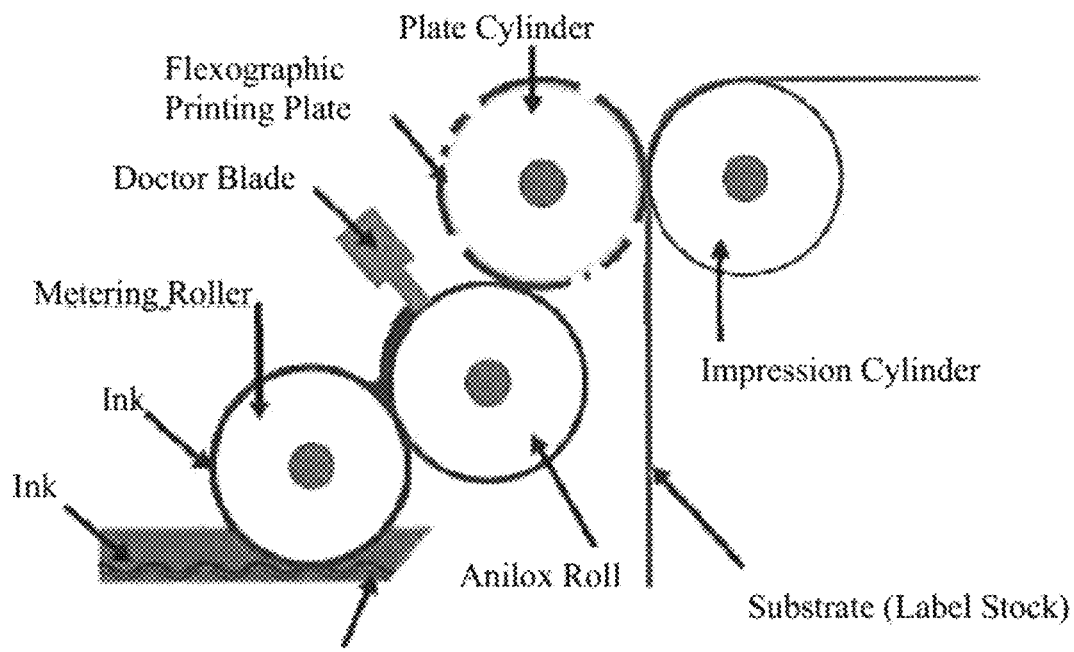
FIG. 46 is a schematic diagram showing an exemplary flexographic printing technique (see https://www.ndigitec.com/news/what-are-some-of-the-most-popular-printing-methods/) forming one aspect of this disclosure.
Figure 47A:
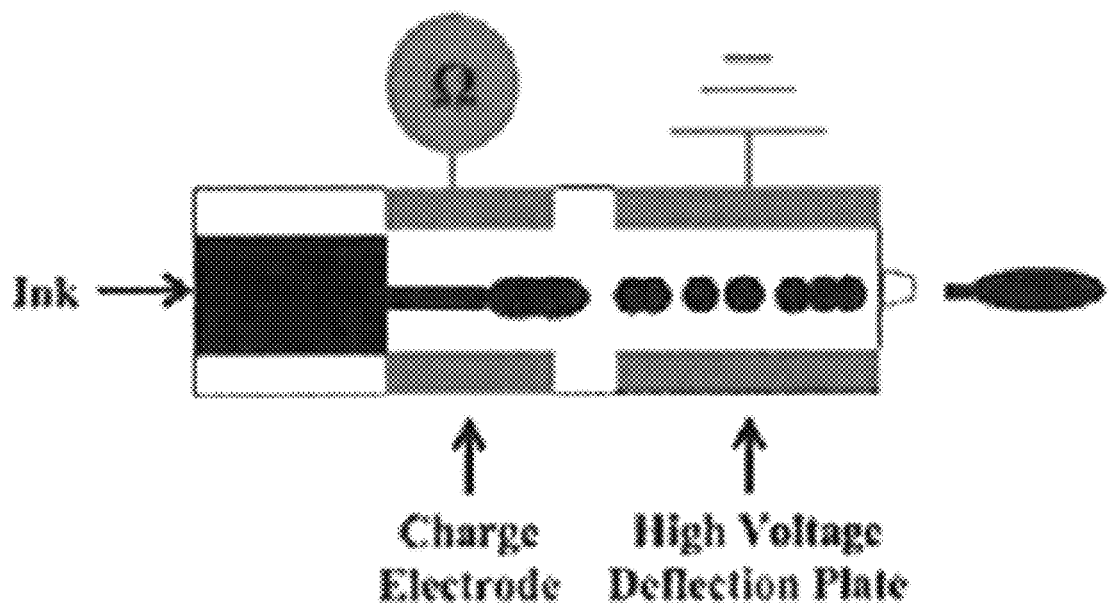
FIGS. 47A-47D are schematic diagrams showing exemplary drop on demand/inkjet printing technique (see "Inkjet printing for Radio (meaning all components except sensor, IC and A/D) fabrication: Combining chemistry and technology for advanced manufacturing. Lab on a Chip." Li, Jia & Rossignol, Fabrice & Macdonald, Joanne. (2015). 15. 10.1039/C5LC00235D.) forming one aspect of this disclosure.
Figure 47B:
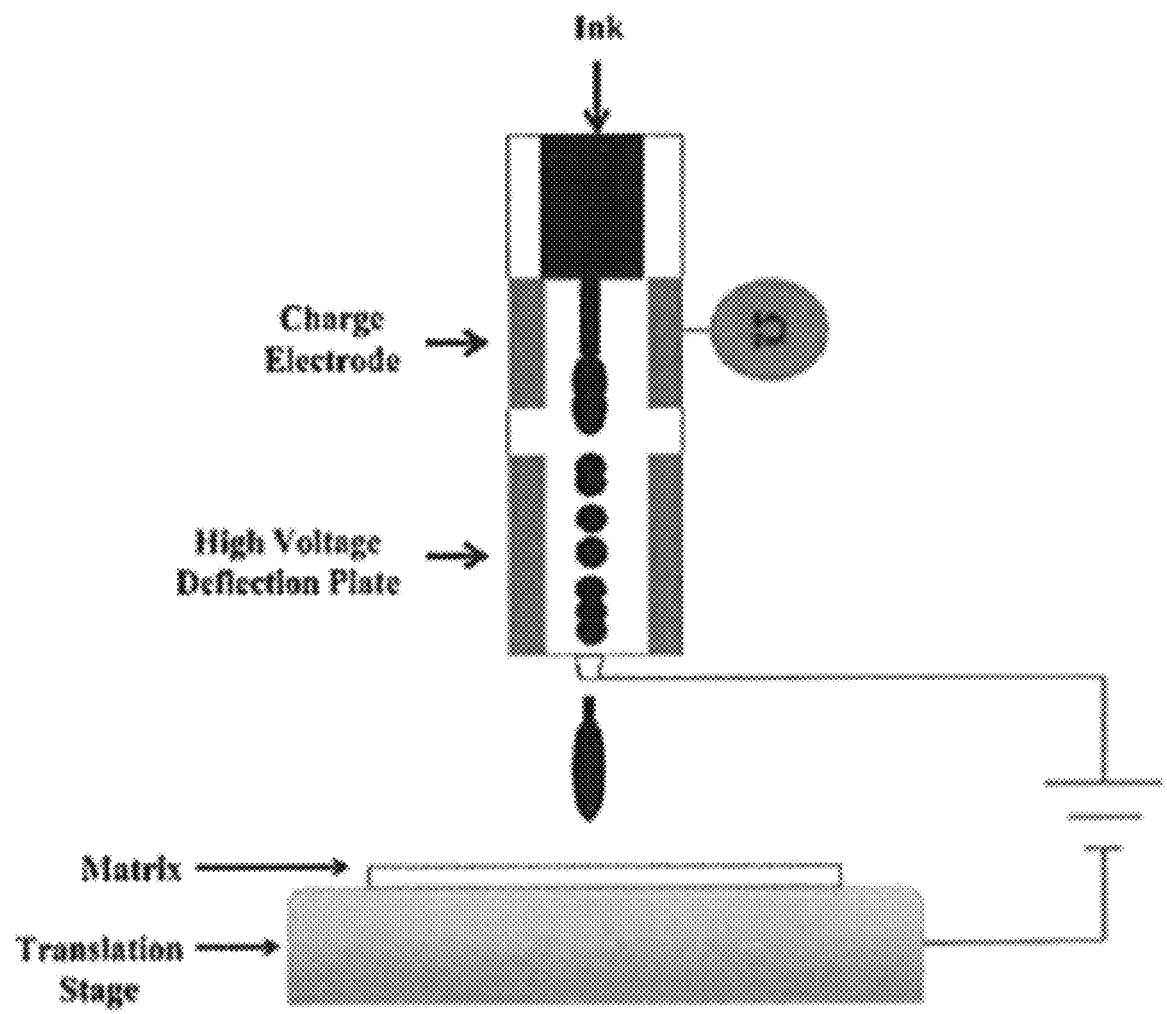
Figure 47C:
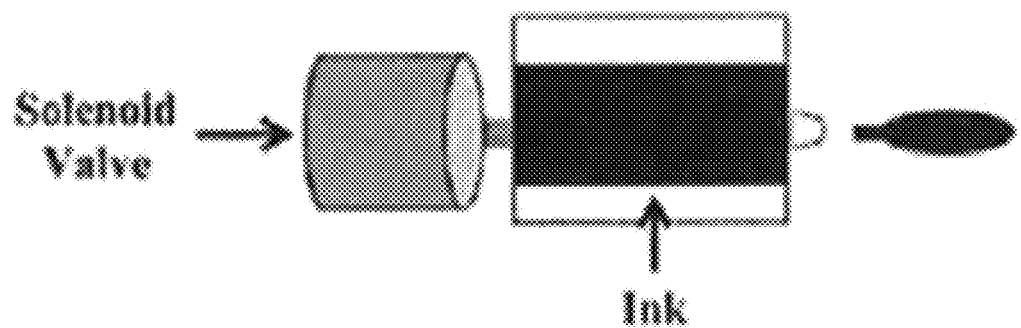
Figure 47D:
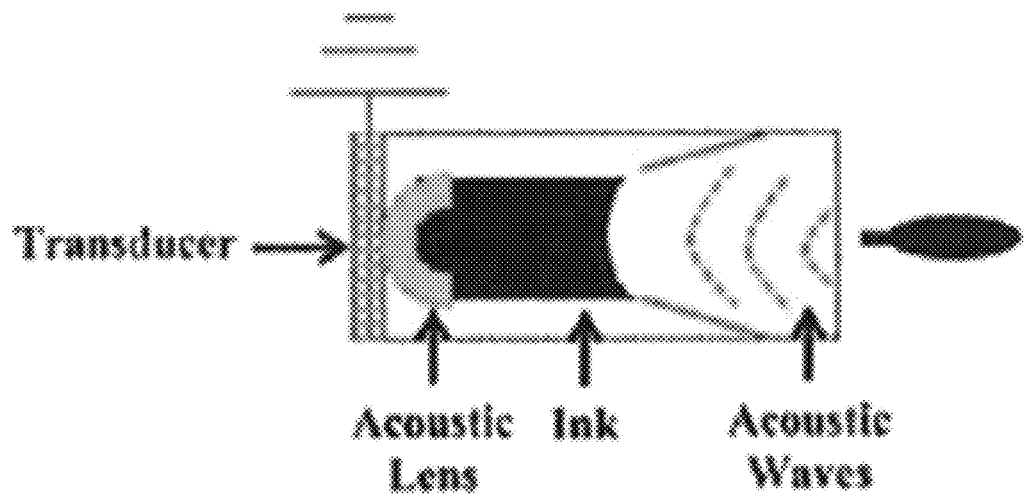

It is desirable to utilize printing processes to produce the devices as efficiently as possible, both in terms of time and cost. It is contemplated that the printing processes range from physical to digital and include rotary screen print, flexographic print, gravure printing, lithography, and drop on demand and xerographic printing. Various embodiments of these printing processes are shown in FIGS. 45-47. For example, FIGS. 45A and B illustrate schematic diagram of an exemplary rotary scale printing technique. FIG. 46 illustrates a schematic diagram of an exemplary flexographic printing technique. FIGS. 47A-D shows a schematic diagram for an exemplary drop on demand/inkjet printing technique.

Figure 48:
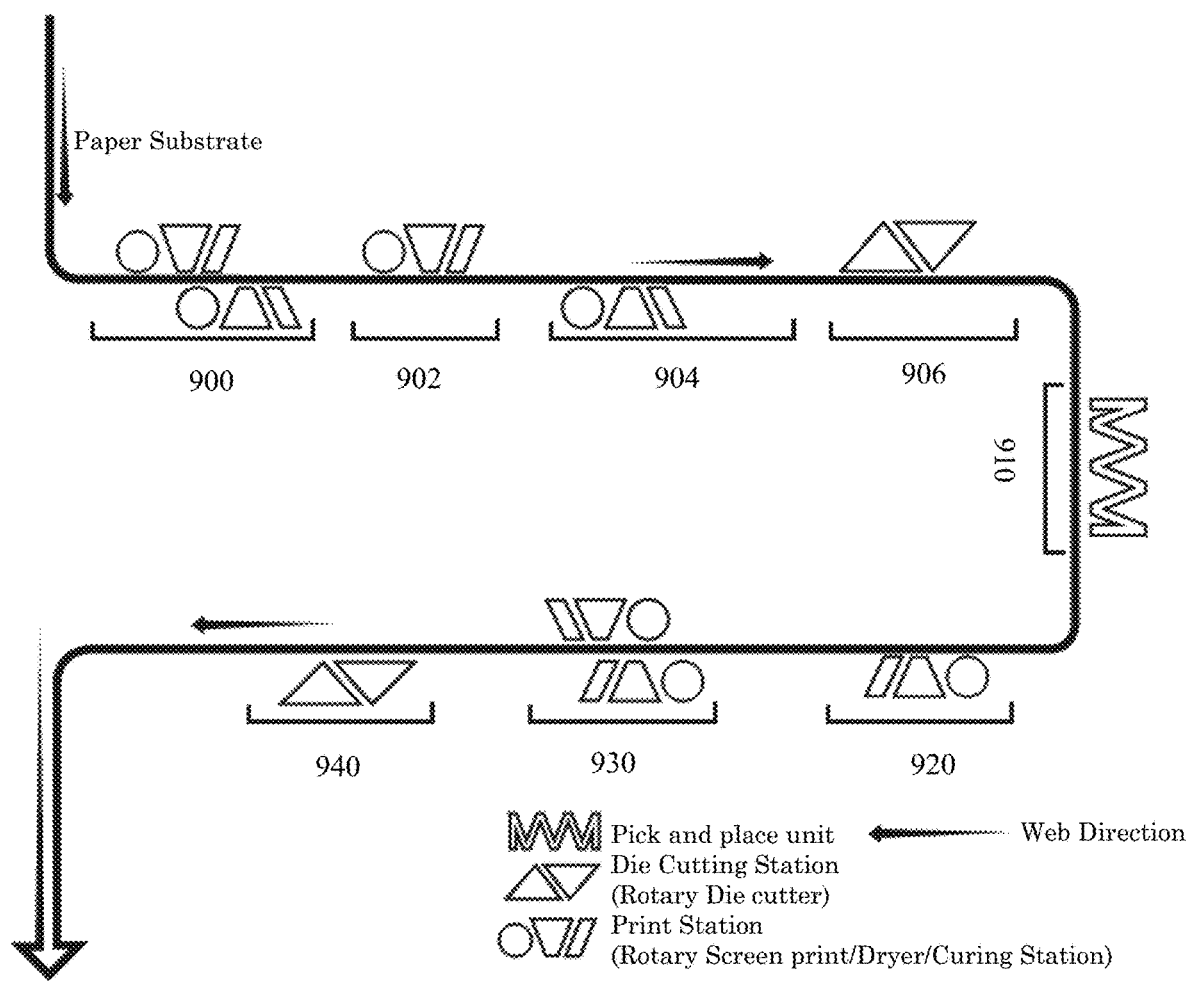
FIG. 48 is a flow chart of the rotary screen print process forming one aspect of this disclosure.

The method for creating functional electronic sensor devices described herein reduces complexity relative to other approaches in the market, which allows for cheaper and faster fabrication of IoT devices. Advantageously, the method combines approaches from textile/packaging rotary screen printing field, conventional electronics pick and place operations, printed sensor materials field, material handling, and wireless device encoding. The freshness sensor device 10 may be developed both by using ink-jet printing capabilities with a print press or rotary screen print process as illustrated in FIG. 48. It should be appreciated that these devices may be developed via a regular print screen process as well.

The process illustrated in FIG. 48 is significantly different to how known NFC/RFID tags are typically produced. Indeed, while this screen press process is known, it has not been usable in the past for these types of devices because the known inks and technology of the print/screen press process have been unable to deliver satisfactory results. Thus, current methods utilize ink-jet printing only. Importantly, print press or rotary screen printing processes are typically only used for newspaper, textile and commodity printing, not electronics or electronic sensor device printing.

Importantly, the application of a rotary screen print process dramatically reduces production costs, while allowing large scale production, i.e., roll to roll manufacturing. Again, the device/tag 10 may be developed on a single sheet of paper substrate so that the fabrication process allows for an enhanced speed of production over currently used methods, such as the inkjet print process that is commonly used for similar devices. Indeed, the sensor 20, IC 40 (including the electrical circuitry, capacitors and the like) and antenna 30 may be printed on a single layer. Because only a single sheet of paper is utilized, it can be incorporated directly into the packaging and labeling process as an additional layer without significantly affecting the packaging process.

As shown in FIG. 48, the rotary screen print process is performed on a paper substrate. Specifically, an initial cellulosic permeable material may be utilized as a mechanical function layer, i.e., a roll of paper being fed into the press. Optionally, a pressure roller may be used as a smoothing pass on the surface of the paper. At step 900, a layer of dielectric is printed on the surface of the paper, but an unmodified region is left for printing of the carbon sensor material. The dielectric is dried and otherwise cured. Importantly, the dielectric functions as a method for reducing water permeability of the substrate and smoothing layer for conductive print. At step 902, a graphene/carbon sensor material is printed on the unmodified region and then dried. Step 904 is a front and back electrical print, wherein a conductive ink is printed over the dielectric layer in a desired circuit pattern. At step 906, a registered die-cutting operation is used to cut vias in the overall design (the tag perimeter is left intact). The IC chip is next picked and placed in registered manner to the roll at step 910. The next step 920 involves via and IC connections are connected by drop on demand ink jetted conductive material followed by a non-conductive immobilization coating printed over the entire circuit and cured at step 930. At step 940, the completed sensor tags are then die-cut in a registered manner from the overall web. At this time, tags are flashed and checked for function. The function test includes confirmation of the unique identifier (UID) of the label and confirmation of sensor function. Finally, the tags are collated for delivery to labeling facilities in preparation for conversion to consumer facing tags.

Figure 49:
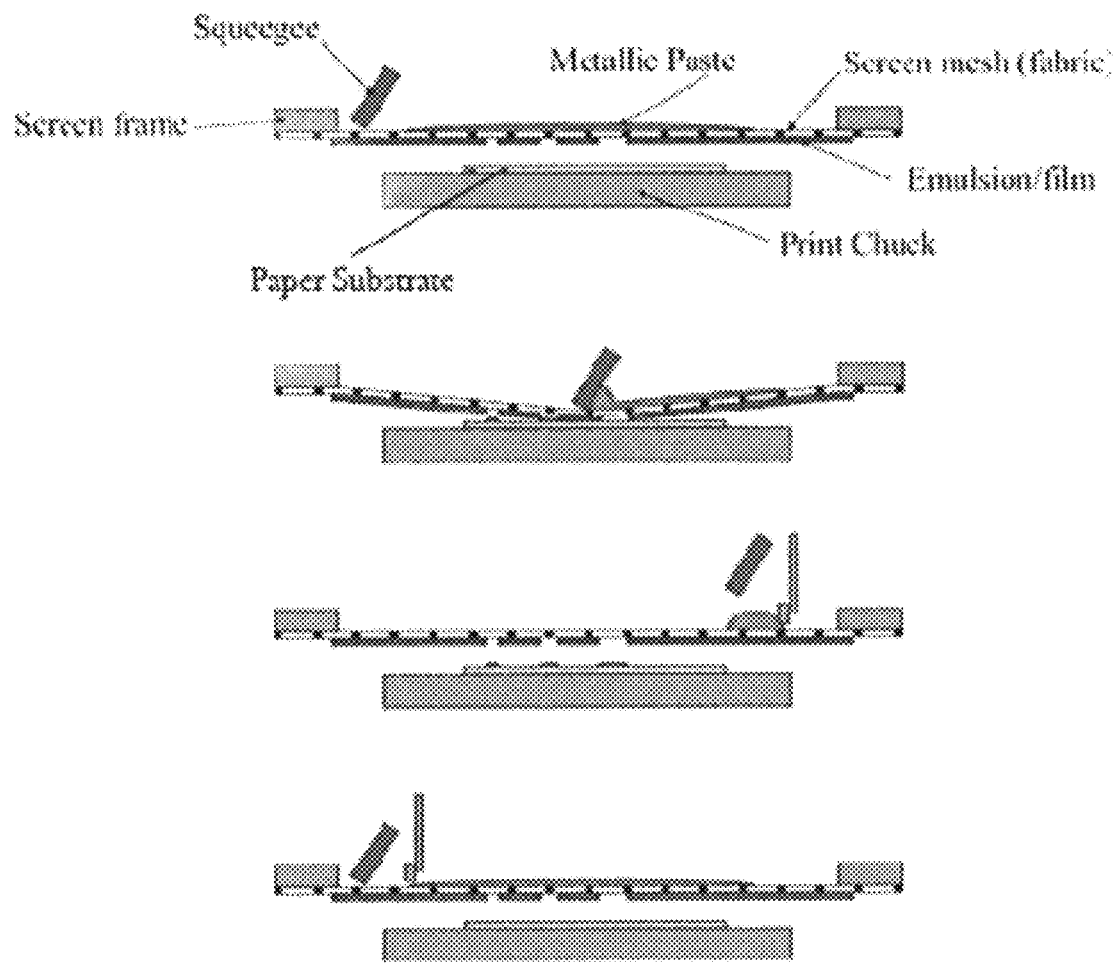
FIG. 49 is a schematic diagram showing another printing technique (see "Contact Definition in Industrial Silicon Solar Cells." Caballero, Luis Jaime. (2010). 10.5772/8075.) forming one aspect of this disclosure.

Additionally, this method of production is able to rapidly produce both the freshness sensor tags discussed here but is also relevant to the production of any RFID, NFC or other electronic passive or active electronic device that can now be produced using this fabrication and production method. An example of the pilot scale process is illustrated in FIG. 49. Tables 4 and 5 show lists of the materials and supplies used in two different example:

TABLE 4

| Item | Materials |
|---|---|
| 1 | Cellulose Paper |
| 2 | Carbon Ink |
| 3 | Screen for printing |
| 4 | Teflon Tubing ¼ Inch OD |
| 5 | MKS MFC Ammonia 1000 ppm At 100 sccms |
| 6 | MKS MFC Nitrogen at 1000 sccms |
| 7 | MKS 4 port controller |
| 8 | MFC controller cables CB259-5-10 CABLE, PR4000, 627 TYPE × 2 |
| 9 | Humidity Gas Sensor (HDC2080DMBT) |
| 10 | Humidity Gas Sensor Controller (HDC2080EVM) |
| 11 | Gas Chamber Clear PVC Pipe |
| 12 | 4 × Gas Chamber White PVC screw cap ends |
| 13 | Chromatography paper |
| 14 | SSI Swagelok Fitting, Male, ¼ in. Tube OD × ¼ in. Male NPT |
| 15 | SS Swagelok Tube Fitting, Union Tee, ¼ in. Tube OD |
| 16 | 4 × ¼ inch Unions |
| 17 | 2 × ½ inch unions |
| 18 | 20 Teflon Ferrules |
| 19 | 4 × ¼ inch Nuts |
| 20 | Ammonia gas regulator |
| 21 | Control Board Kit Arduino beginners kit |

TABLE 4-continued

| Item | Materials |
|---|---|
| 22 | 1000 ppm NH3 Calibration gas in N2 |
| 23 | NH3 Sensor_Winsen_Compatable with ardunio board |
| 24 | Home Depot Pipe endings and 3 inch pipe for bubbler |

TABLE 5

| Item | Material |
|---|---|
| 1 | Roll Whatman 597 grade filter paper or similar paper on 6" or other commodity core |
| 2 | Dielectric printing ink, such as Dupont 5018 |
| 3 | Silver, copper or carbon conductive material |
| 4 | Rotary screen printing press such as Rotascreen. TG or SpgPrints RD8 equipped with drying stations able to be heated to 300° C. at a rate of 50 C./s |
| 5 | Pick and place machine, such as MC889 or Juki RS-1R |
| 6 | Carbon sensor material ink |
| 7 | Tooling for print screens |

It should be appreciated that many types of conductive ink may be used for creation of sensors of the type disclosed herein. In one particular embodiment, the ink used in creation of the sensors is a conductive carbon ink produced by Dupont called Dupont BQ242. Alternatively, other graphene inks, conductive polymer inks, silver inks, and gold inks may be used for the conductive circuitry.

Additionally, it should be appreciated that many types of paper may be used as a substrate for freshness sensors, including HP photopaper, marker paper, printer paper, PIM film, PET film, cotton paper, Epson photopaper, and Whatman filter paper, namely, Whatman 3001-672 Cellulose Chromatography Paper, Grade 1. Depending on the particular substrate used, different coatings may be utilized to ensure ink compatibility and desired level of water permeability, among other properties. These coatings include urethane coatings, primers, alumina and silica and starches.

Sensor designs vary in length, width and thickness of both the electrodes and the spacing. Some types of designs used for these types of devices may be linear or spiral. The variation in the size and shape of the sensor dramatically effects the sensitivity and overall charge build up that is experienced by the freshness tag. FIG. 50 illustrates representative sensor designs that may be used for the present disclosure.

Figure 51:
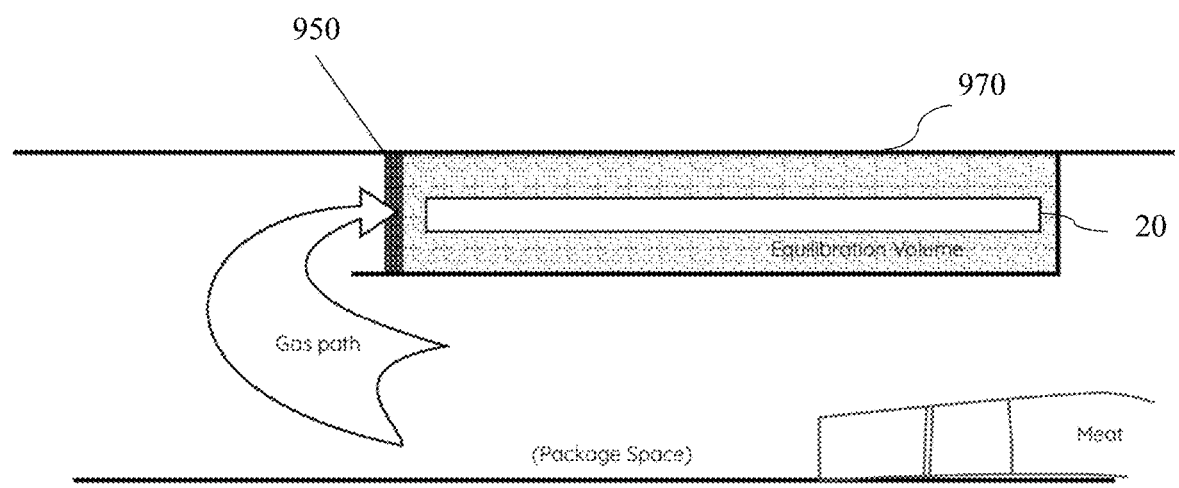
FIG. 51 is a diagram of an end capped selectively permeable membrane forming one aspect of this disclosure.
Figure 52:
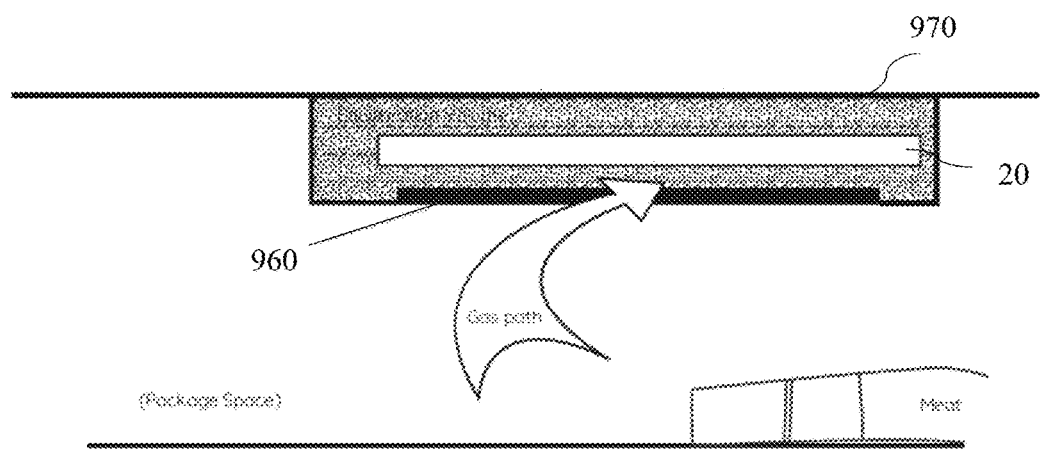
FIG. 52 is a diagram of a bottom capped selectively permeable membrane forming one aspect of this disclosure.

In some embodiments, conversion of the printed sensor material into the overall sensor structure requires placement of the IC chip and the addition of several over sheet or roll form materials. Furthermore, converted sheets can be die cut to allow creation of separated labels. These materials may include selectively permeable membranes including impermeable membranes, adhesives, and release materials that interact in different ways with both the environment and the electronic components of the sensor. For example, FIGS. 51 and 52 illustrate selectively permeable membranes that may be used with the freshness sensor device 10 disclosed herein. Specifically, FIG. 51 shows an end capped selectively permeable membrane 950, while FIG. 52 shows a bottom capped selectively permeable membrane 960. In FIG. 51, a piece of meat (M) is positioned within a package space having an impermeable outer wrap 970. A sensor 20, such as a gas sensor is positioned within the packaging and is covered by a selectively permeable membrane 950. The gas path from the meat to the sensor is indicated by the arrow and passes through the end of the sensor, wherein the selectively permeable membrane 950 is located. FIG. 52 is similar to FIG. 51, but the selectively permeable membrane 960 is positioned on the bottom of the sensor 20.

Traditional electronic sensing systems use a discrete electronic device including a rigid substrate on which surface mount devices may be attached such as a disposable, frequently packaged sensor. Indeed, the standard approach for a sensor device utilizes a printed circuit board (PCB) in either a rigid or flexible format, to which a discrete sensor structure is added. For example, an Arduino PCB may have a temperature sensor attached to it.

Figure 53:
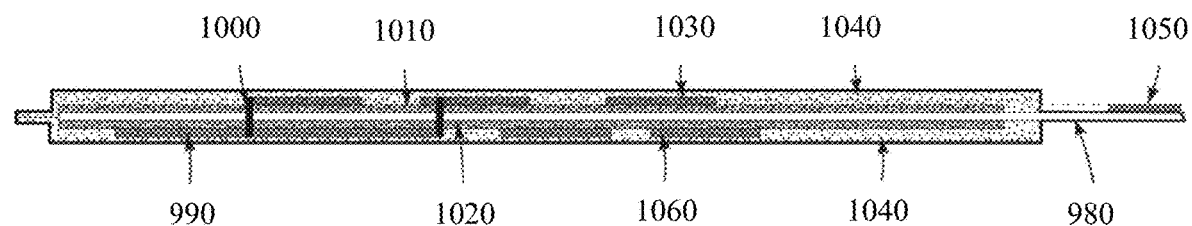
FIG. 53 is a cross-sectional view of a paper-based multi-layer substrate forming one aspect of this disclosure.
Figure 54:
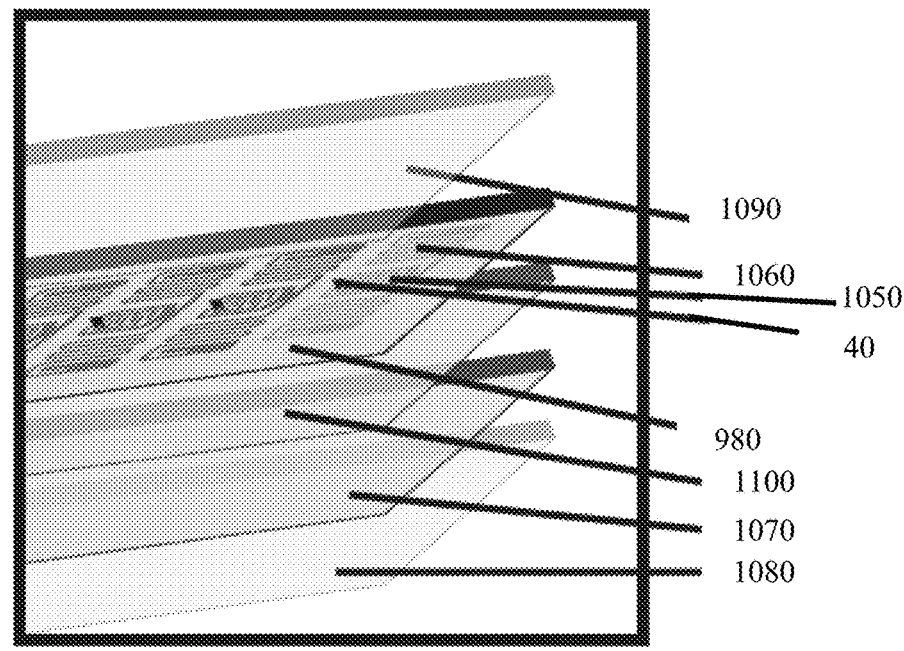
FIG. 54 is an exploded view of the paper-based multi-layer substrate forming one aspect of this disclosure.

Traditional substrates do not act as both an electronically printable surface and a water/gaseous exchange sensor. FIGS. 53 and 54 illustrate a multi-functional substrate 980 that may be used with the freshness sensor device described herein that combines the electronic functions and sensing functions on the same substrate. Of course, it should be appreciated that the multi-functional substrate 980 has other applications in a variety of different fields.

Advantageously, the substrate 980 is adapted to not only perform the traditional role of a substrate (with conductive materials and circuitry built onto the substrate) but also act as the medium and container of the reaction required to detect the presence of the chemicals produced during the decay or spoilage process. Additionally, the multi-functional substrate 980 enables both substrate deposition for electronic printable circuitry and coating free chemical sensing functions.

As shown in FIG. 53, the multi-functional substrate 980 includes an insulator, dielectric and electrically conducting layers and a separate sensor layer. Advantageously, the sensor layer may be positioned within the other functional components, i.e., it does not need to be external to properly perform. In the illustrated embodiment, the multi-functional substrate 980 includes a dielectric coating layer on a first side and the open layer needed to aid in the detection of a chemical variable on a second, opposite side. With reference to FIG. 16, RFID, NFC, IC and sensor components are printed on a single sheet of multi-functional substrate paper. The electrical contacts to the sensor may rely on the same dielectric coatings allowing for electrical current to be transferred from the electrical sensor to the IC, ground plane and antennas.

As noted above, in one particular embodiment, Whatman paper may be used as the substrate, which detects for $NH_3$ and other TVB-N's. Water is attracted to the surface of the sensor by the hydrophilic attraction of the hydroxyl groups naturally occurring in the paper. The $NH_3$ molecules interact with the water to form $NH_{4+}$ and —OH molecules. These molecules are then collected by printed electrodes and the charge distribution can be calculated by the dielectrically insulated IC circuit on the same paper substrate. At the same time, on the opposite side of the paper substrate, an antenna, IC and printed circuit is insulated from the moisture collection, chemical reaction and charge buildup experienced by the substrate at the sensor.

As shown in FIG. 53, the substrate 980 includes a printed ground plane 990, a die-cut via 1000, a front-side dielectric/smoothing layer 1010, a back-side dielectric/smoothing layer 1020, a front-side electronic print 1030, a back-side electronic print 1060, an impermeability layer 1040 and may include a sensor print 1050.

Turning to FIG. 54, one embodiment of the multi-functional substrate 980 is illustrated. The substrate has printed circuitry 1060, a printed sensor material 1050 and an integrated circuit 40 printed on it. An outer membrane 1090 is positioned over a top surface of the substrate 980. A selectively permeable membrane 1100 is positioned over a bottom surface of the substrate 980. An adhesive 1070 covers the selectively permeable membrane 1100. The outside bottom layer is a release liner 1080.

The multi-functional substrate 980 has several key properties to enable the combined function of an electronics substrate and sensor material. For the substrate to work as an electronics printing substrate, the substrate must be controlled for dielectric behavior, surface energy level and smoothness of the surface. Similarly, the mechanical properties of the substrate must be controlled for dimensional stability to prevent ink cracking and therefore a loss of electrical conductivity.

Sensing by the substrate is dependent on proper behavior in the following areas: gas exchange, water permeability, mechanical stability in presence of a solvent, water retention amount, and hydrophobicity relative to the printed ink. Many of these areas work to drive the baseline timing and overall electrical sensing performance of the sensor, which is vital to deriving useful readings. If baseline timing is not controlled, the readings would lack context and, therefore, would not be useable to describe the local environmental context. Similarly, if mechanical stability or the various interchange values of the sensor cannot be assured, the values of the sensor fluctuate and, thus, not useable for description of the local environmental context.

In certain embodiments, the multi-functional substrate works in the ranges set out below in Table 6:

TABLE 6

| ELECTRONICS | MECHANICAL | CHEMICAL |
| --- | --- | --- |
| Dielectric Property Range (k) 1.5 to 7.5 | Radius of repeatable bending (mm) <10 | Water Vapor transmission rate (g/(m2 * d)) 150 to 1200 |
| Target Roughness Range (Rz) 0.2 um to 5 um | Modulus of Elasticity of likely substrates (GPa) 0.02 to 5 | Water Hydration Range (% dry weight) 2 to 27 |
| Sensor Dyne Level Target 38-52 Dyne | Mechanically stable in hydrated state | Time to Baseline 12-36 hours |
| Electronics Dyne Level Target | Thermally stable to common heat treatment temperatures 20-200° C. | Stability of Baseline 20% or less once established |
| | | Compatibility with common electronic inks and conductive adhesive |
| | | Compatibility with common dielectric inks |
| | | Compatibility with common carbon inks |

Advantageously, the freshness sensor device 10 use with the multi-functional substrate 980 functions with minimal added complexity over the standard disposable sensor. Again, the use of the multi-functional substrate allows for both electronic and sensor functions from a single component. This combined electronic and sensor substrate simplifies the hardware required for sensing of gaseous and aqueous analytes, which, in turn, allows for lower production costs and faster production rates. Additionally, combined electronic and sensor functions in a single substrate allows for much faster continuous web manufacturing processes in place of conventional pick and place device manufacture process.

As detailed herein, the freshness sensor device 10 including multiple electrically conductive components (including multiple aerials) integrated into a single unit on a multi-functional substrate provides a number of advantages. For example, any electrochemical reaction requiring a water soluble solution or medium may be utilized by the freshness sensor device. Other electrochemical reactions may be performed when attaching specific reactants to the substrate or insulated sensor layering, which react with extremely small quantities generating potential charge distributions across the sensor electrodes. This interchangeable, small reactant-based sensor is a another versatility benefit of the present disclosure. Similarly, the application of any other thermoelectric or piezoelectric material creates the electrical potential required to activate the sensors response to the presence of a change in that environmental factor.

In addition, the method of testing freshness of a perishable item by focusing on the release of decay byproduct gasses that occur over time to determine gas accumulation rates to predict the decay rate and estimate a more accurate time until the product passes an acceptable consumption point. In addition, the use of a predictive sensor with a software application allowing for predictive tracking as well as providing the freshness level of a perishable item at any particular time is highly beneficial to both retailers and consumers and represents a significant improvement over "sell by" or "use by" dates currently on perishable items.

Specifically, the freshness sensing device is able to track and effectively monitor perishable items on a per-item basis from the point of "activation" until the package seal is destroyed or broken. The unique code applied to the individual item contains specific variants in the code that allow for the detection of the item passing its "use by" or "sell by" date when combined with the software application to track the development of the item's degradation at the store or at home. Importantly, retail stores can activate individual or multiple devices/tags at once to determine a precise inventory of all the tagged items within the store (and possible freshness of each scanned item simultaneously).

Additionally, retail stores can uniquely recall the item's history and if a product recall is issued for a product or product source, only relevant items will be targeted. Similarly, it will reduce store costs, allowing for the isolation and removal of specific items from shelves. It will greatly reduce losses in items delivered and sold by stores allowing for exact item counts to be accomplished. This in turn will allow for a more accurate stock count to reduce over and understocking products. This solution also opens up additional options for frictionless shopping in our stores. By detecting the freshness of the items in the store, additional savings can be found by dropping the price before an acceptable sales condition is breached.

One of ordinary skill in the art will recognize that additional embodiments and implementations are also possible without departing from the teachings of the present invention or the scope of the claims which follow. This detailed description, and particularly the specific details of the exemplary embodiments disclosed herein, is given primarily for clarity of understanding, and no unnecessary limitations are to be understood therefrom, for modifications will become apparent to those skilled in the art upon reading this disclosure and may be made without departing from the spirit or scope of the claimed invention.

What is claimed is:

1. A device for detecting freshness of a perishable item, comprising:
   at least one sensor for detecting an analyte of interest in the perishable item, wherein the at least one sensor is a binary sensor;
   an integrated circuit for converting information detected by the at least one sensor into a signal; and
   an antenna portion for receiving and transmitting the signal from the integrated circuit, whereby the at least one sensor, the integrated circuit and the antenna portion are printed on a single sheet such that the device is unitary,
   wherein the antenna portion is configured to collect energy from an aerial device to activate the integrated circuit, and the integrated circuit is configured to cause the antenna to broadcast a unique identifier specific to the perishable item, pulse test a signal through the at least one sensor to detect voltage drop data across the at least one sensor, and cause the antenna portion to transmit the voltage drop data to an external receiver.

2. The device of claim 1, wherein the aerial device is one of near field communication (NFC), radio frequency identification (RFID), Zigbee, 802.15.4, Thread, or Bluetooth.

3. The device of claim 1, wherein the at least one sensor is a plurality of sensors.

4. The device of claim 3, wherein each of the plurality of sensors is tuned to a corresponding concentration of the analyte of interest.

5. The device of claim 4, wherein the corresponding concentration of the analyte of interest increases with respect to each successive one of the plurality of sensors.

6. The device of claim 3, wherein each of the plurality of sensors is configured to detect a different analyte of interest.

7. The device of claim 6, wherein the different analyte of interest is a different chemical for each of the plurality of sensors.

* * * * *